US010188718B2

United States Patent
Seeberger et al.

(10) Patent No.: US 10,188,718 B2
(45) Date of Patent: Jan. 29, 2019

(54) **VACCINES AGAINST *STREPTOCOCCUS PNEUMONIAE* SEROTYPE 4**

(71) Applicant: MAX-PLANCK-GESELLSCHAFT ZUR FÖRDERUNG DER WISSENSCHAFTEN E.V., Munich (DE)

(72) Inventors: Peter H. Seeberger, Kleinmachnow (DE); Claney Lebev Pereira, Berlin (DE); Chakkumkal Anish, The Hague (NL); Andreas Geissner, Berlin (DE)

(73) Assignee: Max-Planck-Gesellschaft zur Förderung der Wissenschaften e.V., Munich (DE)

( * ) Notice: Subject to any disclaimer, the term of this patent is extended or adjusted under 35 U.S.C. 154(b) by 33 days.

(21) Appl. No.: 15/534,676

(22) PCT Filed: May 15, 2015

(86) PCT No.: PCT/EP2015/060756
§ 371 (c)(1),
(2) Date: Jun. 9, 2017

(87) PCT Pub. No.: WO2016/091399
PCT Pub. Date: Jun. 16, 2016

(65) Prior Publication Data
US 2017/0333545 A1   Nov. 23, 2017

(30) Foreign Application Priority Data

Dec. 12, 2014 (EP) .................................... 14197832
Apr. 10, 2015 (EP) .................................... 15163253

(51) Int. Cl.
| | | |
|---|---|---|
| A61K 31/7028 | (2006.01) | |
| A61K 39/09 | (2006.01) | |
| A61K 31/715 | (2006.01) | |
| C08B 37/00 | (2006.01) | |
| C07H 15/02 | (2006.01) | |
| C07H 15/04 | (2006.01) | |
| A61K 39/385 | (2006.01) | |
| C07H 15/18 | (2006.01) | |
| G01N 33/569 | (2006.01) | |
| A61K 39/00 | (2006.01) | |

(52) U.S. Cl.
CPC .......... *A61K 39/092* (2013.01); *A61K 31/715* (2013.01); *A61K 39/385* (2013.01); *C07H 15/02* (2013.01); *C07H 15/04* (2013.01); *C07H 15/18* (2013.01); *C08B 37/006* (2013.01); *G01N 33/56944* (2013.01); *A61K 2039/575* (2013.01); *A61K 2039/627* (2013.01); *G01N 2333/3156* (2013.01); *G01N 2400/00* (2013.01); *G01N 2469/20* (2013.01)

(58) Field of Classification Search
None
See application file for complete search history.

(56) References Cited

PUBLICATIONS

Peeters et al., "A Comparative Study of the Immunogenicity of Pneumococcal Type 4 Polysaccharide and Oligosaccharide Tetanus Toxoid Conjugates in Adult Mice" Journal of Immunology vol. 146 No. 12 pp. 4308-4314 (Year: 1991).*
Goldblatt, D., et al., "Establishment of a New Human Pneumooccal Standard Reference Serum, 007sp," Clinical and Vaccine Immunology (Oct. 2011) 18 (10), pp. 1728-1736.
Higginbotham, J.D. et al., "Degradation of a Pneumococcal Type-Specific Polysaccharide with Exposure of Group-Specificity," Proceedings of the National Academy of Science (Sep. 1, 1970), vol. 67, No. 1, pp. 138-142.
Jones, C. et al., "The pneumococcal polysaccharide S4: A structural re-assessment," Carbohydrate Research, Pergamon, GB (Dec. 31, 1988) vol. 187, pp. 279-284.
Jones, C. et al., "N.M.R. and conformational analysis of the capsular polysaccharide from *Streptococcus pneumonaie* type 4," Carbohydrate Research, Pergamon, GB (Dec. 16, 1991) vol. 221, No. 1, pp. 95-121.
Kawano, Tetsu et al., "Natural killer-like nonspecific tumor cell lysis mediated by specific ligand-activated Vα14 NKT cells," Proc. Natl Acad. Sci. USA (May 1998) vol. 95, pp. 5690-5693.
Khaja, Sirajud D., "Novel galactosyl donor with 2-naphthylmethyl (NAP) as the non-participating group at C-2 position: efficient synthesis of α-galactosyl ceramide," Tetrahedron Letters (2010) vol. 51, pp. 4411-4414.
Klein, David L., "Pneumococcal Conjugate Vaccines: Review and Update," Microbial Drug Resistance (Jan. 1, 1995) vol. 1, No. 1, pp. 49-58.
Van De Wijgert, J.H. et al., "Immunogenicity of *Streptococcus pneumoniae* type 14 capsular polysaccharide: influence of carriers and adjuvants on isotype distribution," Infection and Immunity, American Society for Microbiology (Aug. 1, 1991) vol. 59, No. 8, pp. 2750-2757.
International Search Report and Written Opinion dated Aug. 6, 2015 for PCT Application No. PCT/EP2015/060756, filed May 15, 2015.
International Preliminary Report on Patentability dated Jun. 13, 2017 for PCT Application No. PCT/EP2015/060756, filed May 15, 2015.

* cited by examiner

*Primary Examiner* — Eric Olson
(74) *Attorney, Agent, or Firm* — Knobbe, Martens, Olson & Bear, LLP

(57) ABSTRACT

The present invention relates to synthetic saccharides of general formula (I) that are related to *Streptococcus pneumoniae* serotype 4 capsular polysaccharide and conjugates thereof. Said conjugate and a pharmaceutical composition containing said conjugate are useful for prevention and/or treatment of diseases associated with *Streptococcus pneumoniae*, and more specifically of diseases associated with *Streptococcus pneumoniae* serotype 4. Furthermore, the synthetic saccharides of general formula (I) are useful as marker in immunological assays for detection of antibodies against *Streptococcus pneumoniae* bacteria.

25 Claims, 5 Drawing Sheets

H, K: Proteins F,M,N,O: Isolated polysaccharides

VACCINES AGAINST STREPTOCOCCUS PNEUMONIAE SEROTYPE 4

CROSS REFERENCE TO RELATED APPLICATIONS

This application is a U.S. National Phase Application of PCT International Application No. PCT/EP2015/060756, filed on May 15, 2015, designating the United States of America and published in the English language, which claims priority to EP Application Nos. 14197832.0, filed Dec. 12, 2014; and 15163253.6, filed Apr. 10, 2015. The disclosures of the above-referenced applications are hereby expressly incorporated by reference in their entireties.

FIELD OF THE INVENTION

The present invention relates to synthetic saccharides of general formula (I) that are related to *Streptococcus pneumoniae* serotype 4 capsular polysaccharide and conjugates thereof. Said conjugate and a pharmaceutical composition containing said conjugate are useful for prevention and/or treatment of diseases associated with *Streptococcus pneumoniae*, and more specifically of diseases associated with *Streptococcus pneumoniae* serotype 4. Furthermore, the synthetic saccharides of general formula (I) are useful as marker in immunological assays for detection of antibodies against *Streptococcus pneumoniae* bacteria.

BACKGROUND OF THE INVENTION

*Streptococcus pneumoniae* is a Gram-positive, encapsulated bacterium that is a main cause of infections of the respiratory tract and can lead to severe invasive pneumococcal disease (IPD). More than 90 different pneumococcal serotypes have been described to date. These are classified by the structure of their capsular polysaccharide (CPS), which is unique to each serotype. Consequently, the immune response generated against the CPS varies between different serotypes. This is used to generate specific antibodies in rabbits against the antigen of each serotype. Cross-reactivity between these specific antibodies and other serotypes than those they were raised against is often observed, due to structural similarities of the CPS of different serotypes. Due to its immunological properties, CPS is used as the main component of *S. pneumoniae* vaccines.

The first efficient vaccine that contained the CPS of four different serotypes was described in 1945. It then took over thirty years until a vaccine was introduced that covered 14 serotypes, shortly followed by a 23-valent vaccine. However, these polysaccharide vaccines had several shortcomings. They were not able to elicit a long-lasting protection and were not effective in the populations most vulnerable to infection, namely children under two years of age, as well as immunodeficient and elderly patients. These shortcomings result from the immunology of carbohydrates and were overcome by the introduction of carbohydrate-protein conjugate vaccines. The first pneumococcal conjugate vaccines were the seven-valent (PCV-7) and 10-valent (PCV-10) vaccine. PCV-7 was later replaced with the most recent vaccine (PCV-13), which contains the CPS-glycoconjugates of 13 different serotypes.

*Streptococcus pneumoniae* serotype 4 CPS is included in all pneumococcal conjugate vaccines. The SP4 CPS consists of a tetrasaccharide repeating unit with the sequence β-(1, 3)-ManNAc-α-(1,3)-FucNAc-α-(1,3)-GalNAc-α-(1,4)-Gal containing an acid labile trans-2, 3 (S)-pyruvate on the galactose moiety (see FIG. 1). Trans-pyruvate ketals are labile to hydrolysis and therefore, are inducing micro heterogeneities to the saccharides isolated from bacterial sources that are intended for vaccinations. Hence, the labile nature of the pyruvate moiety has enormous implications on the structure of the saccharides isolated from *S. pneumoniae* type 4 bacterial sources and therefore, impacts on the production and stability of the conjugate comprising said saccharides. Structural heterogeneities are detrimental, when considering the trend of vaccine development going in the direction of well-defined subunit vaccines.

It is the objective of the present invention to provide well-defined synthetic saccharides of general formula (I) that are related to *Streptococcus pneumoniae* serotype 4 capsular polysaccharides. Said saccharides are suitable to be conjugated to an immunogenic carrier to provide conjugates and pharmaceutical composition thereof that are useful for prevention and/or treatment of diseases associated with *Streptococcus pneumonia*, and more specifically of diseases associated with *Streptococcus pneumoniae* serotype 4. Furthermore, the synthetic saccharides of general formula (I) are useful as marker in immunological assays for detection of antibodies against *Streptococcus pneumoniae* bacteria.

The objective of the present invention is solved by the teaching of the independent claims. Further advantageous features, aspects and details of the invention are evident from the dependent claims, the description, the figures, and the examples of the present application.

DESCRIPTION OF THE INVENTION

Definitions

The term "linker" as used herein encompasses molecular fragments capable of connecting the reducing-end monosaccharide of a saccharide with an immunogenic carrier or a solid support, optionally by binding to at least one interconnecting molecule. Thus, the function of the linker per se or together with the interconnecting molecule is to establish, keep and/or bridge a special distance between the reducing-end monosaccharide and an immunogenic carrier or a solid support. More specifically, one extremity of the linker is connected to the exocyclic oxygen atom at the anomeric center of the reducing-end monosaccharide and the other extremity is connected via the nitrogen atom with the interconnecting molecule, or directly with the immunogenic carrier or the solid support.

As used herein, the term "interconnecting molecule" refers to a bifunctional molecule containing functional group X and functional group Y, wherein functional group X is capable of reacting with the terminal amino group on the linker L and the functional group Y is capable of reacting with a functionality present on an immunogenic carrier or on a solid support. FIG. 2 displays examples of commercially available interconnecting molecules, but does not restrict the interconnecting molecules that can be used according to the present invention to the examples displayed herein.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the person skilled in the art, classically recognized examples of adjuvants include:
  mineral-containing compositions, including calcium salts and aluminum salts (or mixtures thereof). Calcium salts include calcium phosphate. Aluminum salts include hydroxides, phosphates, sulfates, etc., with the salts taking any suitable form (e.g. gel, crystalline, amorphous, etc.). Adsorption to these salts is preferred. The mineral containing compositions may also be formulated as a particle of metal salt. The adjuvants known as aluminum hydroxide and aluminum phosphate may be also used. The invention can use any of the "hydroxide" or "phosphate" adjuvants that are in general used as adjuvants. The adjuvants known as "aluminum hydroxide" are typically aluminum oxyhydroxide salts, which are usually at least partially crystalline. The adjuvants known as "aluminum phosphate" are typically aluminum hydroxyphosphates, often also containing a small amount of sulfate (i.e. aluminum hydroxyphosphate sulfate). They may be obtained by precipitation, and the reaction conditions and concentrations during precipitation influence the degree of substitution of phosphate for hydroxyl in the salt. Mixtures of both an aluminum hydroxide and an aluminum phosphate can be employed in the formulation according to the present invention;

saponins, which are a heterologous group of sterol glycosides and triterpenoid glycosides that are found in the bark, leaves, stems, roots and even flowers of a wide range of plant species. Saponins from the bark of the *Quillaia saponaria*, Molina tree have been widely studied as adjuvants. Saponins can also be commercially obtained from *Smilax ornata* (sarsaprilla), *Gypsophilla paniculata* (brides veil), and *Saponaria oficianalis* (soap root). Saponin adjuvant formulations include purified formulations, such as QS21, as well as lipid formulations, such as ISCOMs. Saponin compositions have been purified using HPLC and RP-HPLC. Specific purified fractions using these techniques have been identified, including QS7, QS 17, QS 18, QS2 1, QH-A, QH-B and QH-C. Saponin formulations may also comprise a sterol, such as cholesterol. Combinations of saponins and cholesterols can be used to form unique particles called immunostimulating complexes (ISCOMs). ISCOMs generally include a phospholipid such as phosphatidylethanolamine or phosphatidylcholine. Any known saponin can be used in ISCOMs. Preferably, the ISCOM includes one or more of QuilA, QHA & QHC;

microparticles (i.e. a particle of 100 nm to 150 pm in diameter, more preferably 200 nm to 30 pm in diameter, or 500 nm to 10 pm in diameter) formed from materials that are biodegradable and non-toxic. Such non-toxic and biodegradable materials include, but are not restricted to poly($\alpha$-hydroxy acid), polyhydroxybutyric acid, polyorthoester, polyanhydride, polycaprolactone;

CD1d ligands, such as an $\alpha$-glycosylceramide, phytosphingosine-containing $\alpha$-glycosylceramides, OCH, KRN7000 [(2S,3S,4R)-1-O-($\alpha$-D-galactopyranosyl)-2-(N-hexacosanoylamino)-1,3,4-octadecanetriol], CRONY-101, 3"-sulfo-galactosyl-ceramide;

immunostimulatory oligonucleotides, such CpG motif containing ones (a dinucleotide sequence containing an unmethylated cytosine residue linked by a phosphate bond to a guanosine residue), or CpI motif containing ones (a dinucleotide sequence containing cytosine linked to inosine), or a double-stranded RNA, or an oligonucleotide containing a palindromic sequence, or an oligonucleotide containing a poly(dG) sequence. Immunostimulatory oligonucleotides can include nucleotide modifications/analogs such as phosphorothioate modifications and can be double-stranded or (except for RNA) single-stranded;

compounds containing lipids linked to a phosphate-containing acyclic backbone, such as the TLR4 antagonist E5564;

oil emulsions (e.g. Freund's adjuvant, MF59®).

Theoretically, each molecule or substance that is able to favor or amplify a particular situation in the cascade of immunological events, ultimately leading to a more pronounced immunological response, can be defined as an adjuvant.

In principle, through the use of adjuvants in vaccine formulations, one can direct and optimize immune responses that are appropriate or desirable for the vaccine;

enable mucosal delivery of vaccines, i.e. administration that results in contact of the vaccine with a mucosal surface such as buccal or gastric or lung epithelium and the associated lymphoid tissue;

promote cell-mediated immune responses;

enhance the immunogenicity of weaker immunogens, such as highly purified or recombinant antigens;

reduce the amount of antigen or the frequency of immunization required to provide protective immunity; and improve the efficacy of vaccines in individuals with reduced or weakened immune responses, such as newborns, the aged, and immunocompromised vaccine recipients.

Although little is known about their mode of action, it is currently believed that adjuvants augment immune responses by one of the following mechanisms:

increasing the biological or immunologic half-life of antigens;

improving antigen delivery to antigen-presenting cells (APCs), as well as antigen processing and presentation by the APCs e.g., by enabling antigen to cross endosomal membranes into the cytosol after ingestion of antigen-adjuvant complexes by APC;

mimicking danger inducing signals from stressed or damaged cells, which serve to initiate an immune response;

inducing the production of immunomodulatory cytokines;

biasing the immune response towards a specific subset of the immune system; and blocking the rapid dispersal of the antigen challenge.

Saccharides are known by the person skilled in the art as TI-2 (T cell independent-2) antigens and poor immunogens. Therefore, to produce a saccharide-based vaccine, said saccharides are conjugated to an immunogenic carrier to provide a conjugate, which presents an increased immunogenicity in comparison with the saccharide. In this context the term "immunogenic carrier" is defined as a structure, which is conjugated to the saccharide to form a conjugate that presents an increased immunity in comparison with the saccharide per se. Thus, the conjugation of the saccharides to the immunogenic carrier has as effect the stimulation of the immune response against said saccharide, without inducing an immune response against the said immunogenic carrier.

Hence, the present invention is directed to a saccharide of general formula (I)

$$V^*—[U_{x+3}—U_{x+2}—U_{x+1}—U_x]_n—V—O-L-NH_2 \quad (I)$$

wherein
x is an integer selected from 1, 2, 3 and 4;
n is an integer selected from 1, 2 and 3;

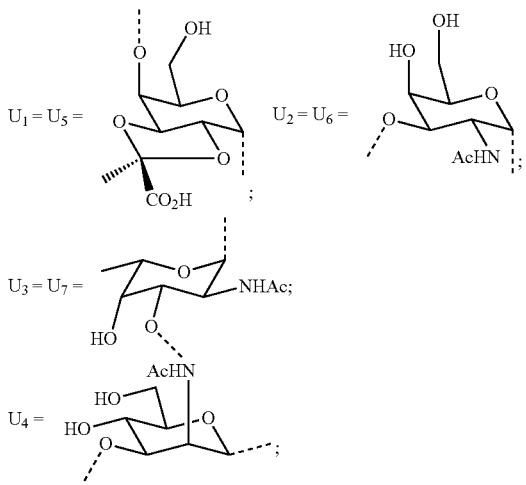

—V— represents a bond, —U$_{x+3}$—, —U$_{x+3}$—U$_{x+2}$— or —U$_{x+3}$—U$_{x+2}$—U$_{x+1}$—;
V*— represents H—, H—U$_x$—, H—U$_{x+1}$—U$_x$—, H—U$_{x+2}$—U$_{x+1}$—U$_x$—;
L represents a linker;
and diastereoisomers and pharmaceutically acceptable salts thereof.

The linker L preferably contains between 2 and 40 carbon atoms (including the carbon atoms of optional side chains), more preferably between 2 and 30, more preferably between 2 and 20, more preferably between 2 and 14, more preferably between 2 and 12, and still more preferably between 2 and 10 carbon atoms. This is the total number of carbon atoms of L including any carbon atoms of substituents.

The shortest atom chain between the oxygen atom (i.e. the oxygen of —O-L-NH$_2$) and the NH$_2$-group consists preferably of 2 to 14 atoms, more preferably of 2 to 12 atoms, more preferably of 2 to 10 atoms, more preferably of 2 to 8 atoms. In case the shortest chain (which is the shortest possible connection between the oxygen at the anomeric center and the NH$_2$-group) consists of 2 to 6 atoms, these are preferably carbon atoms. In case the shortest chain consists of 4 to 8 atoms, the chain may contain 1, 2 or 3 heteroatoms selected from O, N and S. In case the shortest chain consists of 9 to 14 atoms, the chain may contain 1, 2, 3, 4, 5, or 6 heteroatoms selected from O, N and S.

The linker -L-, or the shortest chain may be fully or partially fluorinated. The linker -L- may contain a 3-membered or a 4-membered or a 5-membered or a 6-membered saturated carbocycle or a 5-membered partly unsaturated (and not aromatic) carbocycle or a 4-membered or a 5-membered or a 6-membered saturated oxygen heterocycle or a 4-membered or a 5-membered or a 6-membered saturated nitrogen heterocycle or a 6-membered aromatic carbocycle. The linker -L- may also contain amide (—NH—CO—, —CO—NH—) and/or urea (—NH—CO—NH—) residues and preferably only one amide or urea residue. The linker may also contain substituents and preferably two substituents such as R$^{10}$ and R$^{11}$ or four substituents such as R$^{10}$, R$^{11}$, R$^{15}$ and R$^{14}$, which have the meanings as defined herein and which are preferably selected from: —F, —Cl, —CH$_3$, —C$_2$H$_5$, —C$_3$H$_7$, —C$_5$H$_9$, —C$_6$H$_{13}$, —OCH$_3$, —OC$_2$H$_5$, —CH$_2$F, —CHF$_2$, —CF$_3$, —C(O)—NH$_2$, —SCH$_3$, —SC$_2$H$_5$, —NHC(O)CH$_3$, —N(CH$_3$)$_2$, and —N(C$_2$H$_5$)$_2$;

In case the linker -L- is fluorinated, more than two substituents —F are preferred.

Preferably the linker -L- is selected from: —CH$_2$—, —(CH$_2$)$_2$—, —(CH$_2$)$_3$—, —(C$_2$)$_4$—, —(CH$_2$)$_5$—, —(CH$_2$)$_6$—, —(CH$_2$)$_7$—, —(CH$_2$)$_8$—, —(CH$_2$)$_9$—, —(CH$_2$)$_{10}$—, —CF$_2$—, —(CF$_2$)$_2$—, —(CF$_2$)$_3$—, —(CF$_2$)$_4$—, —(CF$_2$)$_5$—, —(CF$_2$)$_6$—, —(CF$_2$)$_7$—, —(CF$_2$)$_8$—, —(CF$_2$)$_9$—, —(CF$_2$)$_{10}$—, —(CH$_2$)$_2$—O—(CH$_2$)$_2$—, —CH$_2$—O—(CH$_2$)$_3$—, —(CH$_2$)$_3$—O—CH$_2$—, —CH$_2$—O—(CH$_2$)$_2$—, —(CH$_2$)$_2$—O—CH$_2$—, —(CH$_2$)$_3$—O—(CH$_2$)$_2$—, —(CH$_2$)$_2$—O—(CH$_2$)$_3$—, —(CH$_2$)$_4$—O—CH$_2$—, —CH$_2$—O—(CH$_2$)$_4$—, -L$^a$-, -L$^a$-L$^e$-, -L$^a$-L$^b$-L$^e$-, -L$^a$-L$^b$-L$^d$-L$^c$-L$^e$-, -L$^a$-L$^d$-L$^e$-;
wherein
-L$^a$- is selected from: —(CH$_2$)$_o$—, —(CF$_2$)$_o$—, —(CH$_2$—CH$_2$—O)$_o$—C$_2$H$_4$—, —(CH$_2$—CH$_2$—O)$_o$—CH$_2$—, —(CR$^{10}$R$^{11}$)$_o$—,

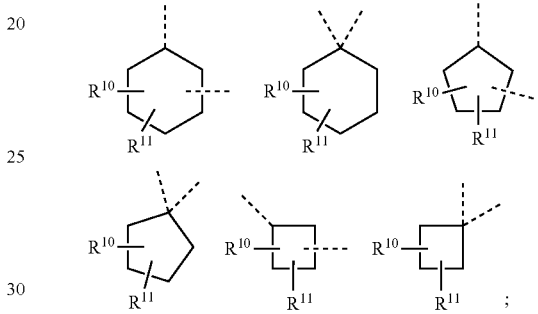

-L$^b$- and -L$^c$- are independently of each other selected from: —O—, —NH—C(O)—NH—, —NH—C(S)—NH—, —NH—C(O)—, —(O)—NH—, —NH—C(O)—O—, —NR$^9$—, —NR$^{18}$—, —SO$_2$—,

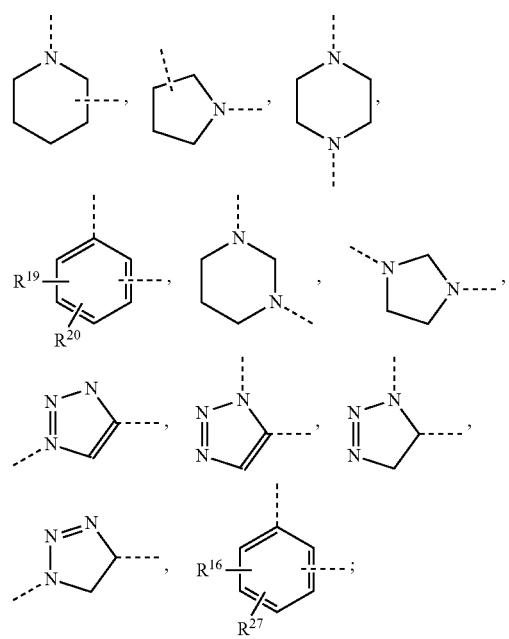

-L$^d$- represents —(CH$_2$)$_q$—, —(CF$_2$)$_q$—, —(CR$^{12}$R$^{13}$)$_q$—, —(CH$_2$—CH$_2$—O)$_q$—C$_2$H$_4$—, —(CH$_2$—CH$_2$—O)$_q$—CH$_2$—,

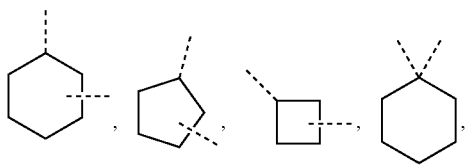

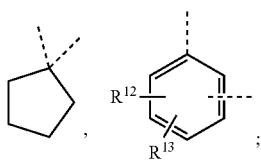

$L^e$- is selected from: —$(CH_2)_{p1}$—, —$(CF_2)_{p1}$—, —$C_2H_4$—$(O$—$CH_2$—$CH_2)_{p1}$—, —$CH_2$—$(O$—$CH_2$—$CH_2)_{p1}$—, —$(CH_2)_{p1}$—$O$—$(C_2)_{p2}$—, —$(CR^{14}R^{15})_{p1}$—, —$(CR^{14}R^{15})_{p1}$—$O$—$(CR^{21}R^{22})_{p2}$—,

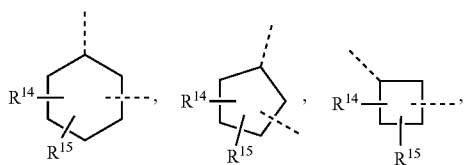

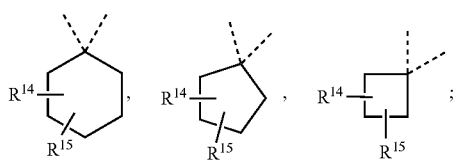

$R^9$ and $R^{18}$ are independently of each other selected from: —$CH_3$, —$C_2H_5$, —$C_3H_7$ and —$C(O)CH_3$;

$R^{13}$, $R^{11}$, $R^{12}$, $R^{13}$, $R^{14}$, $R^{15}$, $R^{16}$, $R^{17}$, $R^{19}$, $R^{20}$, $R^{21}$ and $R^{22}$ are independently of each other selected from: —H, —F, —Cl, —$CH_3$, —$C_2H_5$, —$C_3H_7$, —$C_5H_9$, —$C_6H_{13}$, —$OCH_3$, —$OC_2H_5$, —$CH_2F$, —$CHF_2$, —$CF_3$, —$C(O)$—$NH_2$, —$SCH_3$, —$SC_2H_5$, —$NHC(O)CH_3$, —$N(CH_3)_2$ and —$N(C_2H_5)_2$;

o, q, p1 and p2 are independently of each other an integer selected from 1, 2, 3, 4, 5, 6, 7, 8, 9, and 10.

The saccharides of the present invention bear basic and/or acidic substituents and they may form salts with organic or inorganic acids or bases.

Examples of suitable acids for such acid addition salt formation are hydrochloric acid, hydrobromic acid, sulfuric acid, phosphoric acid, acetic acid, citric acid, oxalic acid, malonic acid, salicylic acid, p-aminosalicylic acid, malic acid, fumaric acid, succinic acid, ascorbic acid, maleic acid, sulfonic acid, phosphonic acid, perchloric acid, nitric acid, formic acid, propionic acid, gluconic acid, lactic acid, tartaric acid, hydroxymaleic acid, pyruvic acid, phenylacetic acid, benzoic acid, p-aminobenzoic acid, p-hydroxybenzoic acid, methanesulfonic acid, ethanesulfonic acid, nitrous acid, hydroxyethanesulfonic acid, ethylenesulfonic acid, p-toluenesulfonic acid, naphthylsulfonic acid, sulfanilic acid, camphorsulfonic acid, china acid, mandelic acid, o-methylmandelic acid, hydrogen-benzenesulfonic acid, picric acid, adipic acid, d-o-tolyltartaric acid, tartronic acid, (o, m, p)-toluic acid, naphthylamine sulfonic acid, and other mineral or carboxylic acids well known to those skilled in the art. The salts are prepared by contacting the free base form with a sufficient amount of the desired acid to produce a salt in the conventional manner.

Examples of suitable inorganic or organic bases are, for example, NaOH, KOH, $NH_4OH$, tetraalkylammonium hydroxide, lysine or arginine and the like. Salts may be prepared in a conventional manner using methods well known in the art, for example by treatment of a solution of the compound of the general formula (I) with a solution of a base, selected out of the group mentioned above.

Further, it is also possible that the compounds of the present invention bear simultaneously basic and acid groups. Further, it may also occur that these basic and acid groups appear to be in close vicinity to one another enabling an intramolecular proton transfer from the acidic group to the basic group. Therefore, in a preferred embodiment of the present invention the compound of the formula (I) may be zwitter-ionic, bearing at least e.g. one —$O^-$ and one —$NH_3^+$ group.

It is clear for the skilled person in the art of carbohydrate chemistry that the saccharides of general (I) are not containing —O—O— bonds and or sugar fragments ($U_x$, $U_{x+1}$, $U_{x+2}$, $U_{x+3}$) connected or bound to each other via their anomeric or C-1 carbons.

The saccharides of general formula (I) are able to induce a protective immune response against *Streptococcus pneumoniae* serotype 4 bacteria in a human and/or animal host. The presence of the (S)-pyruvate ketal at the positions 2 and 3 of the galactose moiety is essential for achieving cross-reactivity towards the native *S. pneumoniae* type 4 capsular polysaccharides. As the trans-pyruvate ketals are labile to hydrolysis, the *S. pneumoniae* serotype 4 related saccharides (native capsular polysaccharides and fragments thereof) isolated from bacterial sources are besides not being homogeneous in term of size, also non-homogeneous in terms of structure. However, this drawback is overcome with the well-defined synthetic saccharides of the present invention, which are able to elicit in a human and/or animal host high titers of antibodies that are cross-reacting with the natural SP-4 polysaccharides and present opsonophagocytosis and bactericidal activity, thus conferring protection against *S. pneumoniae* serotype 4 bacteria.

Preferred are saccharides of general formula (II)

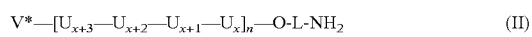

$V^*$—$[U_{x+3}$—$U_{x+2}$—$U_{x+1}$—$U_x]_n$—O-L-$NH_2$ (II)

wherein x, n, L, $U_x$, $U_{x+1}$, $U_{x+2}$, $U_{x+3}$ and $V^*$ have the meanings defined herein.

Thus, a saccharide of general formula (II-a), (II-b), (II-c) or (II-d), wherein n, L and $V^*$ have the meanings defined herein is especially preferred.

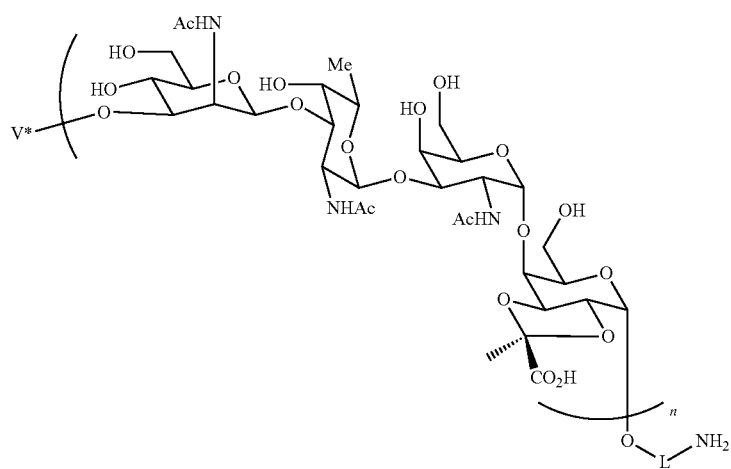
II-a
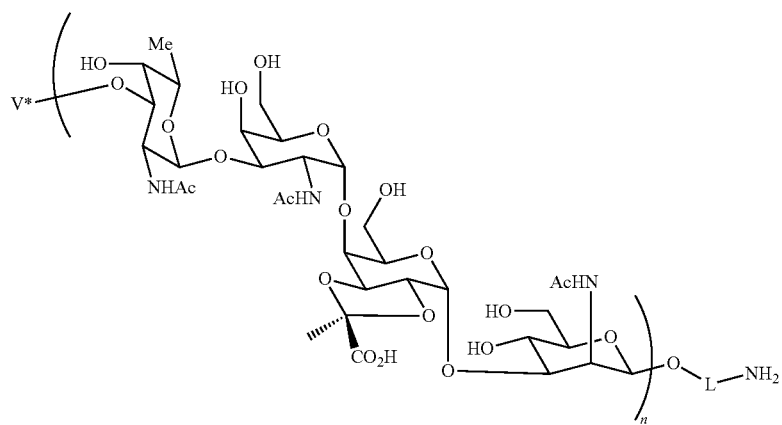
II-b
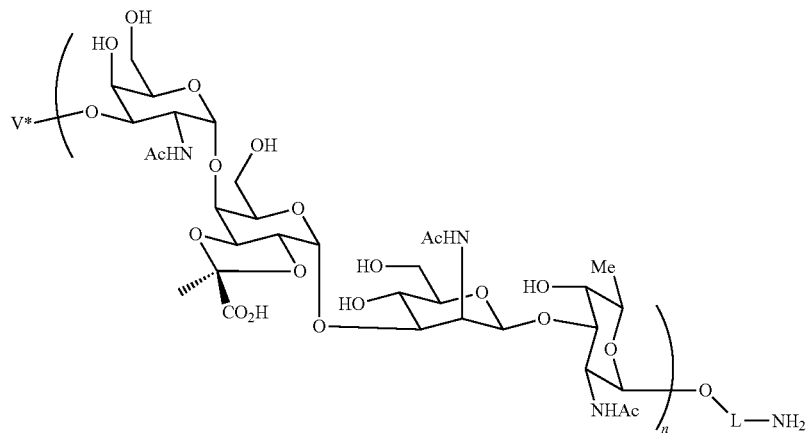
II-c

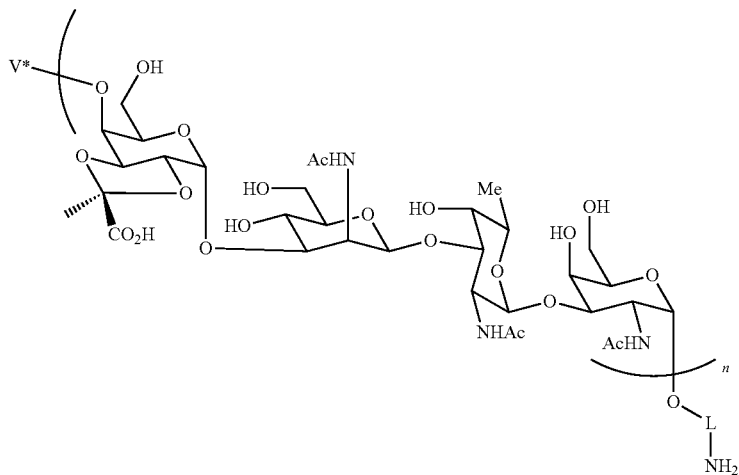
II-d
Also preferred are saccharides of general formula (III)
$$V^*—[U_{x+3}—U_{x+2}—U_{x+1}—U_x]_n—U_{x+3}—O\text{-}L\text{-}NH_2 \quad (III)$$
wherein x, n, L, $U_x$, $U_{x+1}$, $U_{x+2}$, $U_{x+3}$ and V* have the meanings defined herein.
Thus, a saccharide of general formula (III-a), (III-b), (III-c) or (III-d), wherein n, L and V* have the meanings defined herein is also preferred.
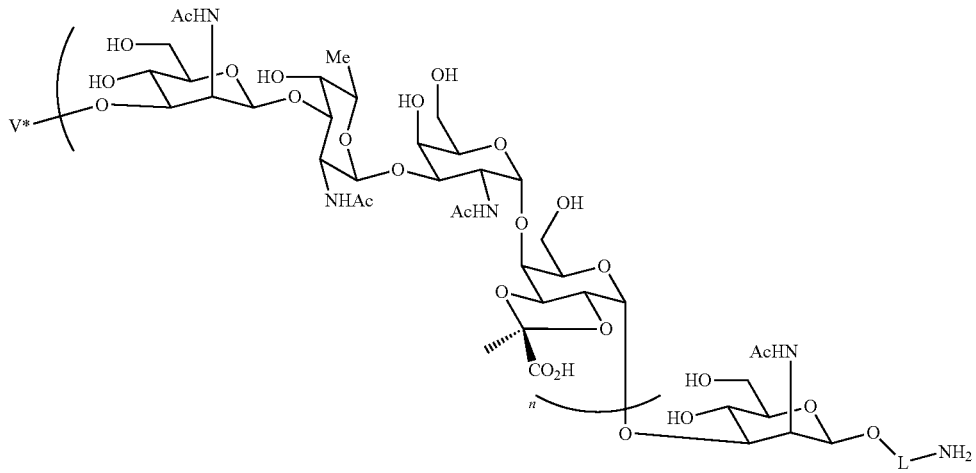
III-a
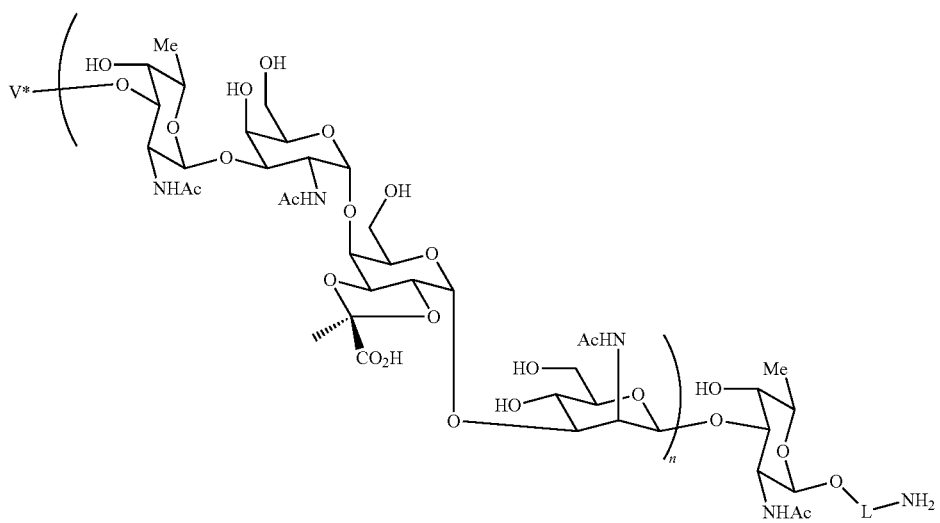
III-b -continued

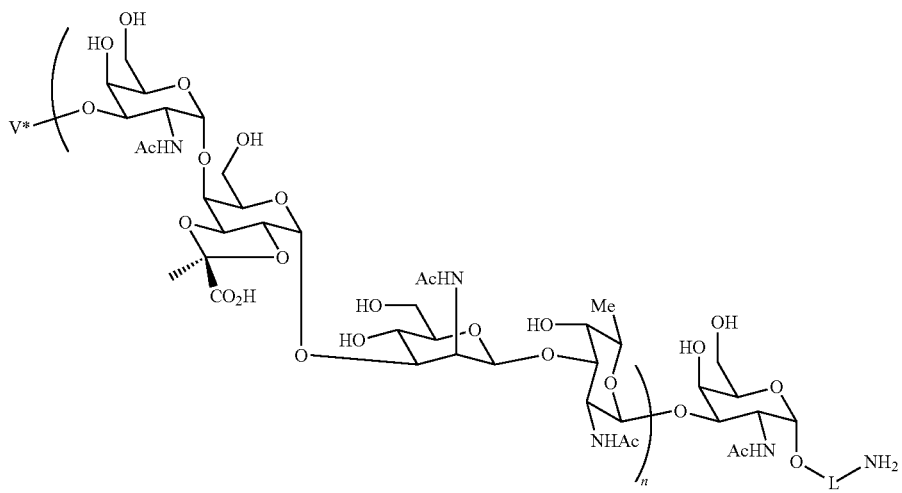
III-c

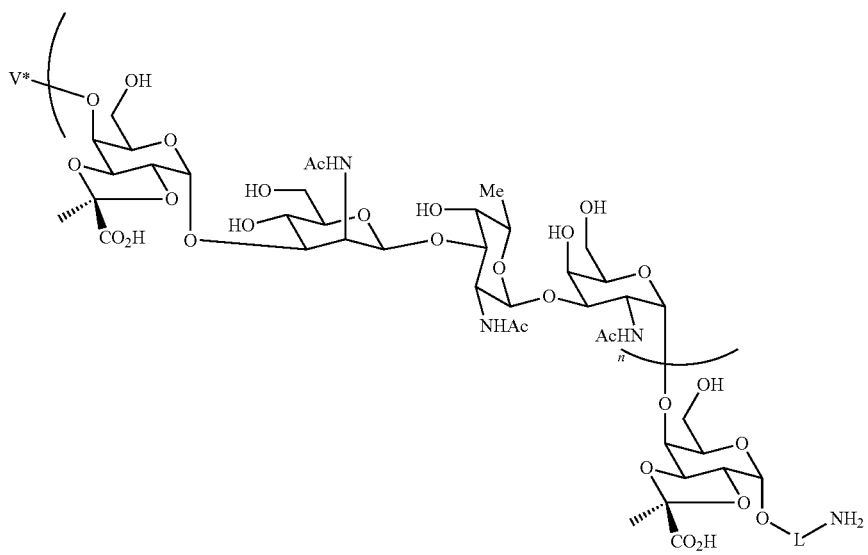
III-d

A preferred embodiment according to the present invention is directed to a saccharide of general formula (IV)

$$V^*-[U_{x+3}-U_{x+2}-U_{x+1}-U_x]_n-U_{x+3}-U_{x+2}-O-L-NH_2 \quad (IV)$$

wherein x, n, L, $U_x$, $U_{x+1}$, $U_{x+2}$, $U_{x+3}$ and V* have the meanings defined herein. Hence, a saccharide of general formula (IV-a), (IV-b), (IV-c) or (IV-d), wherein V*, n and L have the meanings defined herein is particularly preferred.

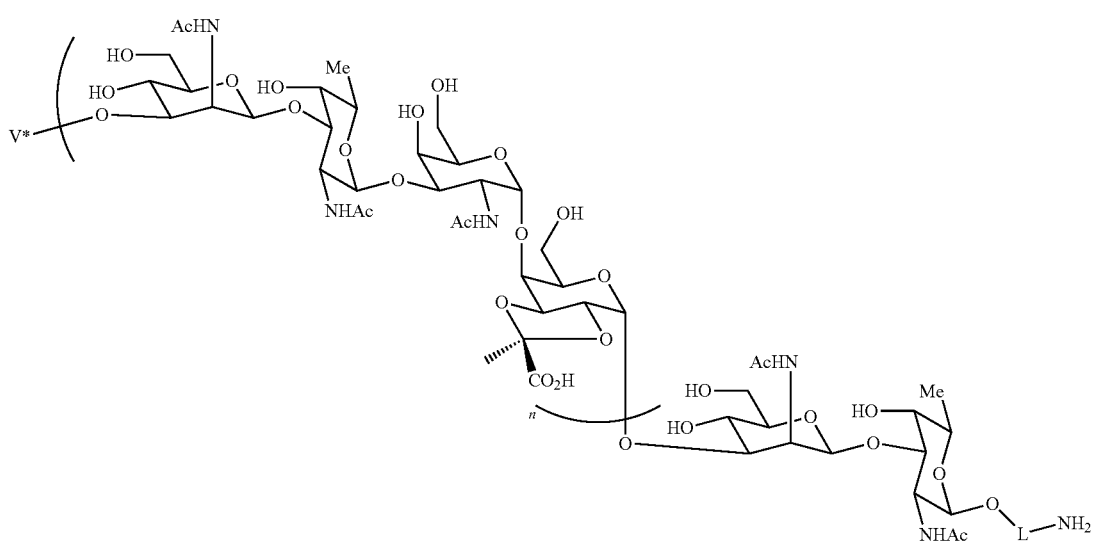
IV-a
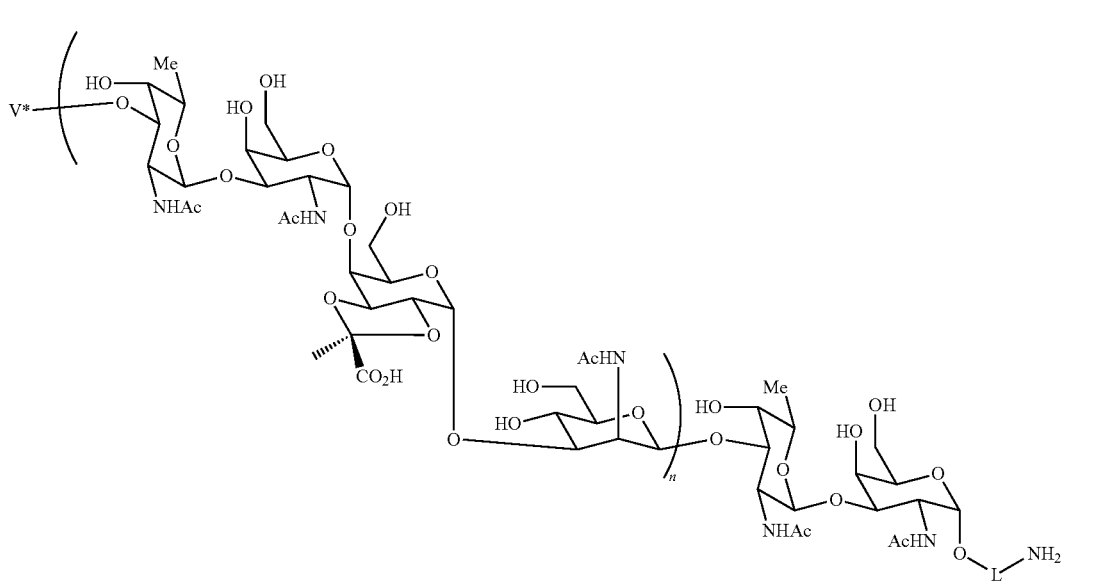
IV-b
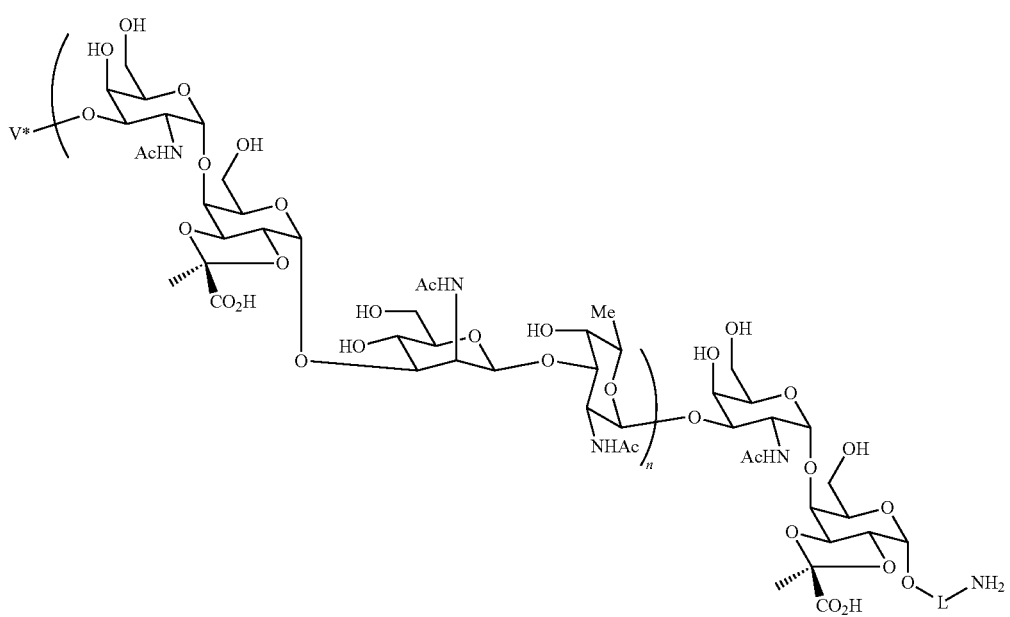
IV-c

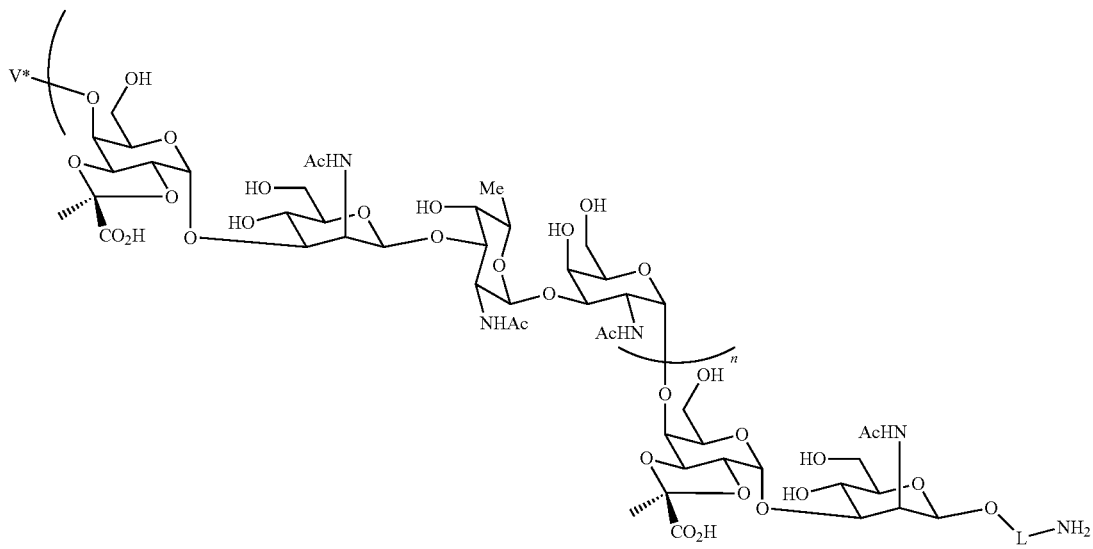
Also preferred are saccharides of general formula (V)
$$V^*-[U_{x+3}-U_{x+2}-U_{x+1}-U_x]_n-U_{x+3}-U_{x+2}-U_{x+1}-O\text{-}L\text{-}NH_2 \quad (V)$$
wherein x, n, L, $U_x$, $U_{x+1}$, $U_{x+2}$, $U_{x+3}$ and V* have the meanings defined herein.
Also preferred is a saccharide of general formula (V-a), (V-b), (V-c) or (V-d), wherein n, L and V* have the meanings defined herein.
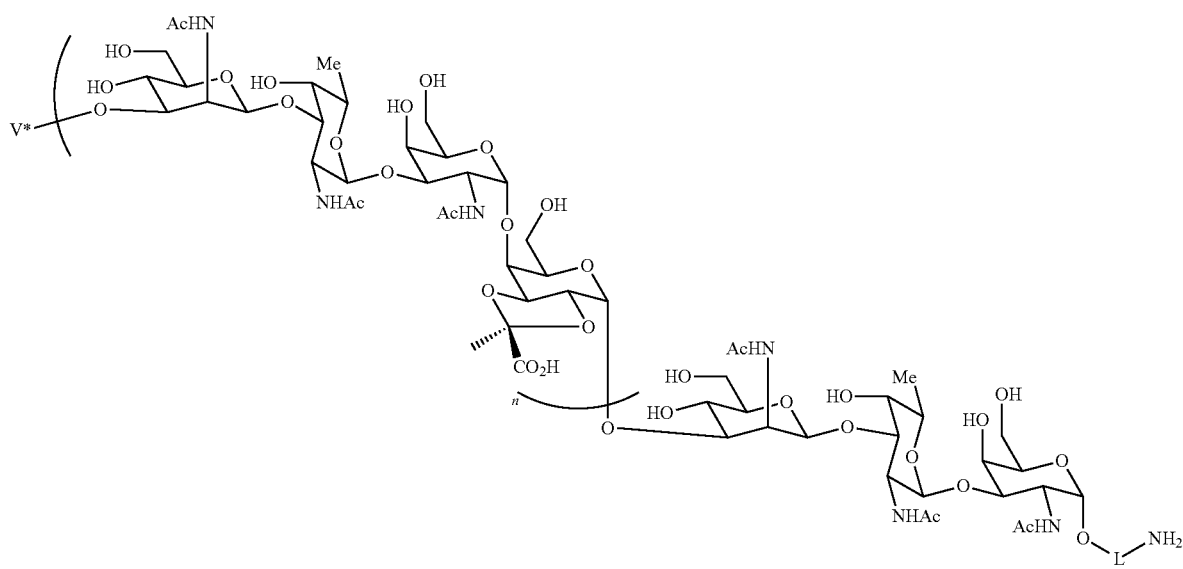

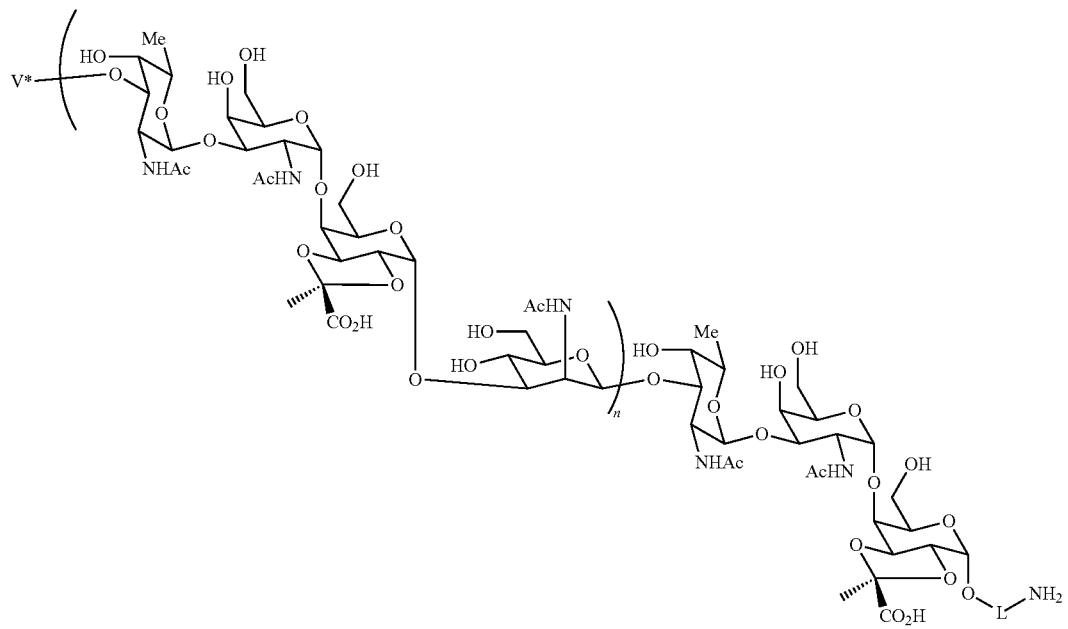
V-b
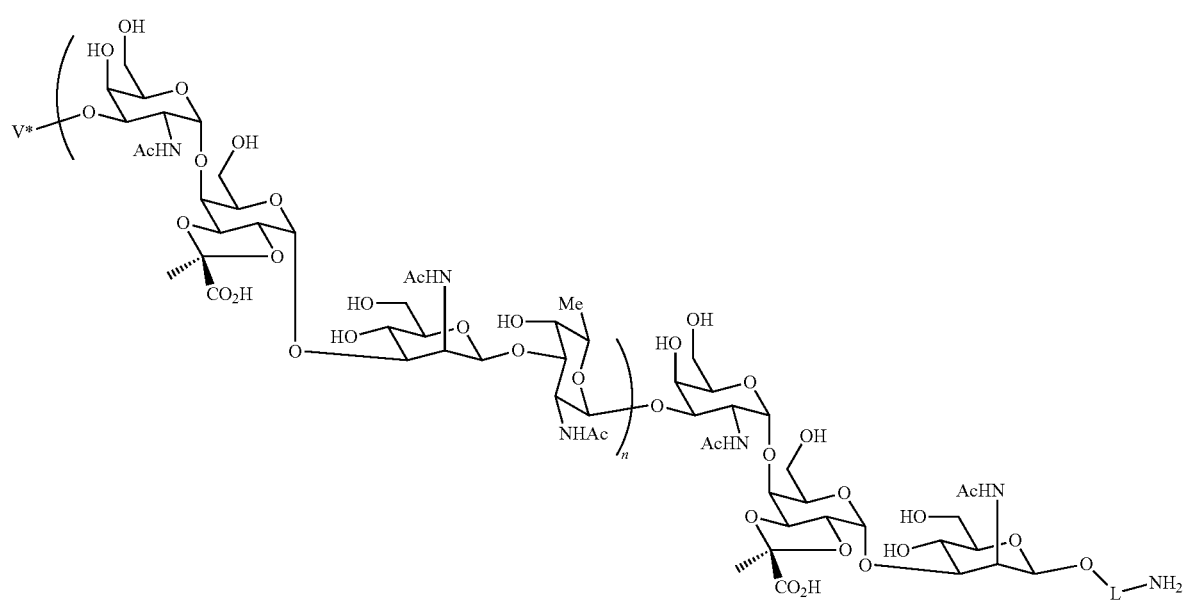
V-c

V-d

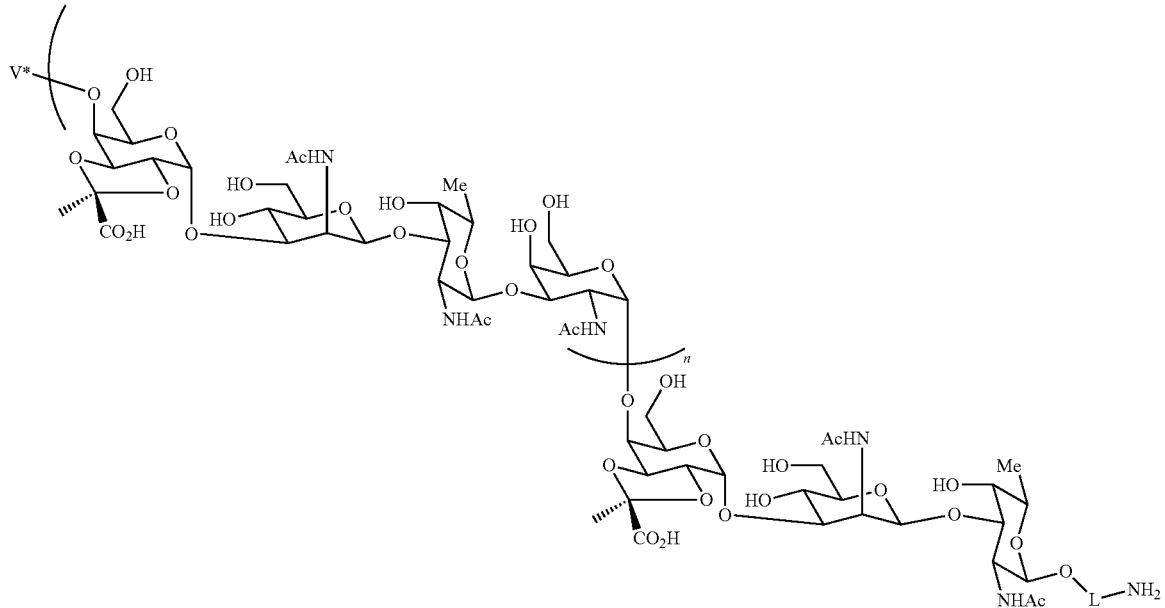

Preferably the integer x represents 1. Therefore, a compound of general formula (I), (II), (III), (IV) or (V), wherein x represents 1 is especially preferred. Even more preferred is a compound of general formula (I), (II), (III), (IV) or (V), wherein x represents 1 and V* represents H—. A saccharide of general formula (I), (II), (III), (IV) or (V), wherein V* represents H is also preferred.

Preferably, the integer n represents 1. Hence, a saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c) or (V-d), wherein n represents 1 is especially preferred.

Preferably, the linker -L- is selected from: -$L^a$-, -$L^a$-$L^e$-, -$L^a$-$L^b$-$L^e$-, -$L^a$-$L^d$-$L^e$-;
wherein
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—(—O—$CH_2$—$CH_2)_{p1}$—, —$CH_2$—(O—$CH_2$—$CH_2)_{p1}$— and —$(CH_2)_{p1}$—O—$(CH_2)_{p2}$—;
and o, q, p1 and p2 are independently of each other an integer selected from 1, 2, 3, 4, 5, and 6.

Therefore, a saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c) or (V-d) wherein
-L- is selected from: -$L^a$-, -$L^a$-$L^e$-, -$L^a$-$L^b$-$L^e$-, and -$L^a$-$L^d$-$L^e$-;
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—(—O—$CH_2$—$CH_2)_{p1}$—, —$CH_2$—(O—$CH_2$—$CH_2)_{p1}$— and —$(CH_2)_{p1}$—O—$(CH_2)_{p2}$—;
and o, q, p1 and p2 are independently of each other an integer selected from 1, 2, 3, 4, 5, and 6 is especially preferred.

A saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c) or (V-d) wherein
-L- is selected from: -$L^a$-, -$L^a$-$L^e$-, -$L^a$-$L^b$-$L^e$-, and -$L^a$-$L^d$-$L^e$-;
-$L^a$- is selected from: —$(CH_2)_o$—, —$(CH_2$—$CH_2$—$O)_o$—$C_2H_4$—, —$(CH_2$—$CH_2$—$O)_o$—$CH_2$—;
-$L^b$- represents —O—;
-$L^d$- is selected from: —$(CH_2)_q$—, —$(CF_2)_q$—, —$(CH_2$—$CH_2$—$O)_q$—$C_2H_4$—, and —$(CH_2$—$CH_2$—$O)_q$—$CH_2$—;
-$L^e$- is selected from: —$(CH_2)_{p1}$—, —$(CF_2)_{p1}$—, —$C_2H_4$—(O—$CH_2CH_2)_{p1}$—, —$CH_2$—(O—$CH_2$—$CH_2)_{p1}$— and —$(CH_2)_{p1}$—O—$(CH_2)_{p2}$—;
o, q, p1 and p2 are independently of each other an integer selected from 1, 2, 3, 4, 5, and 6; and n represents 1 is also preferred.

Even more preferred is a saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c) or (V-d), wherein -L- represents —$(CH_2)_o$— and o is an integer selected from 2, 3, 4, 5 and 6.

Also preferred is a saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c) or (V-d), wherein -L- represents —$(CH_2)_o$—, o is an integer selected from 2, 3, 4, 5 and 6, and n represents 1.

In yet another preferred embodiment, the saccharide according to the present invention is selected from the group consisting of:

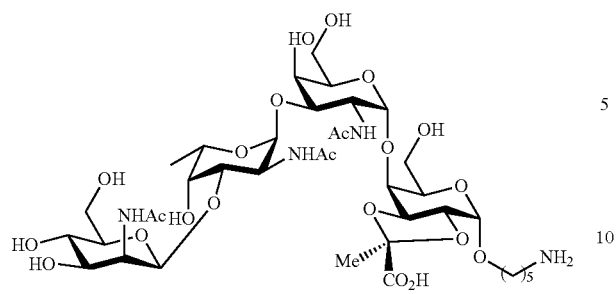
5-Amino-pentanyl 2-N-acetyl-2-deoxy-β-D-mann-opyranosyl-(1→3)-2-N-acetyl-2-deoxy-α-L-fucopy-ranosyl-(1→3)-2-N-acetyl-2-deoxy-α-D-galactopy-ranosyl-(1→4)-2,3-O-[1-(S)-(carboxy)-ethylidene]-α-D-galactopyranoside
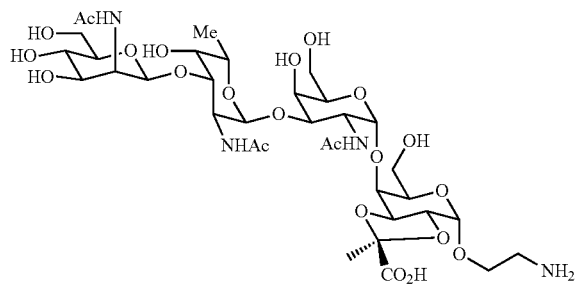
2-Aminoethyl 2-N-acetyl-2-deoxy-β-D-mannopyra-nosyl-(1→3)-2-N-acetyl-2-deoxy-α-L-fucopyrano-syl-(1→3)-2-N-acetyl-2-deoxy-α-D-galactopyrano-syl-(1→4)-2,3-O-[1-(S)-(carboxy)-ethylidene]-α-D-galactopyranoside
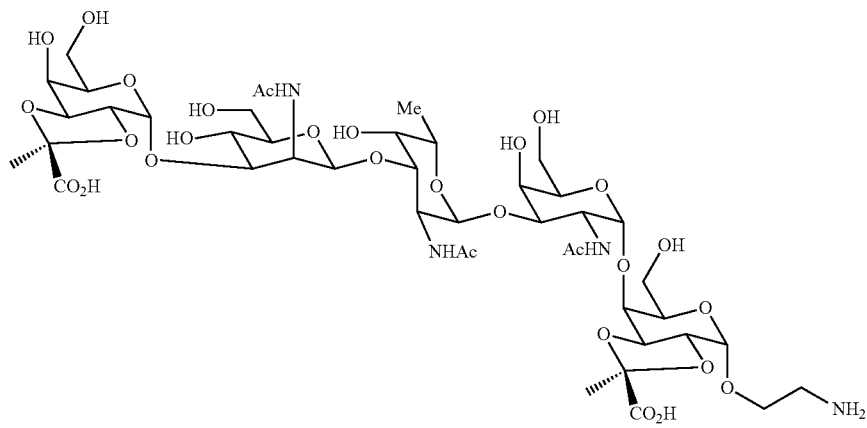

2-Aminoethyl 2,3-O-[1-(S)-(carboxy)-ethylidene]-α-
D-galactopyranosyl-(1→3)-2-N-acetyl-2-deoxy-β-
D-mannopyranosyl-(1→3)-2-N-acetyl-2-deoxy-α-L-
fucopyranosyl-(1→3)-2-N-acetyl-2-deoxy-α-D-
galactopyranosyl-(1→4)-2,3-O-[1-(S)-(carboxy)-
ethylidene]-α-D-galactopyranoside

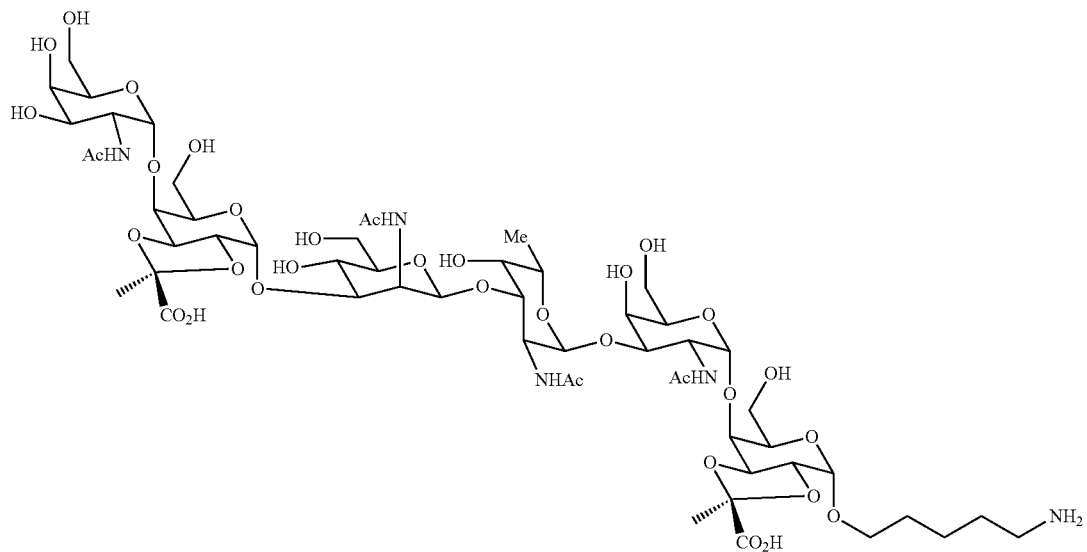

5-Aminopentanyl 2-N-acetyl-2-deoxy-α-D-galacto-
pyranosyl-(1→4)-2,3-O-[1-(S)-(carboxy)-ethyl-
idene]-α-D-galactopyranosyl-(1→3)-2-N-acetyl-2-
deoxy-β-D-manno-pyranosyl-(1→3)-2-N-acetyl-2-
deoxy-α-L-fucopyranosyl-(1→3)-2-N-acetyl-2-
deoxy-α-D-galactopyranosyl-(1→4)-2,3-O-[1-(S)-
(carboxy)-ethylidene]-α-D-galactopyranoside

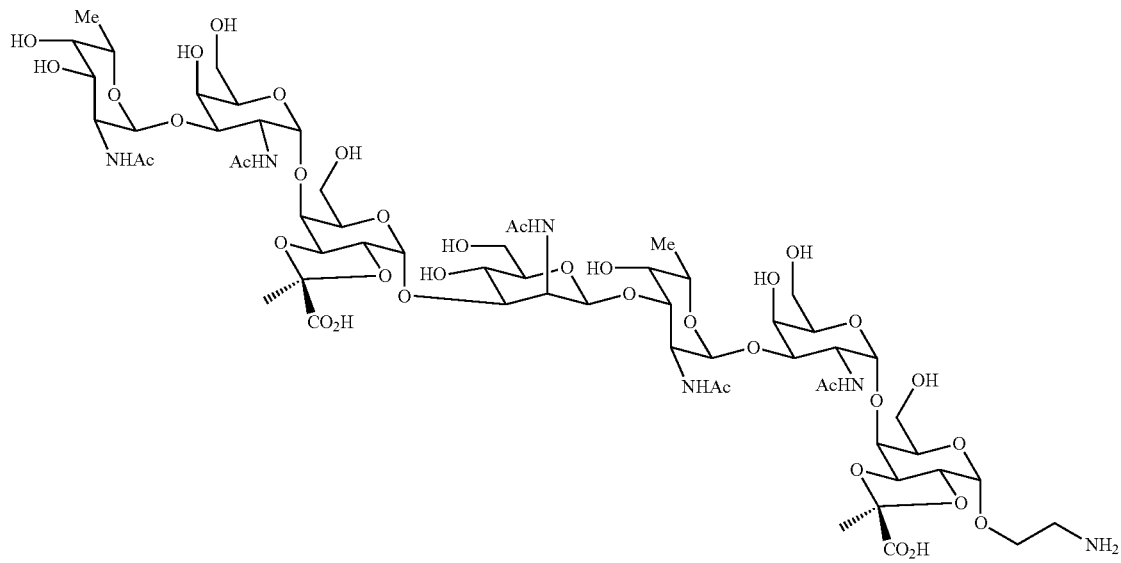

2-Aminoethyl 2-N-acetyl-2-deoxy-α-L-fucopyrano-
syl-(1→3)-2-N-acetyl-2-deoxy-α-D-galactopyrano-
syl-(1→4)-2,3-O-[1-(S)-(carboxy)-ethylidene]-α-D-
galactopyranosyl-(1→3)-2-N-acetyl-2-deoxy-β-D-
mannopyranosyl-(1→3)-2-N-acetyl-2-deoxy-α-L-
fucopyranosyl-(1→3)-2-N-acetyl-2-deoxy-α-D-
galactopyranosyl-(1→4)-2,3-O-[1-(S)-(carboxy)-
ethylidene]-α-D-galactopyranoside

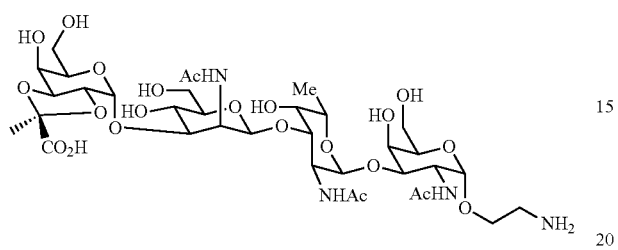

2-Aminoethyl 2,3-O-[1-(S)-(carboxy)-ethylidene]-α-
D-galactopyranosyl-(1→3)-2-N-acetyl-2-deoxy-β-
D-manno-pyranosyl-(1→3)-2-N-acetyl-2-deoxy-α-
L-fucopyranosyl-(1→3)-2-N-acetyl-2-deoxy-α-D-
galactopyranoside

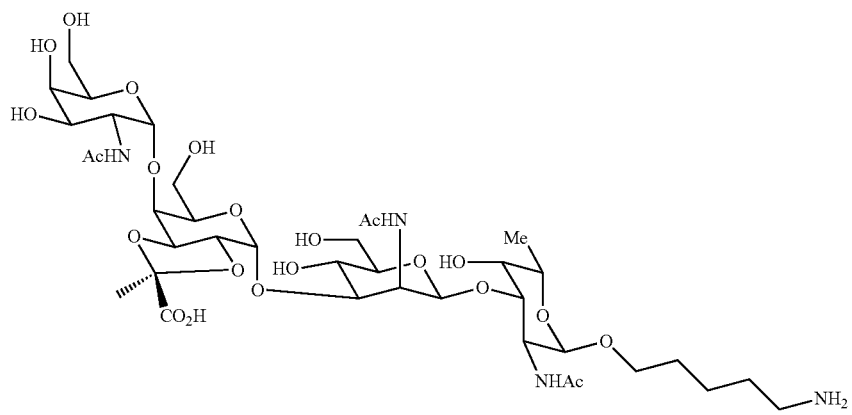

5-Aminopentanyl 2-N-acetyl-2-deoxy-α-D-galacto-
pyranosyl-(1→4)-2,3-O-[1-(S)-(carboxy)-ethyl-
idene]-α-D-galactopyranosyl-(1→3)-2-N-acetyl-2-
deoxy-β-D-manno-pyranosyl-(1→3)-2-N-acetyl-2-
deoxy-α-L-fucopyranoside

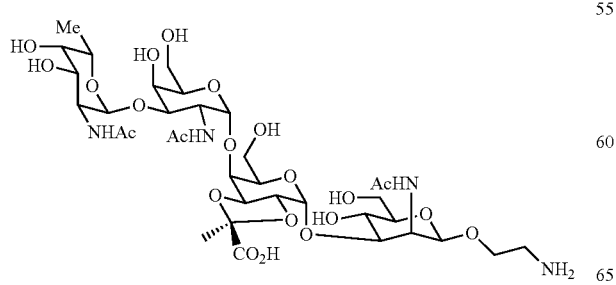

2-Aminoethyl 2-N-acetyl-2-deoxy-α-L-fucopyrano-
syl-(1→3)-2-N-acetyl-2-deoxy-α-D-galactopyrano-
syl-(1→4)-2,3-O-[1-(S)-(carboxy)-ethylidene]-α-D-
galactopyranosyl-(1→3)-2-N-acetyl-2-deoxy-β-D-
mannopyranoside

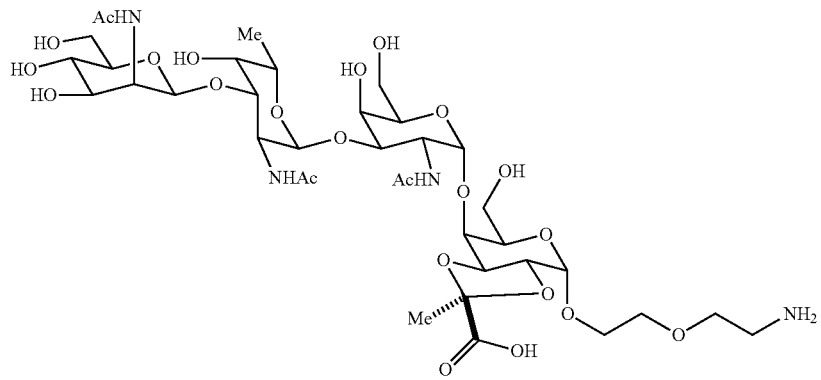

2-(2-Aminoethoxy)ethyl 2-N-acetyl-2-deoxy-β-D-
mannopyranosyl-(1→3)-2-N-acetyl-2-deoxy-α-L-
fucopyranosyl-(1→3)-2-N-acetyl-2-deoxy-α-D-ga-
lactopyranosyl-(1→4)-2,3-O-[1-(S)-(carboxy)-
ethylidene]-α-D-galactopyranoside 3-Amino-2,2-difluoropropyl 2-N-acetyl-2-deoxy-β-
D-mannopyranosyl-(1→3)-2-N-acetyl-2-deoxy-α-L-
fucopyranosyl-(1→3)-2-N-acetyl-2-deoxy-α-D-ga-
lactopyranosyl-(1→4)-2,3-O-[1-(S)-(carboxy)-
ethylidene]-α-D-galactopyranoside

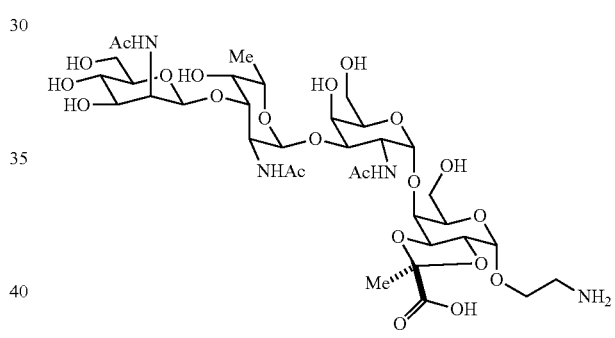

2-Aminoethyl 2-N-acetyl-2-deoxy-β-D-mannopyra-
nosyl-(1→3)-2-N-acetyl-2-deoxy-α-L-fucopyrano-
syl-(1→3)-2-N-acetyl-2-deoxy-α-D-galactopyrano-
syl-(1→4)-2,3-O-[1-(S)-(carboxy)-ethylidene]-α-D-
galactopyranoside

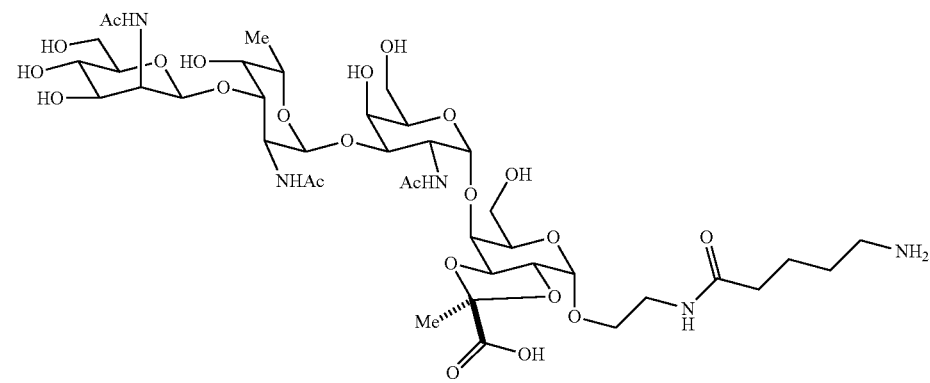

2-(5-Aminopentanoyl)-aminoethyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside

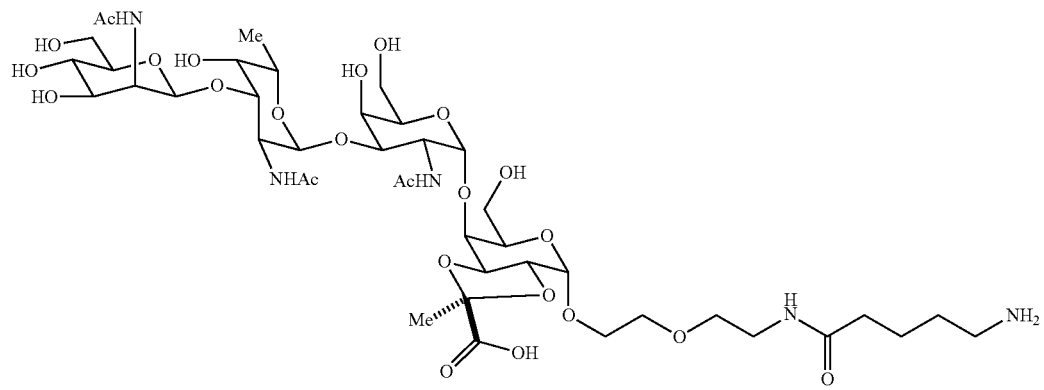

2-(2-(5-Aminopentanoyl)aminoethoxy)ethyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside

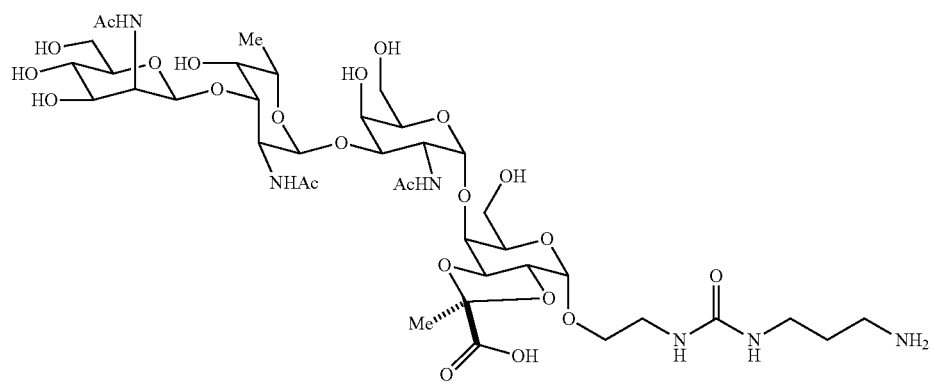

2-(3-Amino-1-aminocarbonyl)aminoethyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside

Chemical Synthesis

Another aspect of the present invention is directed to a method of synthesis of a saccharide of general formula (I)

$$V^*-[U_{x+3}-U_{x+2}-U_{x+1}-U_x]_n-V-O-L-NH_2 \quad (I)$$

wherein $x$ is an integer selected from 1, 2, 3 and 4;

$n$ is an integer selected from 1, 2 and 3:

$U_1 = U_5 = $ 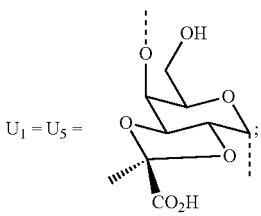

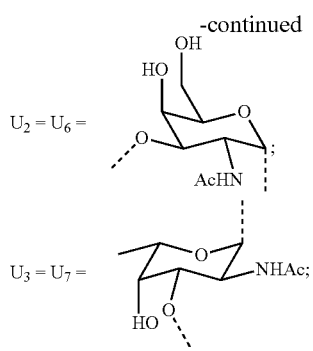
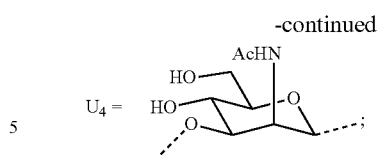
—V— represents a bond;
V*— represents H—;
L represents a linker;
comprising the following steps:
1. Providing a compound 1 of formula:
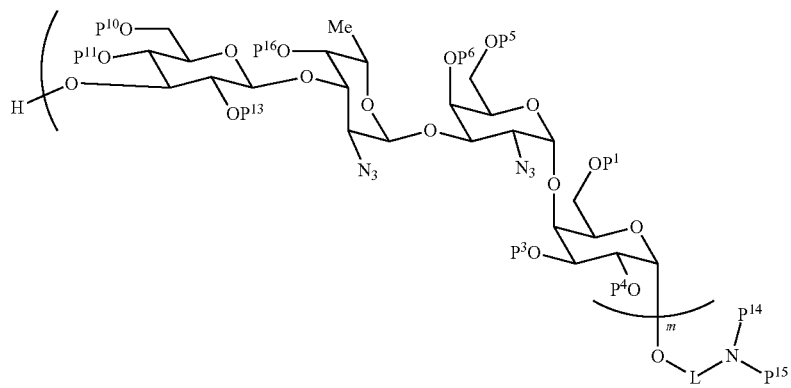
wherein $P^1$, $P^3$-$P^6$, $P^{10}$, $P^{11}$, $P^{13}$-$P^{16}$ represent protecting groups and m is an integer selected from 0, 1, 2;
and performing module a, module b, module c and module d to provide compound 2 of formula:
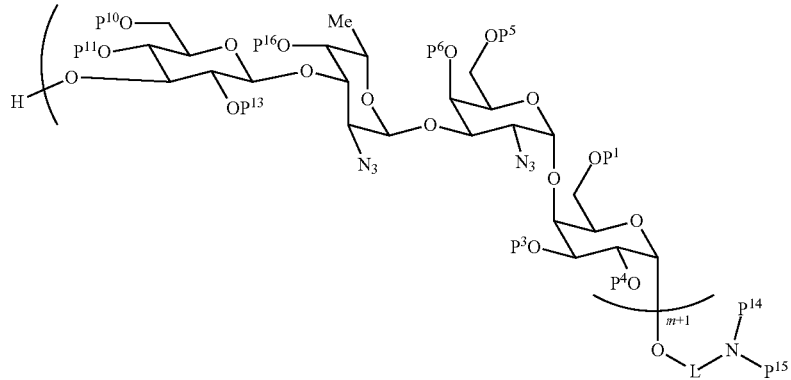

wherein $P^1$, $P^3$-$P^6$, $P^{10}$, $P^{11}$, $P^{13}$-$P^{16}$ represent protecting groups and m is an integer selected from 0, 1, 2; or 2. Providing a compound 3 of formula:

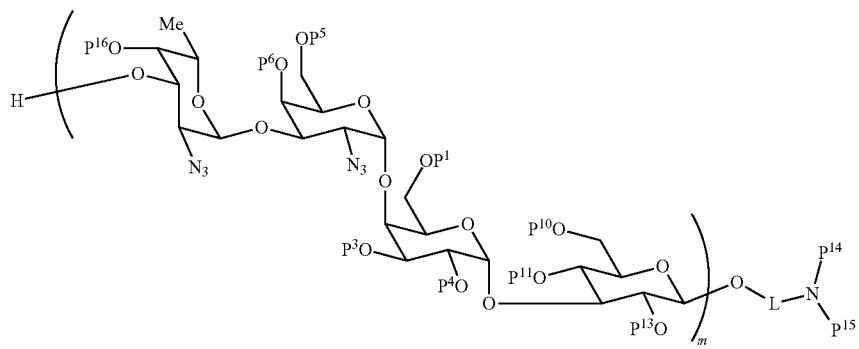

3 wherein $P^1$, $P^3$-$P^6$, $P^{10}$, $P^{11}$, $P^{13}$-$P^{16}$ represent protecting groups and m is an integer selected from 0, 1, 2; and performing module d, module a, module b and module c to provide compound 4 of formula:

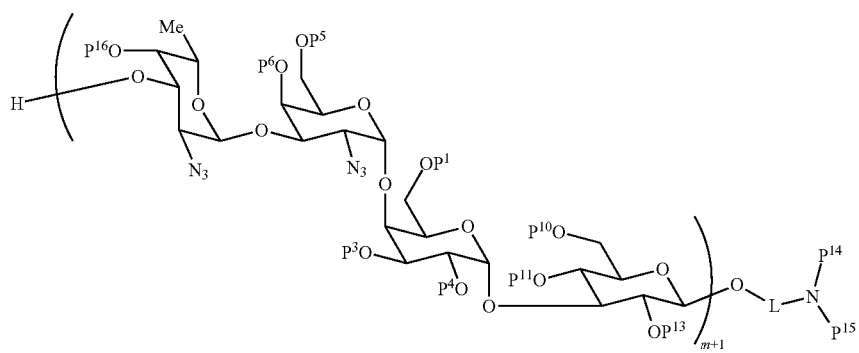

4 wherein $P^1$, $P^3$-$P^6$, $P^{10}$, $P^{11}$, $P^{13}$-$P^{16}$ represent protecting groups and m is an integer selected from 0, 1, 2; or 3. Providing a compound 5 of formula:

wherein $P^1$, $P^3$-$P^6$, $P^{10}$, $P^{11}$, $P^{13}$-$P^{16}$ represent protecting groups and m is an integer selected from 0, 1, 2;

and performing module c, module d, module a and module b to provide compound 6 of formula:

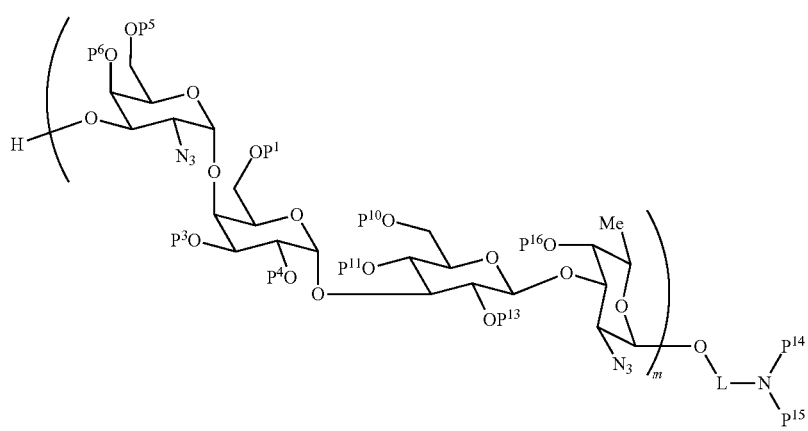

5

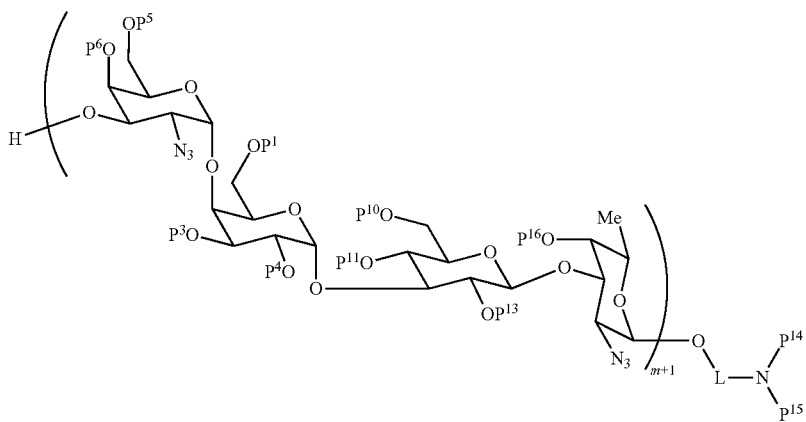

6 wherein $P^1$, $P^3$-$P^6$, $P^{10}$, $P^{11}$, $P^{13}$-$P^{16}$ represent protecting groups and m is an integer selected from 0, 1, 2;
or
4. Providing a compound 7 of formula:

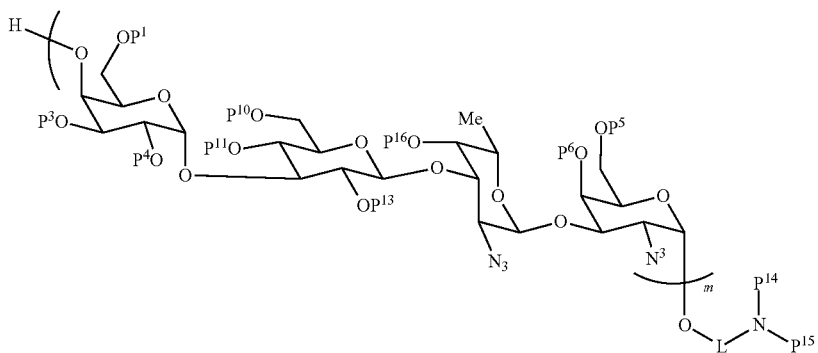

7 wherein $P^1$, $P^3$-$P^6$, $P^{10}$, $P^{11}$, $P^{13}$-$P^{16}$ represent protecting groups and m is an integer selected from 0, 1, 2;
and performing module b, module c, module d and module a to provide compound 8 of formula:

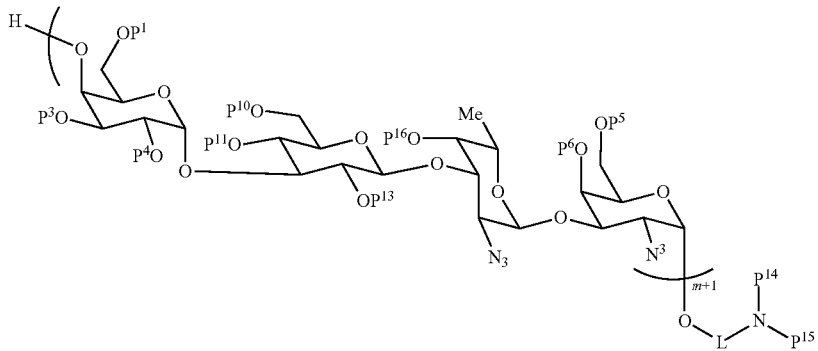

8 wherein $P^1$, $P^3$-$P^6$, $P^{10}$, $P^{11}$, $P^{13}$-$P^{16}$ represent protecting groups and m is an integer selected from 0, 1, 2;
and
5. Performing protection of the free OH group on compounds 2, 4, 6 and 8 to obtain compounds 9, 10, 11 and 12 of formulae:

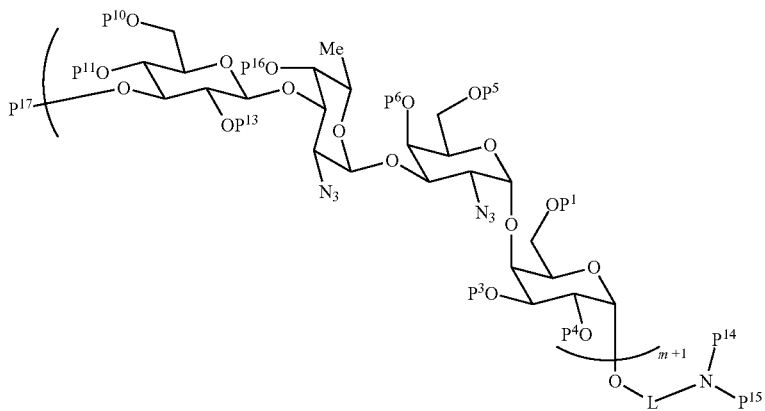
9
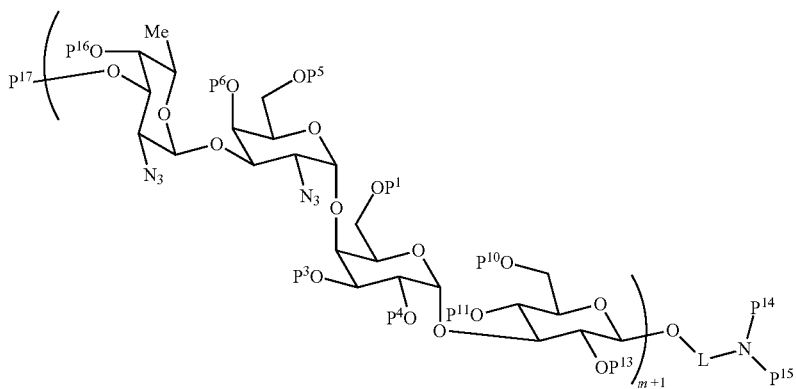
10
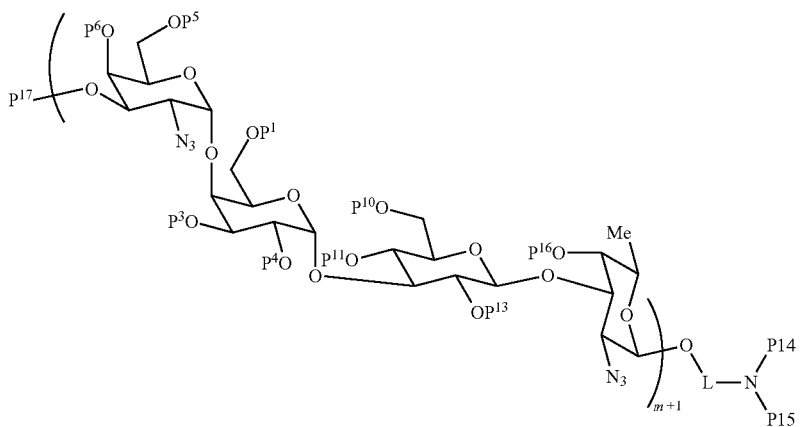
11
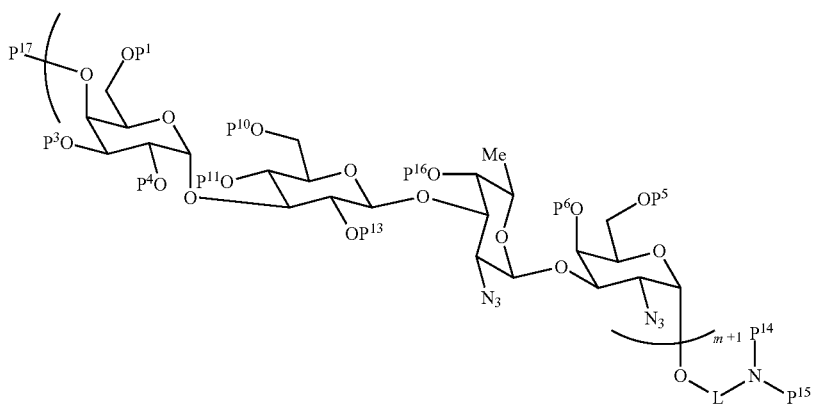
12 wherein $P^1$, $P^3$-$P^6$, $P^{10}$, $P^{11}$, $P^{13}$-$P^{17}$ represent protecting groups and m is an integer selected from 0, 1, 2; and
6. Performing module E on compounds 9, 10, 11 and 12 to afford compounds 13, 14, 15 and 16 of formulae:
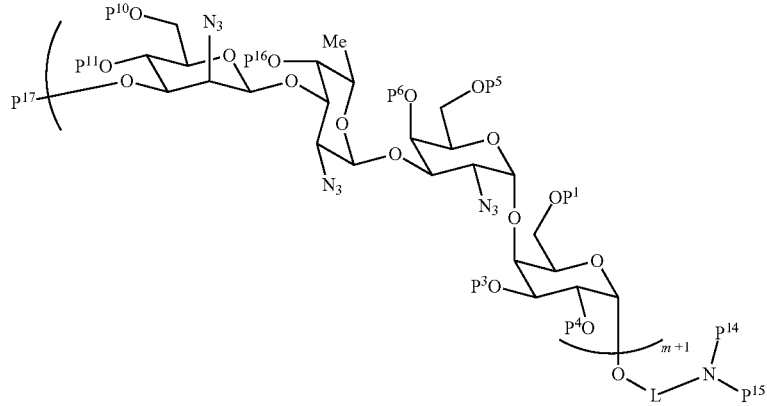
13
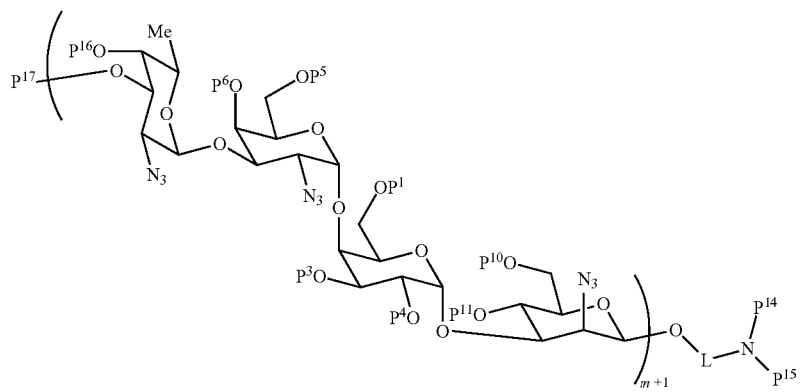
14
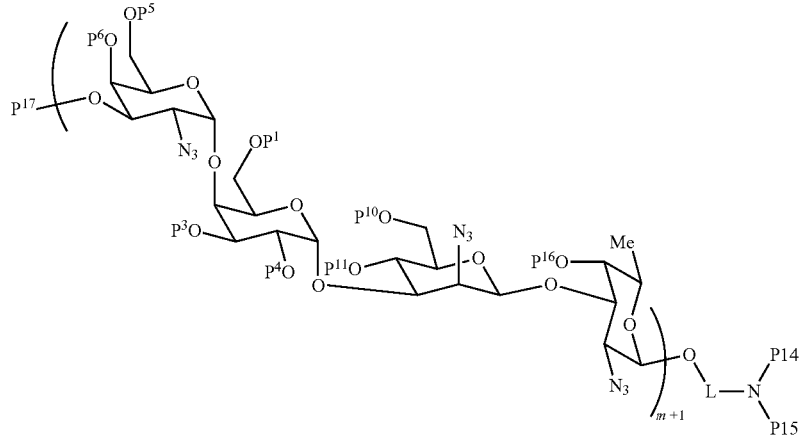
15

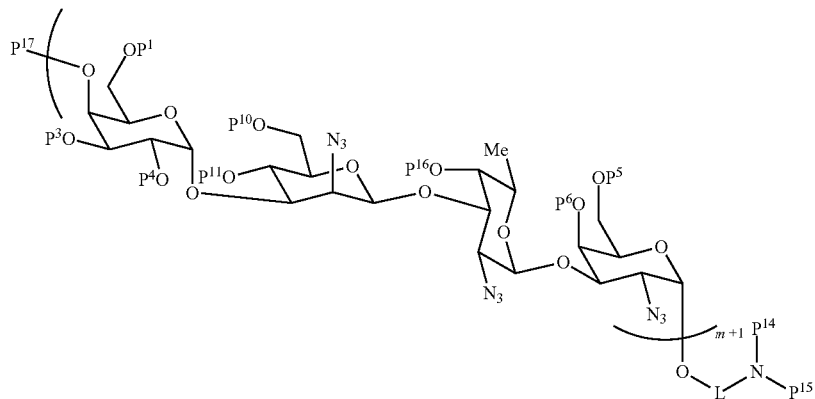
16
wherein $P^1$, $P^3$-$P^6$, $P^{10}$, $P^{11}$, $P^{14}$-$P^{17}$ represent protecting groups and m is an integer selected from 0, 1, 2;
and
7. Performing module F on compounds 13, 14, 15 and 16 to obtain compounds 17, 18, 19 and 20 of formulae:
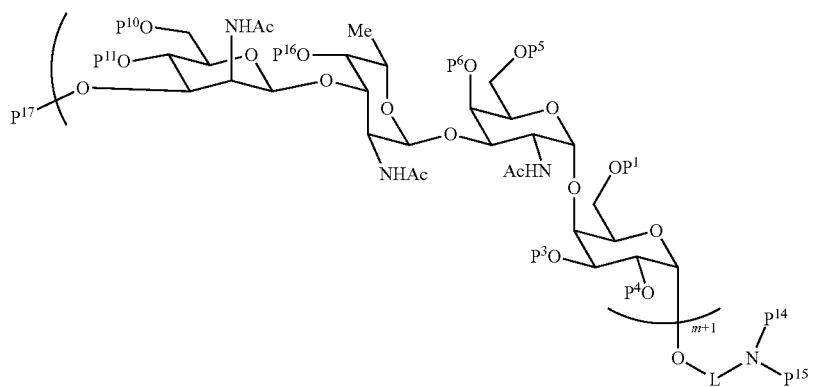
17
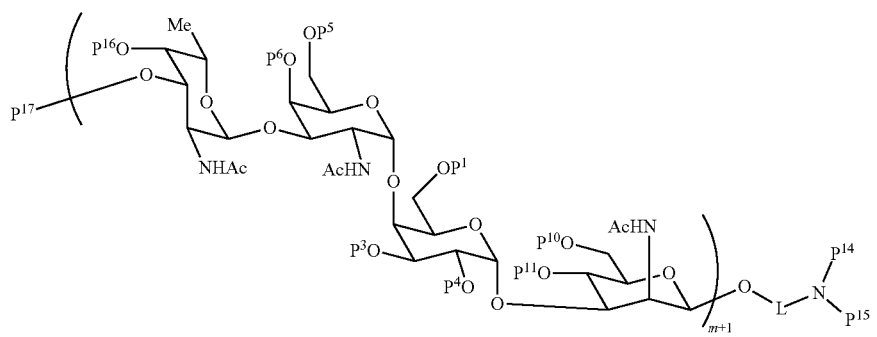
18

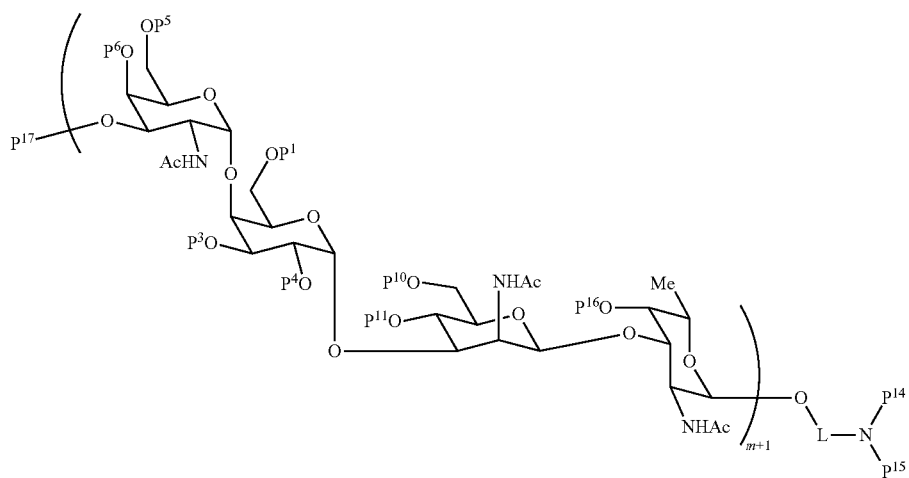
19
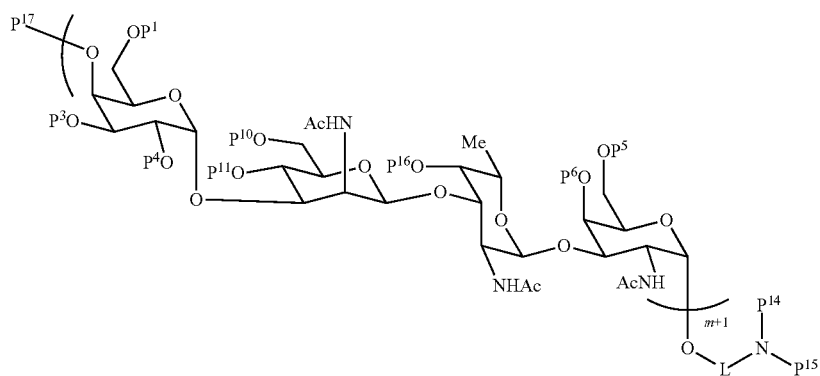
20
wherein $P^1$, $P^3$-$P^6$, $P^{10}$, $P^{11}$, $P^{14}$-$P^{17}$ represent protecting groups and m is an integer selected from 0, 1, 2;
and
8. Performing module G on compounds 17, 18, 19 and 20 in order to provide compounds 20, 21, 22 and 23 of formulae:
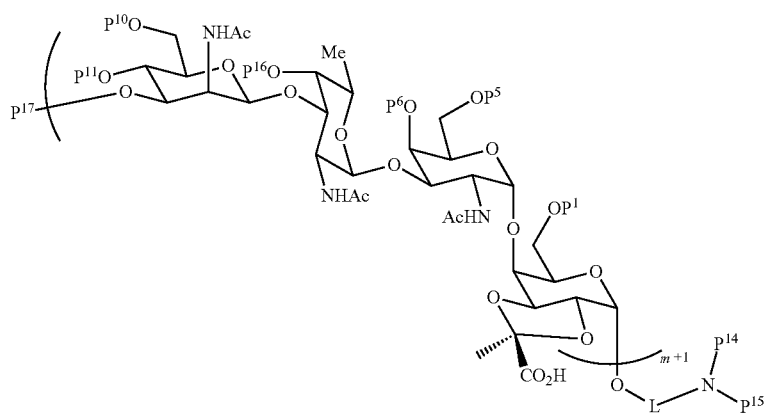
20

-continued

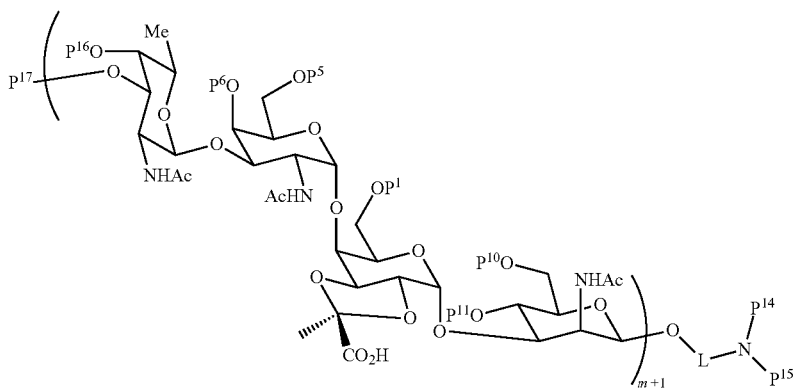
21

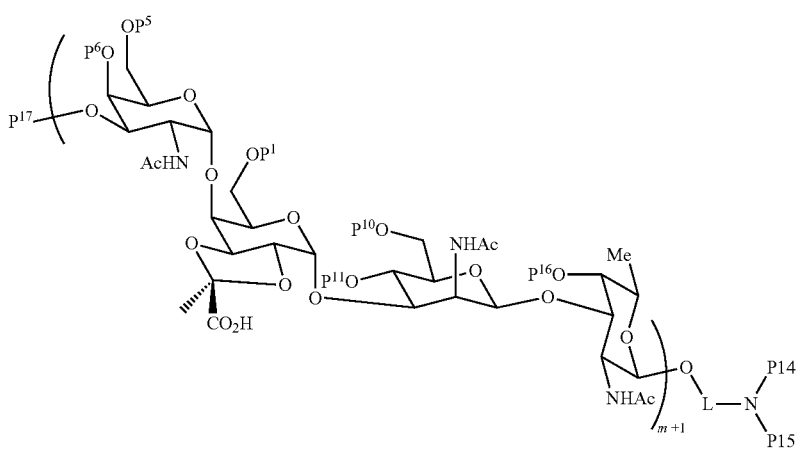
22

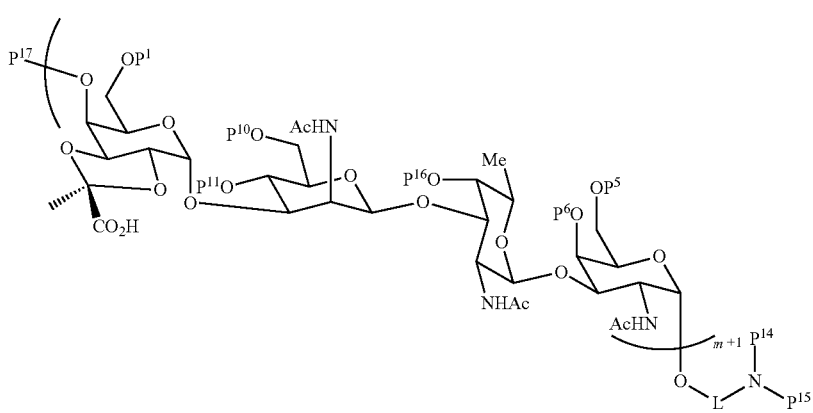
23 wherein $P^1$, $P^5$, $P^6$, $P^{10}$, $P^{11}$, $P^{14}$-$P^{17}$ represent protecting groups and m is an integer selected from 0, 1, 2; and 9. Removal of protecting groups $P^1$, $P^5$, $P^6$, $P^{10}$, $P^{11}$, $P^{14}$-$P^{17}$ on compounds 20, 21, 22 and 23 to provide the compounds of general formula (I), wherein
—V— represents a bond;
V*— represents H—;
and L represents a linker;
wherein
module A consists of:
A1. treatment with glycosylating agent $GA^1$ in presence of an activating agent, wherein $GA^1$ is of general formula:

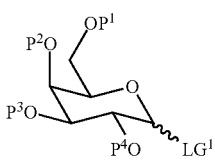
$GA^1$ and wherein $P^1$-$P^4$ represent protecting groups and $LG^1$ represents a leaving group, and A2. performing removal of protecting group $P^2$.

module B consists of:

B1. treatment with glycosylating agent $GA^2$ in presence of an activating agent, wherein $GA^2$ is of general formula:

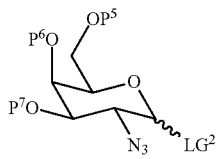

GA² and wherein $P^5$-$P^7$ represent protecting groups and $LG^2$ represents a leaving group;

and

B2. performing removal of protecting group $P^7$.

module C consists of:

C1. treatment with glycosylating agent $GA^3$ in presence of an activating agent, wherein $GA^3$ is of general formula:

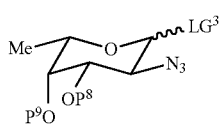

GA³ and wherein $P^8$ and $P^9$ represent protecting groups and $LG^3$ represents a leaving group;

and

C2. performing removal of protecting groups $P^8$ and $P^9$ and installing protecting group $P^{16}$ on the axial OH.

module D consists of:

D1. treatment with glycosylating agent $GA^4$ in presence of an activating agent, wherein $GA^4$ is of general formula:

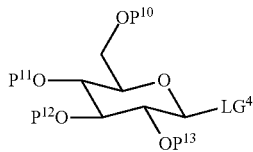

GA⁴ and wherein $P^{10}$-$P^{13}$ represent protecting groups and $LG^4$ represents a leaving group;

and

D2. performing removal of protecting group $P^{12}$.

module E consists of

E1. removal of protecting group $P^{13}$ to provide an intermediate —OH group, and E2. conversion of the intermediate —OH group obtained at step E1 to a leaving group -$LG^5$;

and

E3. nucleophilic substitution of the a leaving group -$LG^5$ by an azido group —$N_3$ with inversion of configuration.

module F consists of reduction of the azido group to the corresponding acetamido group.

module G consists of

G1. removal of the protecting groups $P^3$ and $P^4$ to provide an intermediate diol;

and

G2. installation of a (S)-pyruvate moiety on the intermediate diol obtained at step G1.

$P^1$, $P^2$, $P^3$, $P^4$, $P^5$, $P^6$, $P^7$, $P^8$, $P^9$, $P^{10}$, $P^{11}$, $P^{12}$, $P^{13}$, $P^{14}$, $P^{15}$, $P^{16}$ and $P^{17}$ represent protecting groups. The term "protecting group" as used herein refers to commonly used groups in organic synthesis, preferably used for protection of amines, hydroxyl groups, thiols, imines, carbonyls, carboxyls or other common functional groups, and particularly preferred for amines and hydroxyl groups.

More specifically, $P^1$, $P^2$, $P^3$, $P^4$, $P^5$, $P^6$, $P^7$, $P^8$, P9, $P^{10}$, $P^{11}$, $P^{12}$, $P^{13}$, $P^{16}$ and $P^{17}$ represent protecting groups for hydroxyl groups, more preferably different suitable protecting groups for hydroxyl groups capable of being removed subsequently one after another by a suitable sequence of deprotection reactions. Known protecting groups for hydroxyl groups include, but are not limited to acetyl, benzyl, benzylidene, benzoyl, p-methoxybenzyl, p-methoxybenzylidene, p-methoxyphenyl, para-bromobenzyl, p-nitrophenyl, allyl, acetyl, isopropyl, levulinyl, dimethoxytrityl, trityl, 2-naphthylmethyl, pyvaloyl, triisopropylsilyl, tert-butyldimethylsilyl, tert-butyldiphenylsilyl, tert-butylmethoxphenylsilyl, triethylsilyl, trimethylsilyl, 2-trimethylsilylethoxymethyl.

$P^{14}$ and $P^{15}$ represent protecting groups for amines and may be selected from the group consisting of or comprising tert-butyloxy carbonyl, 9-fluorenylmethoxy carbonyl, allyloxy carbonyl, 2,2,2-trichloroethyloxy carbonyl, benzyloxy carbonyl; carbonyls such as trifluoro acetyl, trichloro acetyl, acetyl, or benzoyl and aromatic alkyl such as benzyl, p-methoxybenzyl, p-methoxyphenyl, para-bromobenzyl, p-nitrophenyl, or 2-naphthylmethyl.

The protecting groups can be differentiated in permanent protecting groups and temporary protecting groups. Permanent protecting groups are protecting groups that are stable during the entire synthesis and that can be efficiently removed at the late stage of the synthesis. In this case, permanent protecting groups include $P^1$, $P^5$, $P^6$, $P^{10}$, $P^{11}$, $P^{14}$, $P^{15}$, $P^{16}$ and $P^{17}$. $P^1$, $P^5$, $P^6$, $P^{10}$, $P^{11}$, $P^{16}$, and $P^{17}$ are masking the hydroxyl groups during the entire synthesis, while protecting groups $P^{14}$ and $P^{15}$ are masking the terminal amino group present on the linker L. Preferably protecting group $P^1$ is a benzyl group, protecting groups $P^5$ and $P^6$ form together a benzylidene protecting group or are benzyl groups, protecting groups $P^{10}$ and $P^{11}$ form together a benzylidene group or are benzyl groups, protecting group $P^{16}$ is a benzoyl, a benzyl or an acetyl group, and preferably a benzoyl or benzyl group, protecting group $P^{14}$ is a benzyl group and protecting group $P^{15}$ is a benzyloxycarbonyl group (Cbz).

The temporary protecting groups are generally orthogonal protecting groups that can be selectively removed at different levels of the synthesis to free hydroxyl groups for subsequent introduction of different substituents, including monosaccharides, other protecting groups or other residues present on the molecule. In this case, temporary protecting groups include $P^2$, $P^3$, $P^4$, $P^7$, $P^8$, $P^8$, $P^9$, $P^{12}$, and $P^{13}$.

The ingenious choice of protecting groups allows expedient access to a library of saccharides of general formula I functionalized with an amino group for subsequent conjugation to an immunogenic carrier or a solid support.

Preferably, temporary protecting groups $P^2$, $P^7$, $P^8$ and $P^9$ are directing protecting groups that favor the formation of a glycosidic linkage. Examples of directing protecting groups are acetyl, benzoyl and levulinoyl groups. Preferably, $P^2$, $P^7$, $P^8$ and $P^9$ are acetyl groups.

Temporary protecting groups $P^3$, $P^4$ and $P^{12}$ are not-participating groups such as ethers and silyl ethers. Examples of suitable ethers and silyl ethers include, but are not restricted to: allyl, p-methoxybenzyl, 2-naphthylmethyl, tri-isopropylsilyl, tert-butyldimethylsilyl, tert-butylmethoxyphenylsilyl, triethylsilyl, trimethylsilyl, 2-trimethylsilylethoxymethyl. Preferably, protecting group $P^{12}$ can be selectively removed in presence of $P^3$ and $P^4$. Preferably, $P^3$ and $P^4$ are selected from the group consisting of allyl, p-methoxybenzyl, 2-naphthylmethyl, triisopropylsilyl, tert-butyldimethylsilyl, triethylsilyl, trimethylsilyl and more preferably $P^3$ and $P^4$ are the same. In a preferred embodiment, protecting group $P^{12}$ represents allyl or p-methoxybenzyl and protecting groups $P^3$ and $P^4$ represent 2-naphthylmethyl or silyl ether. In another preferred embodiment, protecting group $P^{12}$ is a silyl ether and $P^3$ and $P^4$ are selected from the groups consisting of allyl, p-methoxybenzyl and 2-naphthylmethyl.

Temporary protecting group $P^{13}$ is a participating protecting group favoring the formation of the β linkage. Preferably protecting group $P^{13}$ shall be selectively removed in presence of protecting groups $P^3$, $P^4$ and $P^{12}$. Preferably, protecting group $P^{13}$ is levulinoyl.

Building blocks $GA^1$, $GA^2$, $GA^3$ and $GA^4$ are glycosylating agents. As used herein, the term glycosylating agent refers to a monosaccharide functionalized at the anomeric position with a leaving group that upon activation with a suitable activating agent provide an oxocarbenium intermediate able to react with a nucleophile, such as a hydroxyl group. Hence, glycosylating agents $GA^1$, $GA^2$, $GA^3$ and $GA^4$ are functionalized at the anomeric position with leaving groups $LG^1$, $LG^2$, $LG^3$ and $LG^4$. Examples of leaving groups suitable for the present synthesis are well known to the person skilled in carbohydrate chemistry and include halides, thioethers, imidates, acetate, and phosphate.

Preferably, leaving groups $LG^1$, $LG^2$, $LG^3$ and $LG^4$ are selected from the group of leaving groups consisting of:

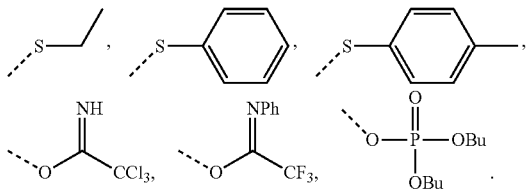

As mentioned, the provision of an oxocarbenium intermediate relies on the activation of the leaving group installed at the anomeric position of the glycosylating agent with an appropriate or suitable activating agent. It is common knowledge for the skilled person that suitable activating agents for phosphate (i.e. phosphate activating agents) and imidate (i.e. imidate activating agents) are Lewis acids, such as silyl triflate or silver triflate, while suitable activating agents for thioether i.e. thioether activating agents include, but are not restricted to: NIS/TfOH, NIS/TMSOTf, NIS/BF$_3$.Et$_2$O, NIS/AgOTf, DMTST/Tf$_2$O, IDPC, BSP/Tf$_2$O, Ph$_2$SO/Tf$_2$O. Examples of silyl triflate include, but are not restricted to trimethylsilyl trifluoromethanesulfonate, tert-butyl dimethyl trifluoromethanesulfonate, triiospropyl trifluoromethanesulfonate.

Preferably, $LG^1$ and $LG^4$ are thioethers and $LG^2$ and $LG^3$ are imidates, and more preferably $LG^1$ and $LG^4$ are ethyl-thioethers and $LG^2$ and $LG^3$ are trichloroacetimidates.

Leaving group $LG^5$ installed at step E2 can be selected from the group comprising chloride, bromide, iodide, tosylate, benzensulfonate, p-nitro-benzenesulfonate, mesylate or triflate group. Preferably, the leaving group LG5 is an ester of a sulfonic acid (i.e. a sulfonate), and more preferably $LG^5$ is a triflate group.

In a preferred embodiment according to the present invention module A consists of A1. treatment with glycosylating agent $GA^{1*}$ in presence of a thioether activating agent in a mixture of apolar solvent and polar aprotic solvent, wherein $GA^1$ is of general formula:

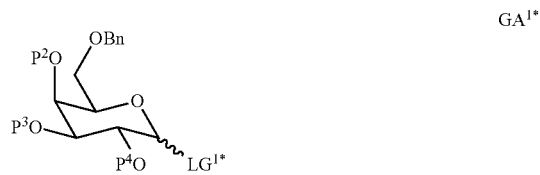

and wherein $P^2$-$P^4$ represent protecting groups and $LG^{1*}$ represents a leaving group selected from the group consisting of:

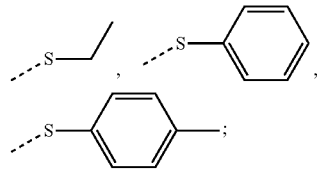

and

A2. performing removal of protecting group $P^2$ with MeONa/MeOH;

module B consists of

B1. treatment with glycosylating agent $GA^{2*}$ in presence of an imidate activating agent in a mixture of apolar solvent and polar aprotic solvent, wherein $GA^{2*}$ is of general formula

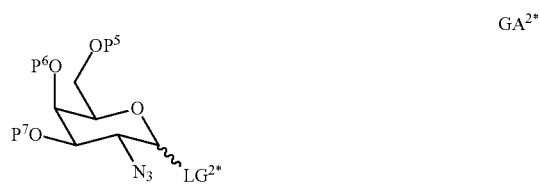

and wherein $P^5$-$P^7$ represent protecting groups and $LG^{2*}$ represents a leaving group selected from the group consisting of:

and

B2. performing removal of protecting group P⁷ with MeONa/MeOH;

module C consists of

C1. treatment with glycosylating agent GA³* in presence of an imidate activating agent in an apolar solvent, wherein GA³* is of general formula

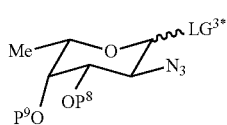

and wherein P⁸ and P⁹ represent protecting groups and LG³ represents a leaving group selected from the group consisting of:

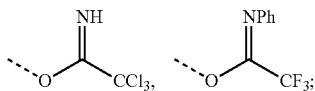

and

C2. performing removal of protecting groups P⁸ and P⁹ with NaOMe/MeOH and installing protecting group P¹⁶ on the axial OH.

module D consists of

D1. treatment with glycosylating agent GA⁴* in presence of an thioether activating agent in an apolar solvent, wherein GA⁴* is of general formula

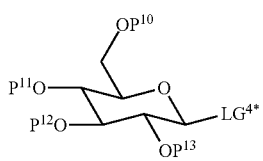

and wherein P¹⁰-P¹³ represent protecting groups and LG⁴ represents a leaving group selected from the group consisting of:

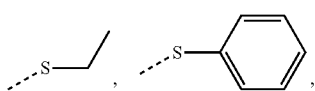

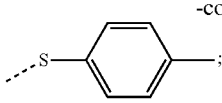

and

D2. performing removal of protecting group PG¹².

Preferred polar aprotic solvents are tetrahydrofuran, diethyl ether and dioxane. Preferred apolar solvents are toluene, halogenated solvents such as chloroform and methylene chloride. Preferred mixtures of apolar and polar aprotic solvent are: methylene chloride/tetrahydrofuran, methylene chloride/diethyl ether, toluene/diethyl ether, toluene/tetrahydrofuran.

Preferably module E consists of

E1. removal of protecting group PG¹³ to provide an intermediate —OH group with hydrazine or a hydrazinium salt in a solvent or mixture of solvents, and E2. conversion of the intermediate —OH group obtained at step E1 to a leaving group -LG⁵;

and

E3. nucleophilic substitution of the a leaving group -LG⁵ by an azido group —N₃ with inversion of configuration.

At step E1 hydrazinium salts of weak acids such as hydrazinium acetate or hydrazinium propionate are preferred. Suitable solvents for this reaction are apolar solvents, such as methylene chloride and toluene, polar solvents such as pyridine, acetic acid and methanol, and mixtures thereof.

Preferably, the reduction of the azido group to the corresponding acetamido group performed in module F is performed by treatment with thioacetic acid in pyridine. An alternative method is to conduct conversion of the azido group in the acetamido group in two steps: first chemoselective reduction of the azido group, and then acetylation. The chemoselective reduction can be carried out via Staudinger reaction (PPh₃ or PMe₃, THF/H₂O) or by hydrogenolysis on Pd/C in presence of ammonia, ammonium acetate, triphenylphosphine or pyridine. The acetylation can be accomplished using acetyl chloride or acetic anhydride in presence of a base.

Preferably module G consists of

G1. removal of the protecting groups PG³ and PG⁴ with DDQ (2,3-dichloro-5,6-dicyano-1,4-benzoquinone) in a mixture of solvents to provide an intermediate diol;

and

G2. installation of a (S)-pyruvate moiety on the intermediate diol obtained at step G1.

Preferably the installation of (S)-pyruvate moiety at step G2 is performed using 2,2-bis(ethylthio)propanoate, TTBMP (2,4,6-tri-tert-butylpyridine) and DMTST (dimethyl(methylthio)sulfonium trifluoromethanesulfonate) in an apolar solvent.

Another aspect of the present invention is directed to a method of synthesis of a saccharide of general formula (II-a)

(II-a)

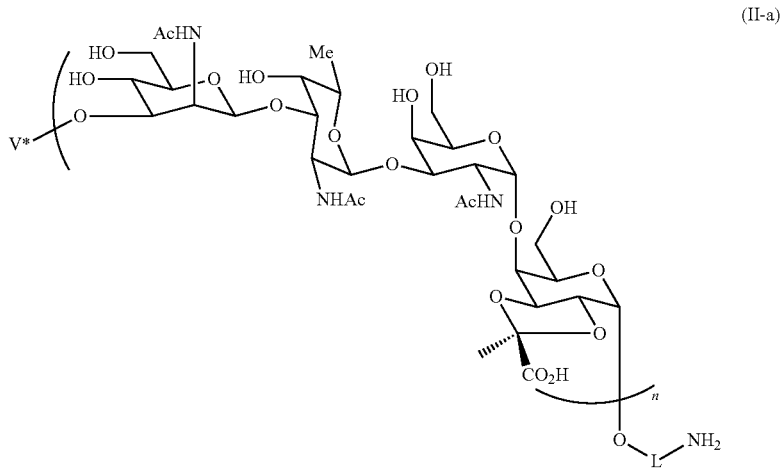

wherein
n represents 1, V*— represents H— and L represents a linker i.e. a compound of general formula VI (VI)

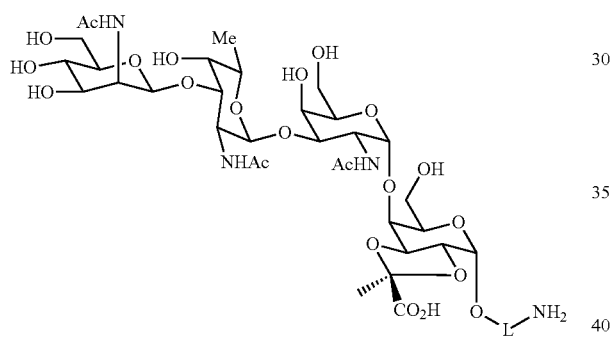

comprising the following steps:
1.1 reacting a compound 24 of formula:

24

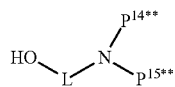

wherein $P^{14}$ and $P^{15}$ represent protecting groups and L has the meaning defined herein, with a compound 25 of formula:

25

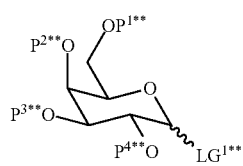

wherein $P^{1}$-$P^{4}$ represent protecting groups and $LG^{1**}$ represents a leaving group selected from the group consisting of:

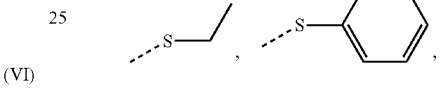

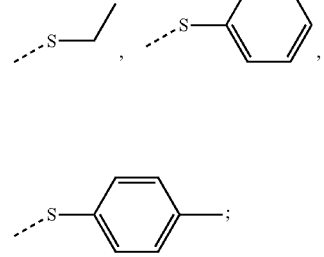

to afford compound 26 of formula:

26

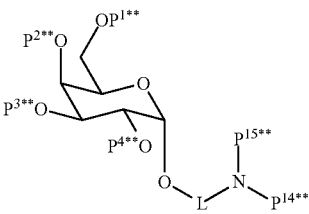

and
1.2 performing removal of protecting group $P^{2**}$ on compound 26 to afford compound 27

27

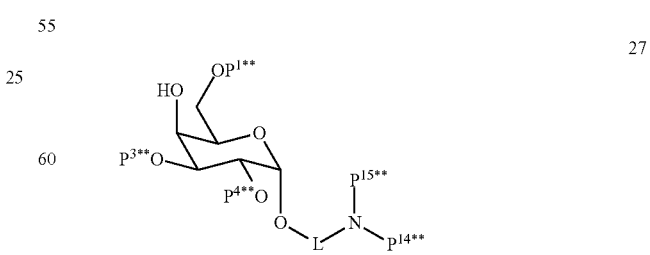

wherein $P^{1}$, $P^{3}$, $P^{4}$, $P^{14}$ and $P^{15**}$ represent protecting groups and L has the meaning defined herein;

and 2.1 reacting compound 27 with compound 28 of formula:

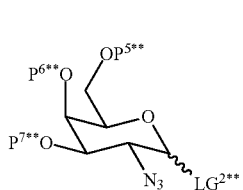

28 wherein $P^{5}$-$P^{7}$ represent protecting groups and $LG^{2**}$ represents a leaving group selected from the group consisting of:

to afford compound 29 of formula:

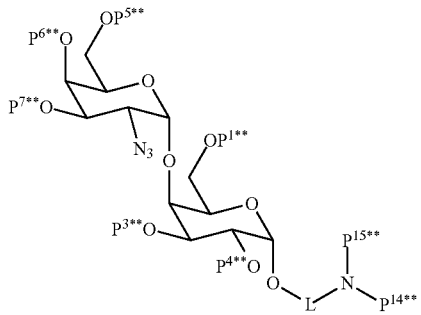

29 wherein $P^{1}$, $P^{3}$-$P^{7}$, $P^{14}$, $P^{15**}$ represent protecting groups and L has the meaning defined herein;

and 2.2 performing removal of protecting group $P^{7**}$ on compound 29 to afford compound 30

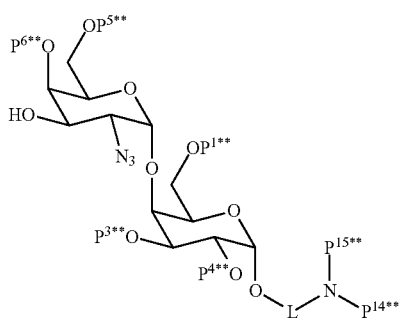

30 wherein $P^{1}$, $P^{3}$-$P^{7}$, $P^{14}$, $P^{15**}$ represent protecting groups and L has the meaning defined herein;

and 3.1 reacting compound 30 with compound 31 of formula:

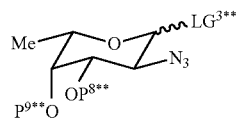

31 wherein $P^{8}$-$P^{9}$ represent protecting groups and $LG^{3**}$ represents a leaving group selected from the group consisting of:

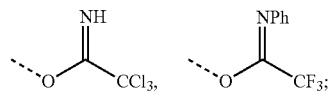

to afford compound 32

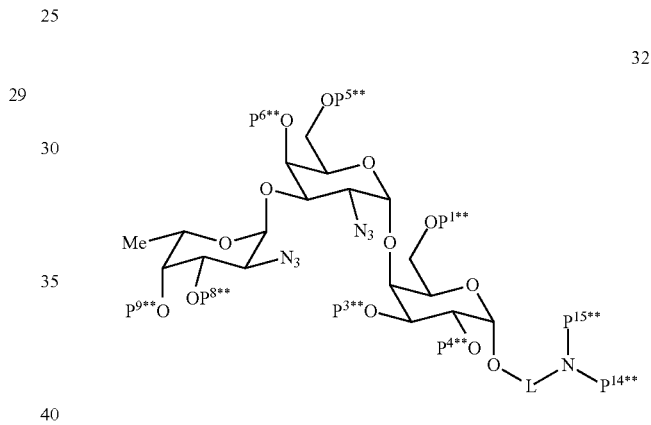

32 wherein $P^{1}$, $P^{3}$-$P^{6}$, $P^{8}$, $P^{9}$, $P^{14}$ and $P^{15**}$ represent protecting groups and L has the meaning defined herein;

and 3.2 performing removal of protecting groups $P^{8}$ and $P^{9}$ on compound 32 to afford compound 33

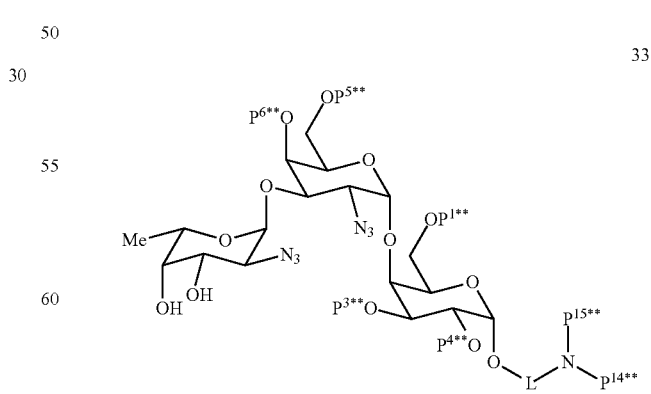

33 wherein $P^{1}$, $P^{3}$-$P^{6}$, $P^{14}$ and $P^{15**}$ represent protecting groups and L has the meaning defined herein;

and 3.3 installing protecting group $P^{16**}$ on compound 33 to afford compound 34

34

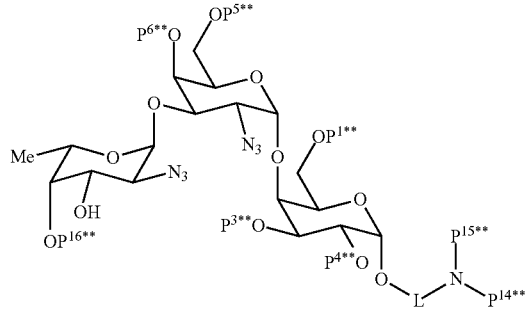

wherein $P^{1}$, $P^{3}$-$P^{6}$, $P^{14}$-$P^{16**}$ represent protecting groups and L has the meaning defined herein;

and 4.1 reacting compound 34 with compound 35 of formula

35

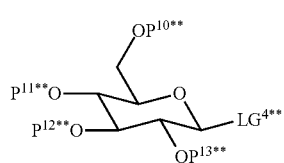

wherein $P^{10}$-$P^{13}$ represent protecting groups and $LG^{4**}$ represents a leaving group selected from the group consisting of:

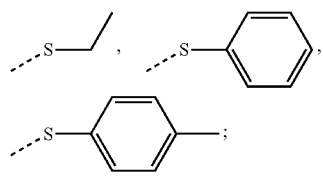

to afford compound 36

36

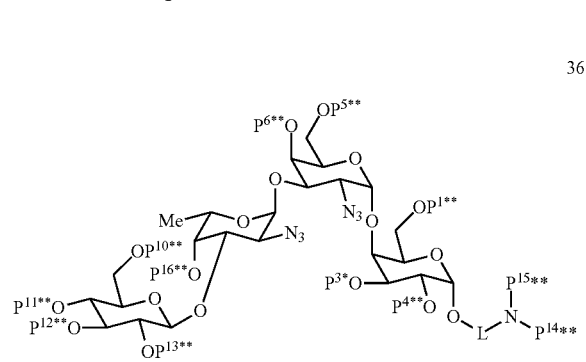

wherein $P^{1}$, $P^{3}$-$P^{6}$, $P^{10}$-$P^{16**}$ represent protecting groups and L has the meaning defined herein;

and 4.2 converting compound 36 to compound 37 of formula

37

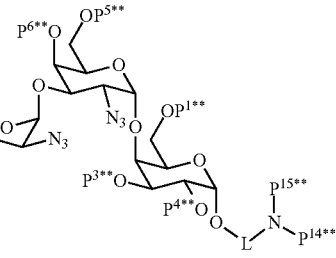

wherein $P^{1}$, $P^{3}$-$P^{6}$, $P^{10}$-$P^{12}$, $P^{14}$-$P^{16**}$ represent protecting groups and L has the meaning defined herein;

and 4.3 converting the azido groups on compound 37 to the corresponding acetamido groups to afford compound 38

38

(structure)

wherein $P^{1}$, $P^{3}$-$P^{6}$, $P^{10}$-$P^{12}$, $P^{14}$-$P^{16**}$ represent protecting groups and L has the meaning defined herein;

and 4.4 converting the azido groups on compound 37 to the corresponding acetamido groups to afford compound 38

38

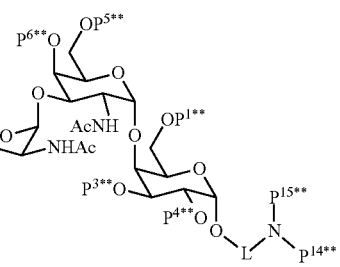

wherein $P^{1}$, $P^{3}$-$P^{6}$, $P^{10}$-$P^{12}$, $P^{14}$-$P^{16**}$ represent protecting groups and L has the meaning defined herein;

and 4.5 performing selective removal of protecting groups $P^{3}$ and $P^{4}$ on compound 38 to afford diol 39

39

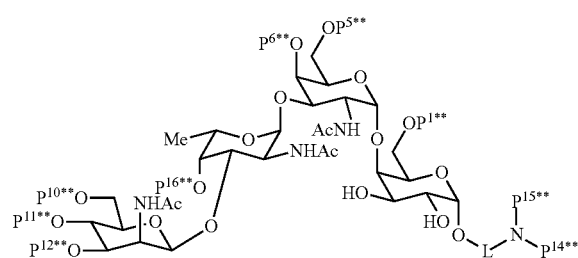

wherein $P^{1}$, $P^{5}$, $P^{6}$, $P^{10}$-$P^{12}$, $P^{14}$-$P^{16**}$ represent protecting groups and L has the meaning defined herein; and 4.7 installation of the (S)-pyruvate moiety on the diol 39 to provide compound 40

40

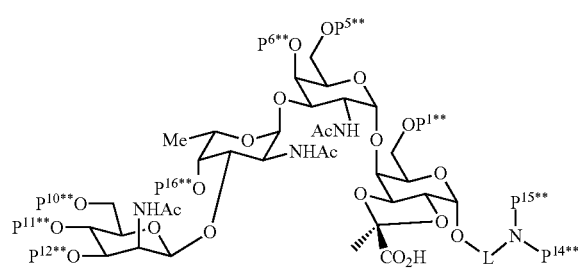

wherein $P^{1}$, $P^{5}$, $P^{6}$, $P^{10}$-$P^{12}$, $P^{14}$-$P^{16}$ represent protecting groups and L has the meaning defined herein; and 4.8 performing removal of protecting groups $P^{1}$, $P^{5}$, $P^{6}$, $P^{10}$-$P^{12}$, $P^{14}$-$P^{16}$ on compound 40 to afford compound VI.

$P^{1}$, $P^{2}$, $P^{3}$, $P^{4}$, $P^{5}$, $P^{6}$, $P^{7}$, $P^{8}$, $P^{9}$, $P^{10}$, $P^{11}$, $P^{12}$, $P^{13}$, $P^{14}$, $P^{15}$ and $P^{16}$, represent protecting groups.

Preferably protecting groups $P^{1}$ and $P^{12}$ are benzyl groups, protecting groups $P^{5}$ and $P^{6}$ form together a benzylidene protecting group or are benzyl groups, protecting groups $P^{10}$ and $P^{11}$ form together a benzylidene group or are benzyl groups, protecting group $P^{16}$ is an acetyl group, protecting group $P^{14}$ is a benzyl group and protecting group $P^{15**}$ is a benzyloxycarbonyl group (Cbz).

Preferably, temporary protecting groups $P^{2}$, $P^{7}$, $P^{8}$ and $P^{9}$ are selected from acetyl, benzoyl and levulinoyl groups. Even more preferably, $P^{7}$, $P^{8}$ and $P^{9}$ are acetyl groups and $P^{2}$ is a benzoyl group.

Preferably, $P^{3}$ and $P^{4}$ are selected from the group consisting of allyl, p-methoxybenzyl, 2-naphthylmethyl, tri-isopropylsilyl, tert-butyldimethylsilyl, triethylsilyl, trimethylsilyl and more preferably $P^{3}$ and $P^{4}$ are the same.

Preferably, protecting group $P^{13**}$ is levulinoyl.

The coupling of compounds 24 and 25 is preferably performed in a mixture of apolar solvent and polar aprotic solvent, by treatment with NIS/TfOH at a temperature of between −10° C. and 10° C., and preferably between −5° C. and +5° C., and more preferably of about 0° C.

The coupling of compounds 27 and 28 is preferably performed in a mixture of apolar solvent and polar aprotic solvent, by treatment with TMSOTf at a temperature of between −10° C. and +10° C., and preferably of between −5° C. and +5° C., and more preferably of about 0° C.

The coupling of compounds 30 and 31 is preferably performed in an apolar solvent by treatment with TMSOTf at a temperature of between −40° C. and 0° C., and preferably of between −30° C. and −10° C., and more preferably of about −20° C.

The coupling of compounds 34 and 35 is preferably performed in an apolar solvent by treatment with NIS/TfOH at a temperature of between −60° C. and 0° C., and preferably of between −40° C. and −20° C., and more preferably of about −30° C.

To expedite the synthetic process, a modular approach can be alternatively used. Hence, a compound of general formula II-e could be easily accessed by coupling acceptor II-f with a donor II-g (see Scheme 1), wherein $P^{1}$, $P^{3}$-$P^{6}$, $P^{11}$-$P^{16**}$ have the meanings defined herein and $LG^6$ is a leaving group selected from:

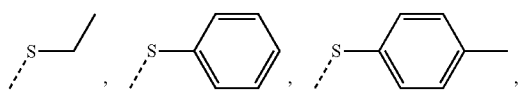

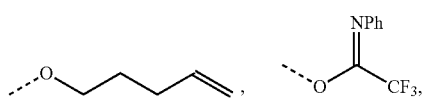

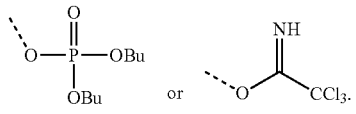

Scheme 1. Modular assembly of a compound II-e.

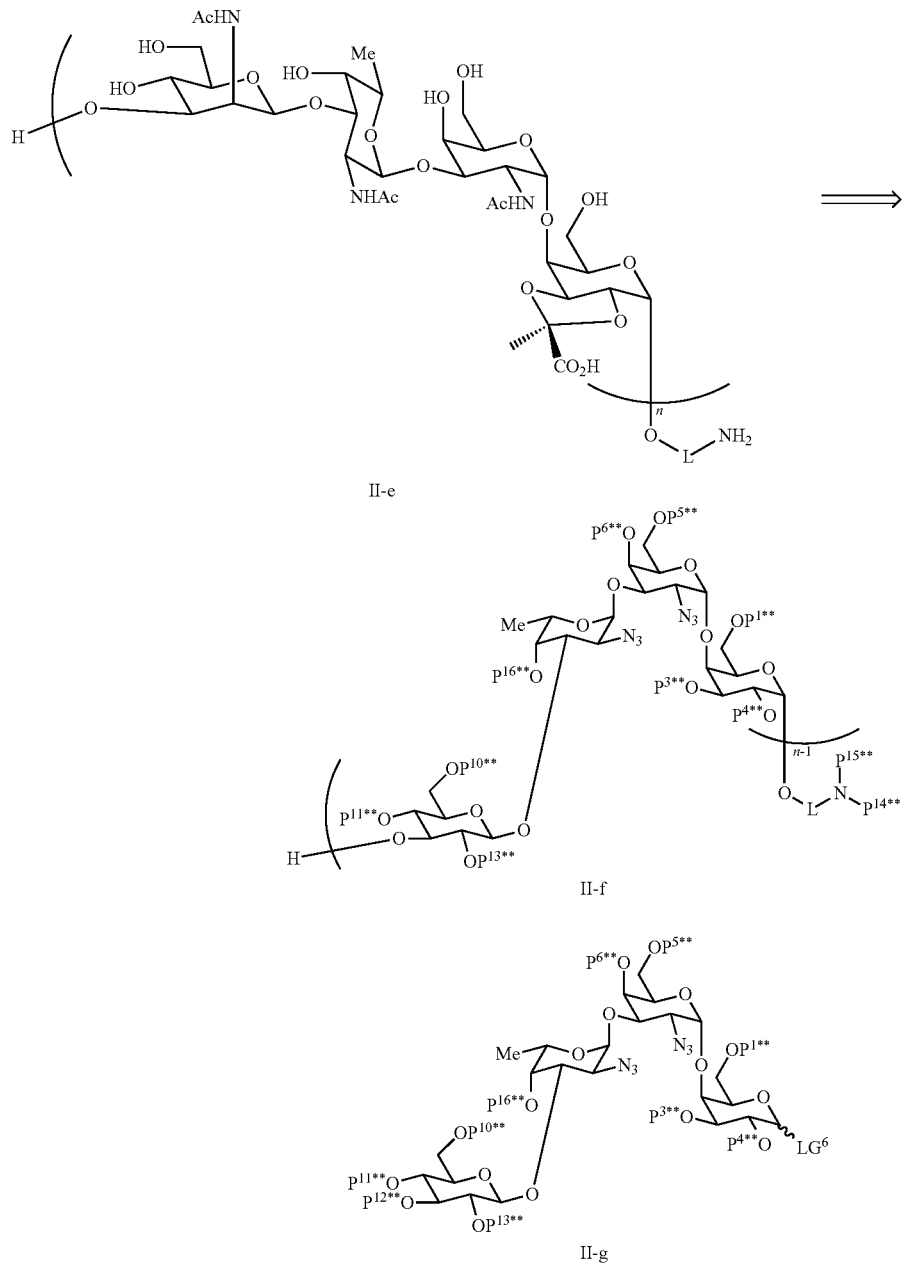

Glycoconjugates

Another aspect of the present invention refers to a conjugate comprising a saccharide of general formula (I) covalently bound or covalently linked to an immunogenic carrier through the nitrogen atom of the —O-L-NH$_2$ group. In other words, another aspect of the present invention is directed to a saccharide of any of the general formulae (I), (II), (II-a)-(II-d), (III), (III-a)-(III-d), (IV), (IV-a)-(IV-d), (V), (V-a)-(V-d) or (VI) conjugated with an immunogenic carrier through the nitrogen atom of the —O-L-NH$_2$ group. A conjugate comprising a synthetic saccharide of the general formula (I), (II), (II-a)-(II-d), (III), (III-a)-(III-d), (IV), (IV-a)-(IV-d), (V), (V-a)-(V-d) or (VI), covalently bound or covalently linked to an immunogenic carrier through the nitrogen atom of the —O-L-NH$_2$ group is also defined as a conjugate obtained by reacting a saccharide of any of the general formulae (I), (II), (II-a)-(II-d), (III), (III-a)-(III-d), (IV), (IV-a)-(IV-d), (V), (V-a)-(V-d), or (VI) with an immunogenic carrier. Said conjugate proved to be efficient as a vaccine for immunization against diseases associated with *Streptococcus pneumoniae* serotype 4 bacteria.

Saccharides are known by the person skilled in the art as generally TI-2 (T cell independent-2) antigens and poor immunogens. TI-2 antigens are antigens, which are recognized only by mature B cells through the cross linking of surface exposed immunoglobulin receptors. Without T cell help, no immunological memory is generated. Moreover, saccharides are known poor immunogens in humans due to the structural homology to human glycolipids and glycoproteins. Due to their poor immunogenic properties, saccharides manifest poor ability to produce both antibody production by B cells, as well as the formation of memory cells, features which are essential for the production of potent vaccines.

Therefore, to produce a potent saccharide-based vaccine, the saccharides of general formulae (I), (II), (II-a)-(II-d), (III), (III-a)-(III-d), (IV), (IV-a)-(IV-d), (V), (V-a)-(V-d), (VI) and tetrasaccharide 24* are conjugated to an immunogenic carrier to provide conjugates, which present increased immunogenicity in comparison with the saccharide. Hence, under the scope of the present application is covered also a conjugate consisting of a saccharide fragment.

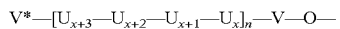

wherein V*, $U_{x+3}$, $U_{x+2}$, $U_{x+1}$, $U_x$, V, x and n have the meanings defined herein, covalently linked through the O atom to an immunogenic carrier.

Said conjugate comprises at least one synthetic saccharide of the general formula (I) and an immunogenic carrier to which the at least one saccharide (I) is covalently bound.

Surprisingly it was found that immunization with a conjugate comprising a saccharide of general formula (I) covalently linked to an immunogenic carrier results in the production of high titers of antibodies specific to the carbohydrate part of the saccharide of general formula (I). Said antibodies are cross-reacting with the natural SP-4 polysaccharides and present opsonophagocytosis and bactericidal activity, thus conferring protection against *S. pneumoniae* serotype 4 bacteria.

In this context the term "immunogenic carrier" is defined as a structure, which is conjugated to the saccharide to form a conjugate that presents an increased immunogenicity in comparison with the saccharide per se. Thus, the conjugation of the saccharides of the general formulae (I), (II), (II-a)-(II-d), (III), (III-a)-(III-d), (IV), (IV-a)-(IV-d), (V), (V-a)-(V-d), (VI) and tetrasaccharide 24* to the immunogenic carrier has as effect the stimulation of the immune response against the saccharide of general formula (I) without inducing an immune response against said immunogenic carrier.

Preferred immunogenic carriers are carrier proteins or glycosphingolipids with immunomodulatory properties. For the person skilled in the art, a carrier protein is a protein selected from the group comprising or consisting of: a diphtheria toxoid, a mutated diphtheria toxoid, a modified diphtheria toxoid, a mutated and modified diphtheria toxoid, a tetanus toxoid, a modified tetanus toxoid, a mutated tetanus toxoid, non-lipidated cell-surface liporotein (protein D) of non-typeable *Haemophilus influenzae*, outer membrane protein (OMP) complex of *Neisseria meningitidis*, bovine serum albumin (BSA), keyhole limpet hemocyanine (KLH) or cholera toxoid (CT). The term "toxoid" as used herein refers to a bacterial toxin (usually an exotoxin), whose toxicity has been inactivated or suppressed either by chemical (formalin) or heat treatment, while other properties, typically immunogenicity, are maintained. A mutated toxoid as used herein is a recombinant bacterial toxin, which has been amended to be less toxic or even non-toxic by amending the wild-type amino acid sequence. Such a mutation could be a substitution of one or more amino acids. Such a mutated toxoid presents on its surface a functionality that can react with the functional group Y of the interconnecting molecule to provide a modified toxoid. Said functionality is known to the person skilled in the art and includes, but is not restricted to the primary amino functionality of a lysine residue that can react with activated esters, an isocyanate group or an aldehyde in presence of a reducing agent, to the carboxylate functionality of a glutamate or aspartate residue that can be activated by carbodiimides or to the thiol functionality of a cysteine residue.

Activated esters include N-(γ-maleimidobutyryloxy) sulfosuccinimide ester (sulfo-GMBS), succinimidyl (4-iodoacetyl) aminobenzoate (sulfo-SIAB), succinimidyl-3-(bromoacetamido)propionate (SBAP), disuccinimidyl glutarate (DSG), disuccinimidyl adipate (DSA), 2-pyridyldithiol-tetraoxatetradecane-N-hydroxysuccinimide (PEG-4-SPDP) (see FIG. 2).

The cysteine residue on the carrier protein can be converted to the corresponding dehydroalanine that can be further reacted with a suitable interconnecting molecule to provide modified carrier protein having on their surface the functional group X of the interconnecting molecule.

It is especially preferred that the saccharides of general formula I are conjugated to the non-toxic mutated diphtheria toxin $CRM_{197}$ presenting as a functionality a primary amine functionality of a lysine residue.

$CRM_{197}$ like wild-type diphtheria toxin is a single polypeptide chain of 535 amino acids (58 kD) consisting of two subunits linked by disulfide bridges having a single amino acid substitution of glutamic acid for glycine. It is utilized as a carrier protein in a number of approved conjugate vaccines for diseases such as Prevnar.

Thus, in a preferred embodiment of the present invention the carrier protein presents on its surface primary amino functionalities of lysine residues that are able to react with the functional group Y of the interconnecting molecule to provide modified carrier protein having on their surface said functional group X of the interconnecting molecule, which is able to react with the terminal amino group of the linker of the compounds of general formula (I).

Said functional group X of the interconnecting molecules is selected of the group comprising or consisting of: maleimide; α-iodoacetyl; α-bromoacetyl; and N-hydroxysuccinimide ester (NHS), aldehyde, imidoester, carboxylic acid, alkyl sulfonate, sulfonyl chloride, epoxide, anhydride, carbonate (see FIG. 3).

Preferably, the saccharide of general formula I is conjugated to the non-toxic mutated diphtheria toxin $CRM_{197}$, which is modified by maleimide. In yet another preferred embodiment, the saccharide of general formula I is conjugated to the non-toxic mutated diphtheria toxin $CRM_{197}$, which is modified by α-bromoacetamide. In the most preferred embodiment, the saccharide of general formula I is conjugated to the non-toxic mutated diphtheria toxin $CRM_{197}$, which is modified by N-hydroxysuccinimide adipate.

Preferred is a conjugate of general formula (VII)

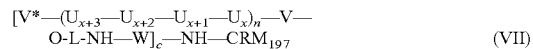

wherein
c is comprised between 2 and 18;
—W— is selected from:

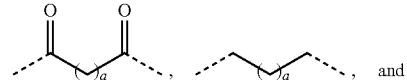

-continued

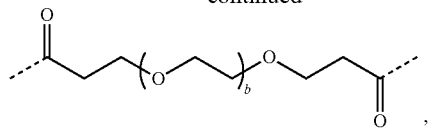

a represents an integer selected from 1, 2, 3, 4, 5, 6, 7, 8, 9 and 10, b represents an integer selected from 1, 2, 3 and 4, and $V^*$, $U_{x+3}$, $U_{x+2}$, $U_{x+1}$, $U_x$, V, x and n have the meanings defined herein.

Preferably, in general formula (VII) the linker -L- is selected from: $-L^a-$, $-L^a-L^e-$, $-L^a-L^b-L^e-$, and $-L^a-L^d-L^e-$;

$-L^a-$ is selected from: $-(CH_2)_o-$, $-(CH_2-CH_2-O)_o-C_2H_4-$, $-(CH_2-CH_2-O)_o-CH_2$; $-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

and o, q, p1 and p2 are independently of each other an integer selected from 1, 2, 3, 4, 5, and 6.

Also a conjugate of general formula (VII), wherein —W— represents

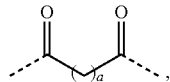

and a is an integer selected from 2, 3, 4, 5 and 6 is preferred.

A conjugate of general formula (VII), wherein the linker -L- is selected from: $-L^a-$, $-L^a-L^e-$, $-L^a-L^b-L^e-$, and $-L^a-L^d-L^e-$;

$-L^a-$ is selected from: $-(CH_2)_o-$, $-(CH_2-CH_2-O)_o-C_2H_4-$, $-(CH_2-CH_2-O)_o-CH_2$;

$-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

o, q, p1 and p2 are independently of each other an integer selected from 1, 2, 3, 4, 5, and 6;

—W— represents

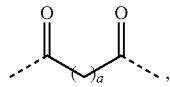

and a is an integer selected from 2, 3, 4, 5 and 6 is especially preferred.

Even more preferred is a conjugate of general formula (VII), wherein x represents 1, $V^*-$ represents H—, the linker -L- is selected from: $-L^a-$, $-L^a-L^e-$, $-L^a-L^b-L^e-$, and $-L^a-L^d-L^e-$;

$-L^a-$ is selected from: $-(CH_2)_o-$, $-(CH_2-CH_2-O)_o-C_2H_4-$, $-(CH_2-CH_2-O)_o-CH_2$;

$-L^b-$ represents $-O-$;

$-L^d-$ is selected from: $-(CH_2)_q-$, $-(CF_2)_q-$, $-(CH_2-CH_2-O)_q-C_2H_4-$, and $-(CH_2-CH_2-O)_q-CH_2-$;

$-L^e-$ is selected from: $-(CH_2)_{p1}-$, $-(CF_2)_{p1}-$, $-C_2H_4-(O-CH_2-CH_2)_{p1}-$, $-CH_2-(O-CH_2-CH_2)_{p1}-$ and $-(CH_2)_{p1}-O-(CH_2)_{p2}-$;

o, q, p1 and p2 are independently of each other an integer selected from 1, 2, 3, 4, 5, and 6;

—W— represents

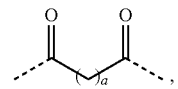

and a is an integer selected from 2, 3, 4, 5 and 6.

Particularly preferred is a conjugate of general formula (VII), wherein the linker -L- represents $-(CH_2)_o-$, o is an integer selected from 2, 3, 4, 5 and 6;

—W— represents

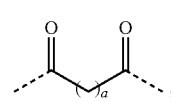

and a is an integer selected from 2, 3, 4, 5 and 6.

Also preferred is a conjugate of general formula (VII), wherein x represents 1, $V^*-$ represents H—, the linker -L- represents $-(CH_2)_o-$, o is an integer selected from 2, 3, 4, 5 and 6;

—W— represents

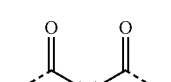

and a is an integer selected from 2, 3, 4, 5 and 6.

Preferably c is comprised between 2 and 18, more preferably between 5 and 15, even more preferably between 8 and 12. It is also preferred that n represents 1.

In another embodiment, said immunogenic carrier is preferably a glycosphingolipid with immunomodulatory properties, and more preferably (2S,3S,4R)-1-(α-D-galactopyranosyl)-2-hexacosanoylaminooctadecane-3,4-diol. The term glycosphingolipid with immunomodulatory properties, as used herein, refers to a suitable glycosphingolipid capable of stimulating the immune system's response to a target antigen, but which does not in itself confer immunity as defined above.

Glycosphingolipids as used herein are compounds containing a carbohydrate moiety α-linked to a sphingolipid. Preferably, the carbohydrate moiety is a hexopyranose and most preferably is α-D-galactopyranose. For the person skilled in the art, sphingolipids are a class of lipids containing a C18 amino alcohol connected via an amide bond to a fatty acid. The C18 amino alcohol is preferably mono-, di- or polysubstituted with hydroxyl groups. Especially preferred, the C18 amino alcohol is phytosphingosine. The fatty acid is preferably a monocarboxylic acid having a saturated alkyl chain of a number of carbons ranging from 16 to 28 and more preferably from 18 to 26. Glycosphingolipids with immunomodulatory properties include, but they are not restricted to (2S,3S,4R)-1-(α-D-galactopyranosyl)-2-hexacosanoylaminooctadecane-3,4-diol, which can stimulate natural killer (NK) activity and cytokine production by natural killer T (NKT) cells and exhibits potent antitumor activity in vivo (*Proc. Natl Acad. Sci.* USA, 1998, 95, 5690).

The conjugates of the saccharides of general formula I with a glycosphingolipid with immunomodulatory properties have the advantage of being heat stable. To be suitable for conjugation, on the glycosphingolipid with immunomodulatory properties a functionality is introduced. Said functionality is prone to react directly with the terminal amino group of the linker of the saccharides of general formula I to provide conjugates of the saccharides of general formula I, or with the functional group Y of the interconnecting molecule to provide the modified glycosphingolipid with immunomodulatory properties.

Preferably, said functionality is introduced at the C6 of the carbohydrate moiety of the glycosphingolipid with immunomodulatory properties. Thus, the glycosphingolipid with immunomodulatory properties is functionalized with a functionality, which is prone of reacting with the terminal amino group of the saccharides or with the functional group Y of the interconnecting molecule. A functionality prone to react with an amino group includes, but it is not restricted to activated ester, isocyanate group, aldehyde, epoxide, imidoester, carboxylic acid, alkyl sulfonate and sulfonyl chloride. A functionality prone to react with the functional group Y of the interconnecting molecule so that to provide the modified glycosphingolipid with immunomodulatory properties presenting the functional group X of the interconnecting molecule includes, but it is not restricted to amine, alcohol, thiol, activated ester, isocyanate group, aldehyde, epoxide, vinyl, imidoester, carboxylic acid, alkyl sulfonate, sulfonyl chloride, vinyl group, alkynyl group and azido group.

Preferably, the functionality introduced at the C6 of the carbohydrate moiety of the glycosphingolipid with immunomodulatory properties is selected from the group comprising or containing an amine, a thiol, an alcohol, a carboxylic acid, a vinyl, maleimide, α-iodoacetyl, α-bromoacetyl, N-hydroxysuccinimide ester (NHS), 2-pyridyldithiols.

Said functional group X of the interconnecting molecules is selected of the group comprising or consisting of maleimide, α-iodoacetyl, α-bromoacetyl, N-hydroxysuccinimide ester (NHS), aldehyde, carboxylic acid, epoxyde, alkyl sulfonate, sulfonyl chloride, anhydride, carbonate.

As used herein, the term "interconnecting molecule" refers to a bifunctional molecule containing functional group X and functional group Y, wherein functional group X is capable of reacting with the terminal amino group on the linker -L- and the functional group Y is capable of reacting with a functionality present on the immunogenic carrier or on the solid support.

It was found that a conjugate comprising a saccharide of general formula (I), (II), (II-a), (II-b), (II-c), (II-d), (III), (III-a), (III-b), (III-c), (III-d), (IV), (IV-a), (IV-b), (IV-c), (IV-d), (V), (V-a), (V-b), (V-c). (V-d), or (VI) or tetrasaccharide 24* covalently bound or covalently linked to an immunogenic carrier through the nitrogen atom of the —O-L-NH$_2$ group, and particularly the conjugate of general formula (VII) elicits a protective immune response in a human and/or animal host, and therefore is useful for prevention and/or treatment of diseases associated with bacteria containing in their capsular polysaccharide one of the following saccharide fragments:

-3)-β-D-ManNAc-(1,3)-α-L-FucNAc-(1,3)-α-D-GalNAc-(1,4)-α-D-Gal-2,3(S)Pyr-(1-;
-4)-α-D-Gal-2,3(S)Pyr-(1,3)-β-D-ManNAc-(1,3)-α-L-FucNAc-(1,3)-α-D-GalNAc-(1-;
-3)-α-D-GalNAc-(1,4)-α-D-Gal-2,3(S)Pyr-(1,3)-β-D-ManNAc-(1,3)-α-L-FucNAc-(1-;
-3)-α-L-FucNAc-(1,3)-α-D-GalNAc-(1,4)-α-D-Gal-2,3(S)Pyr-(1,3)-β-D-ManNAc-(1-.

Preferably, the bacterium containing in the capsular polysaccharide one of the above mentioned saccharide fragments is *Streptococcus pneumoniae* serotype 4.

In a preferred embodiment, the conjugates comprising the saccharides of general formula I conjugated to an immunogenic carrier are useful for prevention and/or treatment of diseases associated with bacteria, and particularly with diseases associated with bacteria containing in their capsular polysaccharide one of the following saccharide fragments: -3)-β-D-ManNAc-(1,3)-α-L-FucNAc-(1,3)-α-D-GalNAc-(1,4)-α-D-Gal-2,3(S)Pyr-(1-; -4)-α-D-Gal-2,3(S)Pyr-(1,3)-β-D-ManNAc-(1,3)-α-L-FucNAc-(1,3)-α-D-GalNAc-(1-; -3)-α-D-GalNAc-(1,4)-α-D-Gal-2,3(S)Pyr-(1,3)-β-D-ManNAc-(1,3)-α-L-FucNAc-(1-; -3)-α-L-FucNAc-(1,3)-α-D-GalNAc-(1,4)-α-D-Gal-2,3(S)Pyr-(1,3)-β-D-ManNAc-(1-, and preferably with *Streptococcus pneumoniae* serotype 4, wherein said diseases include pneumonia, meningitis, otitis media, bacteremia and acute exacerbation of chronic bronchitis, sinusitis, arthritis and conjunctivitis.

Pharmaceutical Compositions

Another aspect of the present invention is directed to a pharmaceutical composition or a vaccine comprising a conjugate that comprises a saccharide according to the present invention covalently bound or covalently linked to an immunogenic carrier through the nitrogen atom of the —O-L-NH$_2$ and/or one saccharide according to the present invention together with at least one pharmaceutically acceptable adjuvant and/or excipient. Said pharmaceutical composition can be used for raising a protective immune response in a human and/or animal host. Ideally, the pharmaceutical composition is suitable for use in humans.

In another aspect of the present invention, said pharmaceutical composition or vaccine further comprises at least one of capsular polysaccharides and/or capsular polysaccharide fragments and/or protein conjugates thereof of *Streptococcus pneumoniae* bacteria selected from the group comprising or consisting of *Streptococcus pneumoniae* serotypes 6B, 9V, 14, 18C, 19F and 23F, preferably serotypes 1, 3, 5, 6A, 6B, 7F, 9V, 14, 18C, 19F and 23F, and more preferably serotypes 1, 2, 3, 5, 6B, 7F, 8, 9N, 9V, 10A, 11A, 12F, 14, 15B, 17F, 18C, 19F, 19A, 20, 22F, 23F and 33F.

The term "adjuvant" as used herein refers to an immunological adjuvant i.e. a material used in a vaccine composition that modifies or augments the effects of said vaccine by enhancing the immune response to a given antigen contained in the vaccine without being antigenically related to it. For the persons skilled in the art, classically recognized examples of immunological adjuvants include, but are not restricted to oil emulsions (e.g. Freund's adjuvant, MF59®), saponins, aluminum or calcium salts (e.g. alum), non-ionic block polymer surfactants, and many others.

Pharmaceutical compositions are preferably in aqueous form, particularly at the point of administration, but they can also be presented in non-aqueous liquid forms or in dried forms e.g. as gelatin capsules, or as lyophilisates, etc.

Pharmaceutical compositions may include one or more preservatives, such as thiomersal or 2-phenoxyethanol. Mercury-free compositions are preferred, and preservative-free vaccines can be prepared.

Pharmaceutical compositions may include a physiological salt, such as a sodium salt e.g. to control tonicity. Sodium chloride (NaCl) is typical and may be present at between 1 and 20 mg/ml. Other salts that may be present include potassium chloride, potassium dihydrogen phosphate, disodium phosphate dehydrate, magnesium chloride, calcium chloride, etc.

Pharmaceutical compositions can have an osmolality of between 200 mOsm/kg and 400 mOsm/kg.

Pharmaceutical compositions may include compounds (with or without an insoluble metal salt) in plain water (e.g. w.f.i.), but will usually include one or more buffers. Typical buffers include: a phosphate buffer; a Tris buffer; a borate buffer; a succinate buffer; a histidine buffer (particularly with an aluminium hydroxide adjuvant); or a citrate buffer. Buffer salts will typically be included in the 5-20 mM range.

Pharmaceutical compositions typically have a pH between 5.0 and 9.5 e.g. between 6.0 and 8.0.

Pharmaceutical compositions are preferably sterile and gluten free.

Pharmaceutical compositions are suitable for administration to animal (and, in particular, human) patients, and thus include both human and veterinary uses. They may be used in a method of raising an immune response in a patient, comprising the step of administering the composition to the patient.

The pharmaceutical compositions of the present invention may be administered before a subject is exposed to S. pneumoniae serotype 4 and/or after a subject is exposed to S. pneumoniae serotype 4.

Pharmaceutical compositions may be prepared in unit dose form. In some embodiments a unit dose may have a volume of between 0.1-1.0 mL e.g. about 0.5 mL.

The invention also provides a delivery device (e.g. syringe, nebuliser, sprayer, inhaler, dermal patch, etc.) containing a pharmaceutical composition of the invention e.g. containing a unit dose. This device can be used to administer the composition to a vertebrate subject.

The invention also provides a sterile container (e.g. a vial) containing a pharmaceutical composition of the invention e.g. containing a unit dose.

The invention also provides a unit dose of a pharmaceutical composition of the invention.

The invention also provides a hermetically sealed container containing a pharmaceutical composition of the invention. Suitable containers include e.g. a vial.

Pharmaceutical compositions of the invention may be prepared in various forms. For example, the compositions may be prepared as injectables, either as liquid solutions or suspensions. Solid forms suitable for solution in, or suspension in, liquid vehicles prior to injection can also be prepared (e.g. a lyophilized composition or a spray-freeze dried composition). The composition may be prepared for topical administration e.g. as an ointment, cream or powder. The composition may be prepared for oral administration e.g. as a tablet or capsule, as a spray, or as a syrup (optionally flavored). The composition may be prepared for pulmonary administration e.g. by an inhaler, using a fine powder or a spray. The composition may be prepared as a suppository. The composition may be prepared for nasal, aural or ocular administration e.g. as a spray or drops. Injectables for intramuscular administration are typical.

The pharmaceutical compositions may comprise an effective amount of an adjuvant i.e. an amount which, when administered to an individual, either in a single dose or as part of a series, is effective for enhancing the immune response to a co-administered S. pneumoniae serotype 4 antigen. This amount can vary depending upon the health and physical condition of the individual to be treated, age, the taxonomic group of individual to be treated (e.g. non-human primate, primate, etc.), the capacity of the individual's immune system to synthesize antibodies, the degree of protection desired, the formulation of the vaccine, the treating doctor's assessment of the medical situation, and other relevant factors. The amount will fall in a relatively broad range that can be determined through routine trials.

Techniques for the formulation and administration of the vaccine of the present invention may be found in "Remington's Pharmaceutical Sciences" Mack Publishing Co., Easton Pa.

A therapeutically effective dosage of one conjugate according to the present invention or of one saccharide of general formula (I) refers to that amount of the compound that results in an at least a partial immunization against a disease. Toxicity and therapeutic efficacy of such compounds can be determined by standard pharmaceutical, pharmacological, and toxicological procedures in cell cultures or experimental animals. The dose ratio between toxic and therapeutic effect is the therapeutic index. The actual amount of the composition administered will be dependent on the subject being treated, on the subject's weight, the severity of the affliction, the manner of administration and the judgement of the prescribing physician.

Another aspect of the present invention is directed to a method of inducing immune response against S. pneumoniae serotype 4 in a human and/or animal host, said method comprising administering of the saccharide of general formula (I) and/or salt thereof and/or a conjugate thereof or pharmaceutical composition thereof to said human and/or animal host. A method of treating or preventing diseases caused by S. pneumoniae serotype 4 in a human and/or animal host according to the present invention comprises administering of at least one saccharide of general formula (I) and/or salt thereof and/or a conjugate thereof or pharmaceutical composition thereof to said human and/or animal host.

Immunological Assays

Yet another aspect of the present invention refers to saccharide of general formula (I) for use as marker in immunological assays for detection of antibodies against bacteria containing in their capsular polysaccharide one of the following saccharide fragments:
- -3)-β-D-ManNAc-(1,3)-α-L-FucNAc-(1,3)-α-D-GalNAc-(1,4)-α-D-Gal-2,3(S)Pyr-(1-;
- -4)-α-D-Gal-2,3(S)Pyr-(1,3)-β-D-ManNAc-(1,3)-α-L-FucNAc-(1,3)-α-D-GalNAc-(1-;
- -3)-α-D-GalNAc-(1,4)-α-D-Gal-2,3(S)Pyr-(1,3)-β-D-ManNAc-(1,3)-α-L-FucNAc-(1-;
- -3)-α-L-FucNAc-(1,3)-α-D-GalNAc-(1,4)-α-D-Gal-2,3(S)Pyr-(1,3)-β-D-ManNAc-(1-.

Such assays comprise, for instance, microarray and ELISA useful for detection of antibodies against bacteria containing in their capsular polysaccharide one of the above mentioned saccharide fragments, such as *Streptococcus pneumoniae* serotype 4.

The saccharides of the present invention can be easily conjugated to solid supports for providing immunological assays useful for detection of antibodies against bacteria containing in their capsular polysaccharide one of the above mentioned saccharide fragments. Said solid supports present on their surface a functionality that is prone to react with the amino group of saccharides of general formula (I) or with the functional group Y of the interconnecting molecule to provide modified solid supports, presenting on their surface the functional group X of the interconnecting molecule that can further react with the amino group of saccharides of general formula (I). In an embodiment according to the present invention the solid supports are microarray slides, which present on their surface a functionality that is prone to react with the functional group Y of the interconnecting molecule to provide modified microarray slides, presenting of their surface the functional group X of the interconnecting molecule. Example of such microarray slides include, but are not restricted to Corning® epoxide coated slides or Corning® GAPS™ II coated slides.

In a preferred embodiment the solid supports are microarray slides presenting on their surface a functionality that is prone to react with the amino group of saccharides of general formula (I), and more preferably an N-hydroxysuccinimide (NHS) activated ester. Such microarray slides are for example CodeLink® NHS slides.

Figure 1:
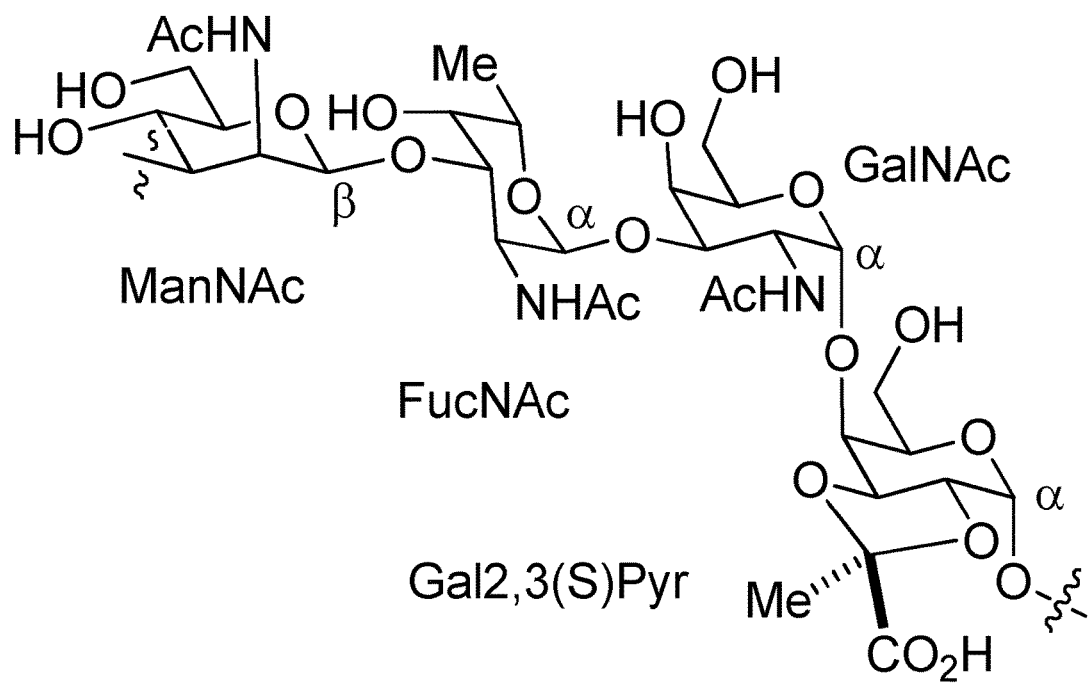
FIG. 1 shows the chemical structure of the S. pneumoniae serotype 4 capsular polysaccharide repeating unit.
Figure 3:
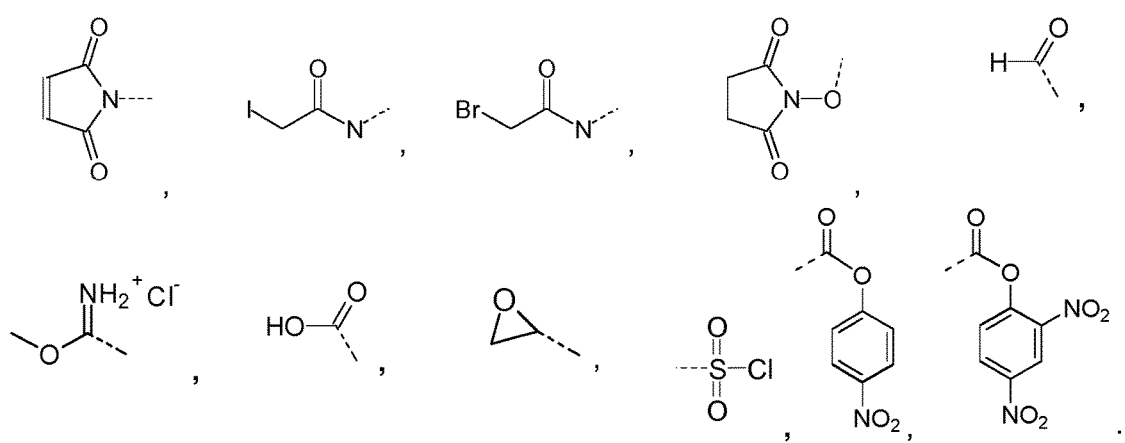
FIG. 3 provides examples of functional group X of the interconnecting molecule according to the present invention.
Figure 2:
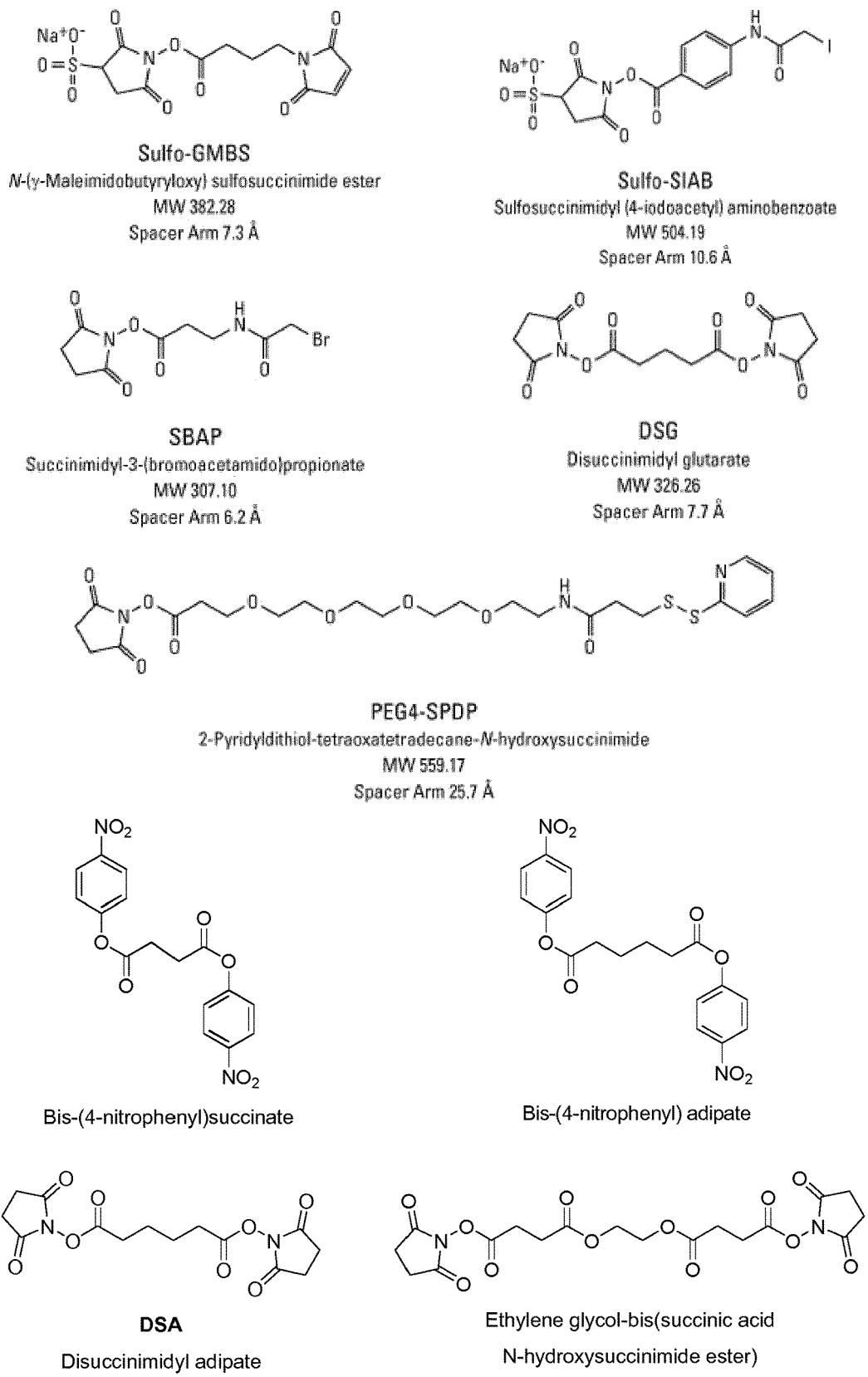
FIG. 2 provides examples of commercially available interconnecting molecules according to the present invention.
Figure 4:
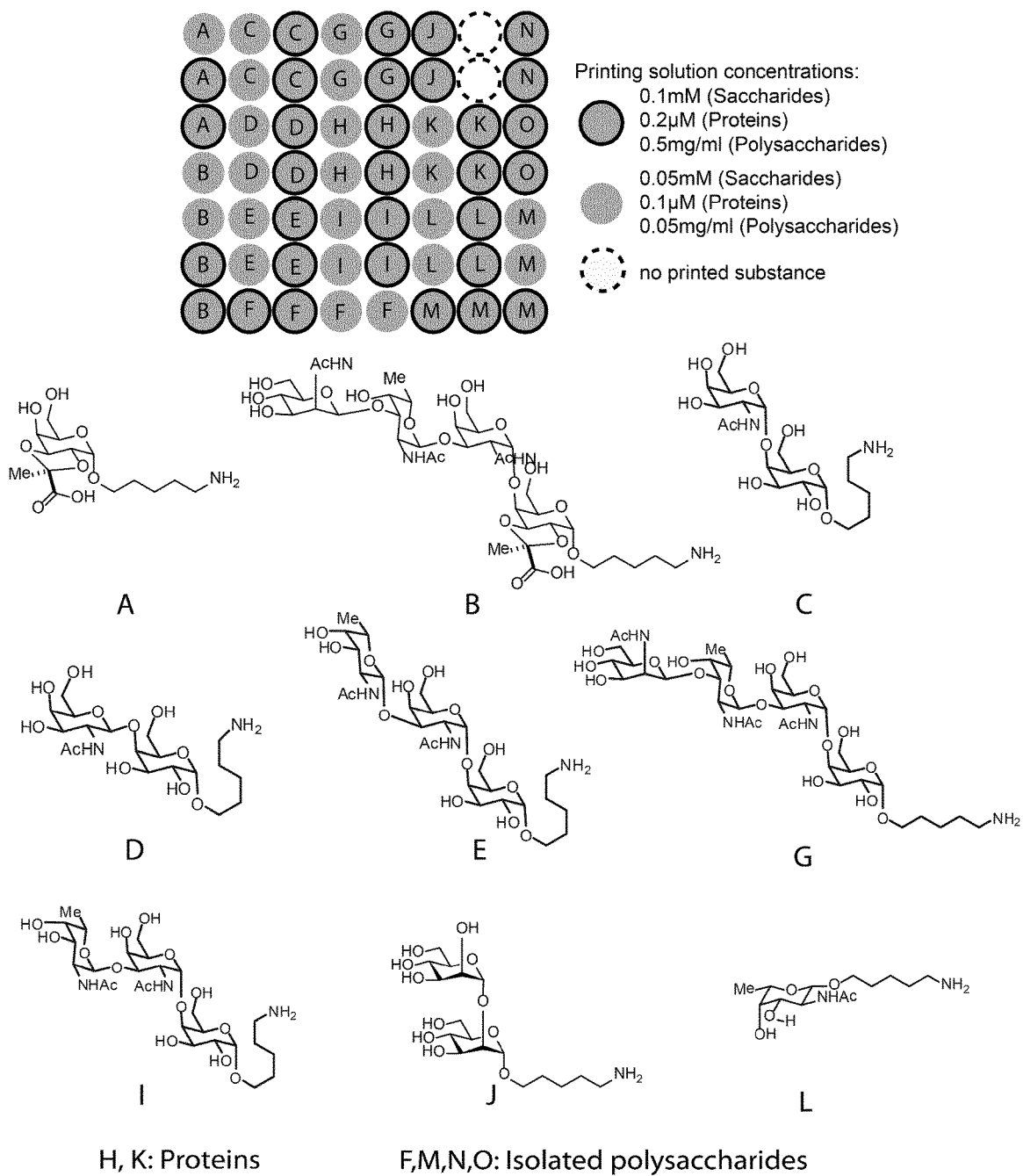
FIG. 4 Printing pattern of slides containing pyruvated tetrasaccharide 24* (spot B), depyruvated tetrasaccharide 16* (spot G), trisaccharide 20* (spot I) along with a number of deletion sequences thereof and saccharides with an unnatural stereochemistry thereof. The proteins $CRM_{197}$ and the BSA-GlcNAc conjugate were printed to determine antibody response against the carrier protein and the moiety "linker-interconnecting molecule" used during conjugation, respectively. Native S. pneumoniae polysaccharides were printed as controls.
Figure 5:
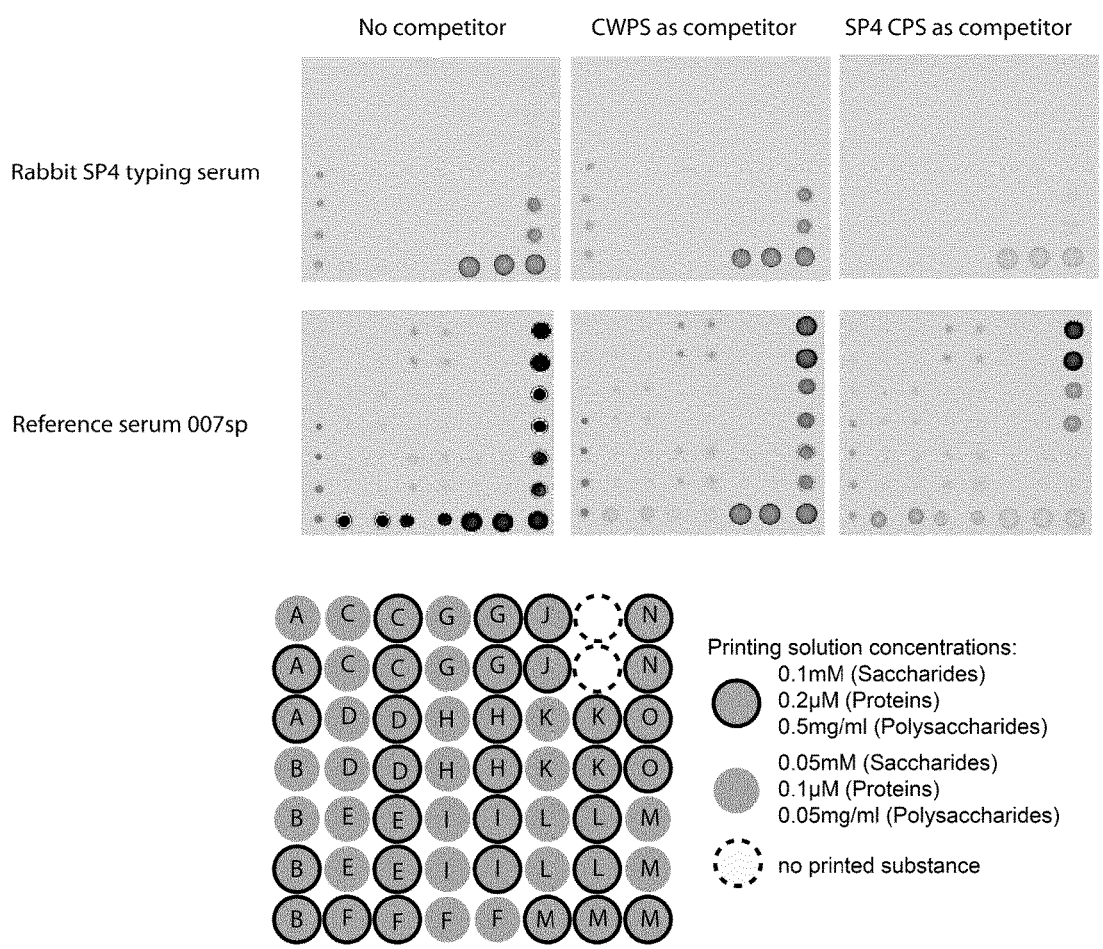

Spot A: (2S,3aR,4S,6R,7S,7aS)-4-((5-aminopentyl)oxy)-7-hydroxy-6-(hydroxyl-methyl)-2-methyltetrahydro-3aH-[1,3]dioxolo[4,5-c]pyran-2-carboxylic acid;
Spot B: pyruvated tetrasaccharide 24*;
Spot C: disaccharide 18*;
Spot D: N-((2S,3R,4R,5R,6R)-2-(((2R,3R,4R,5R,6S)-6-((5-aminopentyl)oxy)-4,5-dihydroxy-2-(hydroxymethyl)tetrahydro-2H-pyran-3-yl)oxy)-4,5-dihydroxy-6-(hydroxymethyl)tetrahydro-2H-pyran-3-yl)acetamide;
Spot E: N-((2R,3S,4S,5S,6S)-2-(((2R,3R,4R,5R,6R)-3-acetamido-2-(((2R,3R,4R,5R,6S)-6-((5-aminopentyl)oxy)-4,5-dihydroxy-2-(hydroxyl-methyl)tetrahydro-2H-pyran-3-yl)oxy)-5-hydroxy-6-(hydroxymethyl)tetrahydro-2H-pyran-4-yl)oxy)-4,5-dihydroxy-6-methyltetrahydro-2H-pyran-3-yl)acetamide;
Spot F: S. pneumoniae cell wall polysaccharide (SSI Diagnostica);
Spot G: tetrasaccharide 16*;
Spot H: recombinant $CRM_{197}$ (Pfenex Inc.);
Spot I: trisaccharide 20*;
Spot J: (2R,3S,4S,5S,6R)-2-(((2S,3S,4S,5S,6R)-2-((5-aminopentyl)oxy)-4,5-dihydroxy-6-(hydroxymethyl)tetrahydro-2H-pyran-3-yl)oxy)-6-(hydroxymethyl)tetrahydro-2H-pyran-3,4,5-triol;
Spot L: monosaccharide 21*;
Spot K: BSA-GlcNAc control conjugate for anti-"linker-interconnecting molecule" antibody response;
Spot M: S. pneumoniae serotype 4 CPS (SSI Diagnostica);
Spot N: S. pneumoniae serotype 2 CPS (SSI Diagnostica);
Spot O: S. pneumoniae serotype 3 CPS (SSI Diagnostica);

FIG. 5 shows the detection of antibodies against synthetic SP4 based glycans in rabbit SP4 typing serum (SSI Diagnostica) and human reference serum 007sp using glycan array. Competition assay with cell wall polysaccharide (CWPS) and SP4 capsular polysaccharide (CPS) was performed to validate identity of antibodies against SP4 CPS (printing pattern according to FIG. 4). Compared to unpyruvated tetrasaccharide 16*, the signal for the pyruvated saccharide 24* can be inhibited far more efficiently by the native S. pneumoniae serotype 4 CPS suggesting a high number of cross-reactive antibodies. Competition with S. pneumoniae cell wall polysaccharide has no effect on signal strength (see further FIG. 6).

Figure 6:
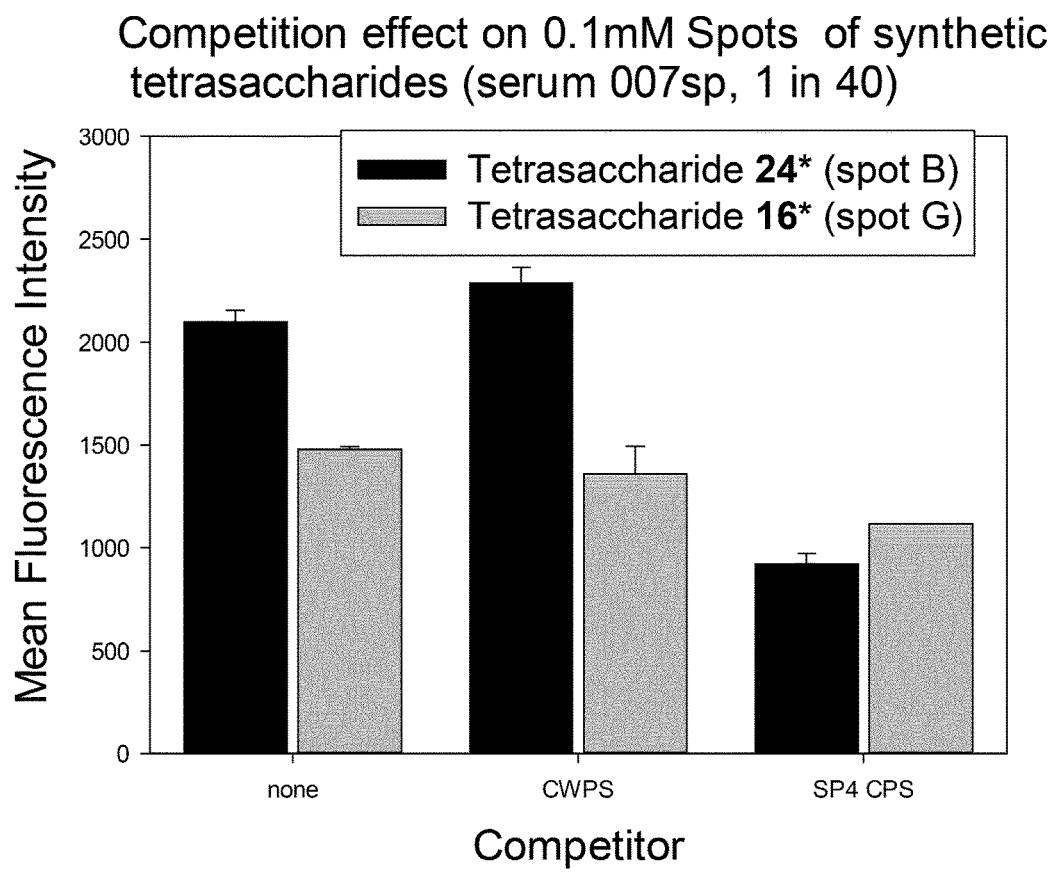

FIG. 6 shows the quantification of fluorescence intensities for competition experiment with serum 007sp as shown in FIG. 5. Signal decline in competition experiment with serum 007sp is much stronger for pyruvated tetrasaccharide 24* (spot B) compared with unpyruvated tetrasaccharide 16* (spot G) indicating higher antibody cross-reactivity.

The following examples are included to demonstrate preferred embodiments of the invention. It should be appreciated by those skilled in the art that the techniques disclosed in the examples, which follow represent techniques discovered by the inventor to function well in the practice of the invention, and thus can be considered to constitute preferred modes for its practice. However, those skilled in the art should, in light of the present disclosure, appreciate that many changes can be made in the specific embodiments, which are disclosed and still obtain a like or similar result without departing from the spirit and scope of the invention.

Further modifications and alternative embodiments of various aspects of the invention will be apparent to those skilled in the art in view of this description. Accordingly, this description is to be construed as illustrative only and is for the purpose of teaching those skilled in the art the general manner of carrying out the invention. It is to be understood that the forms of the invention shown and described herein are to be taken as examples of embodiments. Elements and materials may be substituted for those illustrated and described herein, parts and processes may be reversed, and certain features of the invention may be utilized independently, all as would be apparent to one skilled in the art after having the benefit of this description of the invention. Changes may be made in the elements described herein without departing from the spirit and scope of the invention as described in the following claims.

EXAMPLES

A. Chemical Synthesis
General Information:
Commercial grade solvents were used unless stated otherwise. Dry solvents were obtained from a Waters Dry Solvent System. Solvents for chromatography were distilled prior to use. Sensitive reactions were carried out in heat-dried glassware and under an argon atmosphere. Analytical thin layer chromatography (TLC) was performed on Kieselgel 60 F254 glass plates precoated with a 0.25 mm thickness of silica gel. Spots were visualized by staining with vanillin solution (6% (w/v) vanillin and 10% (v/v) sulfuric acid in 95% EtOH) or Hanessian's stain (5% (w/v) ammonium molybdate, 1% (w/v) cerium(II) sulfate and 10% (v/v) sulfuric acid in water). Silica column chromatography was performed on Fluka Kieselgel 60 (230-400 mesh). $^1$H, $^{13}$C and two-dimensional NMR spectra were measured with a Varian 400-MR spectrometer at 296 K. Chemical shifts (d) are reported in parts per million (ppm) relative to the respective residual solvent peaks (CDCl$_3$: d 7.27 in $^1$H and 77.23 in $^{13}$C NMR; CD$_3$OD: d 3.31 in $^1$H and 49.15 in $^{13}$C NMR). The following abbreviations are used to indicate peak multiplicities: s singlet; d doublet; dd doublet of doublets; t triplet; dt doublet of triplets; q quartet; m multiplet. Coupling constants (J) are reported in Hertz (Hz). Optical rotation (OR) measurements were carried out with a Schmidt & Haensch UniPol L1000 polarimeter at λ=589 nm and a concentration (c) expressed in g/100 mL in the solvent noted in parentheses. High resolution mass spectrometry (HRMS) was performed at the Free University Berlin, Mass. Spectrometry Core Facility, with an Agilent 6210 ESI-TOF mass spectrometer. Infrared (IR) spectra were measured with a Perkin Elmer 100 FTIR spectrometer.

Example 1A: Synthesis of (2R,3S,4S,5R,6S)-2-((benzyloxy)methyl)-6-(ethylthio)-4,5-bis(naphthalen-2-ylmethoxy)tetrahydro-2H-pyran-3-ol (1*)

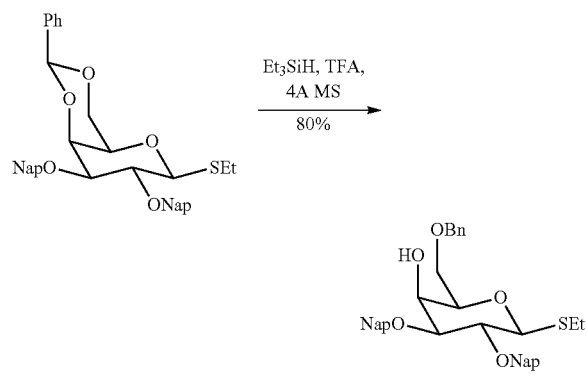

(2S,4aR,6S,7R,8S,8aS)-6-(ethylthio)-7,8-bis(naphthalen-2-ylmethoxy)-2-phenylhexahydropyrano[3,2-d][1,3]dioxine (S. D. Khaja, V. Kumar, M. Ahmad, J. Xue, K. L. Matta, *Tetrahedron Lett.* 2010, 51, 4411-4414.) (5.5 g, 9.2 mmol) was stirred in DCM (90 mL) with activated 4 Å MS (5.0 g) for 10 min before cooling to 0° C. Added triethylsilane (11.86 mL, 74.2 mmol) followed by TFA (4.29 mL, 55.7 mmol) dropwise and stirred the reaction mixture at room temperature for 4 h before quenching with water. Extracted the aqueous layer with CH$_2$Cl$_2$, and washed the organic layer with sat. aq. NaHCO$_3$, brine, dried over Na$_2$SO$_4$, filtered and concentrated to obtain oil. Purification by flash column chromatography using toluene and acetone as eluent (0 to 7.5%) afforded the compound 1* as colorless oil (4.4 g, 80%). [α]$_D^{20}$=+29.7° (c=1.10, CHCl$_3$); IR v$_{max}$ (film) 3570, 2858, 1362, 1081, 818, 735 cm$^{-1}$; $^1$H NMR (400 MHz, CDCl$_3$) δ 7.93-7.74 (m, 8H), 7.71 (d, J=7.8 Hz, 1H), 7.57 (d, J=8.4 Hz, 1H), 7.52-7.41 (m, 5H), 7.40-7.29 (m, 4H), 5.09 (d, J=9.7 Hz, 1H), 5.01-4.77 (m, 3H), 4.60 (d, J=1.3 Hz, 2H), 4.49 (dd, J=9.7, 1.6 Hz, 1H), 4.17 (s, 1H), 3.88-3.70 (m, 3H), 3.69-3.55 (m, 2H), 2.91-2.66 (m, 2H), 1.35 (td, J=7.4, 1.7 Hz, 3H). $^{13}$C NMR (100 MHz, CDCl$_3$) δ 138.1, 135.9, 135.3, 133.4, 133.3, 133.2 (2C), 128.6, 128.5, 128.2, 128.1 (2C), 127.9 (2C), 127.8 (2C), 127.1, 126.8, 126.5, 126.3, 126.2, 126.1, 126.0, 125.9, 85.3, 82.4, 78.2, 77.0, 76.3, 73.9, 72.3, 69.5, 67.1, 25.0, 15.3; HRMS (ESI): Calcd for C$_{37}$H$_{38}$O$_5$S [M+Na]$^+$617.2338, found: 617.2342.

Example 2A: Synthesis of (2R,3S,4S,5R,6S)-2-((benzyloxy)methyl)-6-(ethylthio)-4,5-bis(naphthalen-2-ylmethoxy)tetrahydro-2H-pyran-3-yl benzoate (2*)

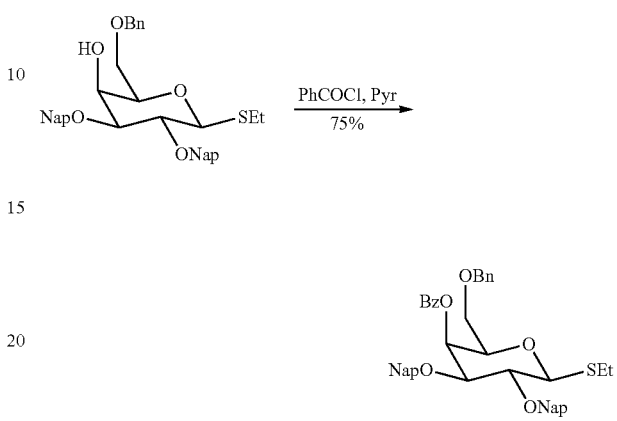

To a 0° C. cooled solution of 1* (4.3 g, 7.23 mmol) in pyridine (30 mL) was added benzoyl chloride (2.52 mL, 21.7 mmol) and stirred at room temperature for 13 h. Diluted the reaction mixture with water and extracted the aqueous layer with ether. Washed the organic layer with water, 1.0 M HCl, brine, dried over Na$_2$SO$_4$, filtered and concentrated to obtain oil. Purification by flash column chromatography using hexanes and ethyl acetate as eluent (0 to 10%) afforded the compound 2* as oil (3.8 g, 75%). [α]$_D^{20}$=+79.9° (c=1.60, CHCl$_3$); IR v$_{max}$ (film) 2862, 1721, 1272, 1095, 815, 701 cm$^{-1}$; $^1$H NMR (400 MHz, CDCl$_3$) δ 8.18-8.07 (m, 2H), 7.84-7.71 (m, 6H), 7.69 (d, J=8.7 Hz, 1H), 7.65-7.55 (m, 2H), 7.54-7.34 (m, 9H), 7.32-7.28 (m, 2H), 7.27-7.20 (m, 2H), 5.97 (dd, J=3.0, 0.9 Hz, 1H), 5.04 (t, J=10.9 Hz, 2H), 4.96 (d, J=10.6 Hz, 1H), 4.76 (d, J=11.7 Hz, 1H), 4.59 (d, J=9.2 Hz, 1H), 4.53 (d, J=11.7 Hz, 1H), 4.46 (d, J=11.8 Hz, 1H), 3.91-3.86 (m, 1H), 3.85-3.73 (m, 2H), 3.67 (dd, J=9.5, 5.9 Hz, 1H), 3.60 (dd, J=9.5, 7.0 Hz, 1H), 2.83 (qq, J=12.6, 7.4 Hz, 2H), 1.37 (t, J=7.4 Hz, 3H); $^{13}$C NMR (100 MHz, CDCl$_3$) δ 166.0, 137.7, 135.8, 135.4, 133.8, 133.4 (2C), 133.3, 133.2, 133.1, 130.3, 130.2, 130.0, 128.6 (2C), 128.5, 128.2, 128.1 (2C), 127.9, 127.8 (2C), 127.8, 127.2, 127.0, 126.6, 126.3, 126.1, 125.9, 85.6, 81.3, 78.0, 76.3, 76.1, 73.9, 71.9, 68.5, 67.8, 25.2, 15.3; HRMS (ESI): Calcd for C$_{44}$H$_{42}$O$_6$S [M+Na]$^+$721.2600, found: 721.2600.

Example 3A: Synthesis of (2R,3S,4S,5R,6S)-6-((5-(benzyl((benzyloxy)carbonyl)amino)pentyl)oxy)-2-((benzyloxy)methyl)-4,5-bis(naphthalen-2-ylmethoxy)tetrahydro-2H-pyran-3-yl benzoate (3*)

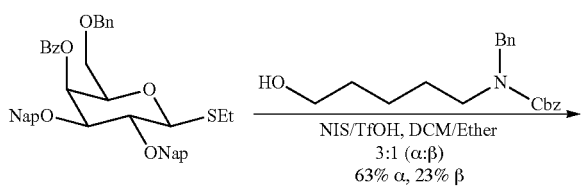

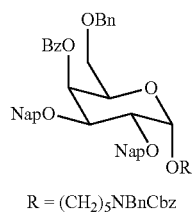

R = (CH$_2$)$_5$NBnCbz

Stirred a solution of microwave activated 4 Å acid washed molecular sieves (AWMS) (3.2 g), compound 2* (2 g, 2.86 mmol) and C5 aminopentyl linker (1.21 g, 3.72 mmol) in a mixture of ether and DCM (3:1; 36 mL:12 mL) at room temperature for 15 min. Cooled the reaction mixture to 0° C. and added NIS (0.78 g, 3.15 mmol) followed by TfOH (0.25 mL, 0.28 mmol) and stirred for 30 min. Diluted the reaction mixture with aq. sat. Na$_2$S$_2$O$_3$. Extracted the aqueous layer with ether, and dried the organic layer over Na$_2$SO$_4$, filtered and concentrated to obtain oil. Purification by flash column chromatography using hexanes and ethyl acetate as eluent (0 to 25%) afforded α-anomer 3* (1.75 g, 63%), and β-anomer (0.63 g, 23%) as oils, indicating a modest selectivity of ~3:1 (α:β)

NMR analysis: Because of the C5 aminopentyl linker the anomeric protons in the $^1$H nmr were submerged or the peaks were broadened and so, the confirmation of the linkage could not be established easily. From $^{13}$C for α-anomer, the anomeric carbon was at 98.4 ppm thereby indicating an α-linkage (literature 97 to 101) and the $J_{C1H1}$ was 167.7 Hz.$^x$ For β-anomer, the $^{13}$C value was 104.1 ppm for the anomeric indicating a β-anomer and falls in agreement with literature (103 to 105 ppm).$^x$ Also the $J_{C1H1}$ coupling for β-anomer was 158.8 Hz indicating a β-anomer. α-anomer: $[α]_D^{20}$=+95.8° (c=0.74, CHCl$_3$); IR $v_{max}$ (film) 2928, 1720, 1698, 1270, 1103, 1057, 740 cm$^{-1}$; $^1$H NMR (400 MHz, CDCl$_3$) δ 8.00 (dd, J=8.3, 1.2 Hz, 2H), 7.84-7.70 (m, 6H), 7.64 (dd, J=12.7, 5.0 Hz, 2H), 7.56 (t, J=7.4 Hz, 1H), 7.51-7.12 (m, 23H), 5.92 (s, 1H), 5.18 (bs, 2H), 5.03 (d, J=11.4 Hz, 1H), 4.98 (d, J=12.3 Hz, 1H), 4.90 (bs, 1H), 4.84 (d, J=12.2 Hz, 1H), 4.77 (d, J=11.4 Hz, 1H), 4.45 (m, 4H), 4.17 (bs, 2H), 3.99 (dd, J=10.0, 3.6 Hz, 1H), 3.65 (bs, 1H), 3.54 (d, J=6.3 Hz, 2H), 3.44 (bm, 1H), 3.22 (bm, 2H), 1.58 (bm, 4H), 1.31 (bm, 2H); $^{13}$C NMR (100 MHz, CDCl$_3$) δ 171.3, 166.0, 138.1, 137.9, 136.1, 135.9, 133.4, 133.3, 133.1, 133.0, 130.2, 130.0, 128.7, 128.6, 128.5, 128.5, 128.2, 128.1, 128.0 (3C), 127.8 (3C), 127.7, 127.4, 127.0, 126.7, 126.2, 126.1, 126.0, 125.9, 125.8, 98.0, 76.7, 75.2, 73.7, 73.5, 72.1, 69.0, 68.9, 68.4, 68.2, 67.3, 60.5, 50.6, 50.4, 47.3 (2C), 29.3, 28.1, 27.7, 23.6, 21.2, 14.4; HRMS (ESI): Calcd for C$_{62}$H$_{61}$NO$_9$ [M+Na]$^+$986.4244, found: 986.4144.

Example 4A: Synthesis of benzyl benzyl(5-(((2S, 3R,4S,5S,6R)-6-((benzyloxy)methyl)-5-hydroxy-3, 4-bis(naphthalen-2-ylmethoxy)tetrahydro-2H-pyran-2-yl)oxy)pentyl)carbamate (4*)

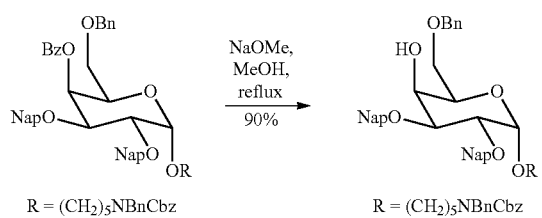

To a solution of compound 3* (1.5 g, 1.55 mmol) in a mixture of MeOH and THF (2:1; 10 mL: 5 mL) at room temperature was added a 0.5 M solution of NaOMe in methanol (0.78 mL, 0.39 mmol) and the reaction mixture heated to 50° C. for 30 h. The reaction was neutralized with Amberlite 120 H$^+$ resin, filtered and concentrated. Purification by flash column chromatography using hexanes and ethyl acetate as eluent (0 to 40%) afforded the compound 4* as oil (1.2 g, 90%). $[α]_D^{20}$=+61.8° (c=2.90, CHCl$_3$); IR $v_{max}$ (film) 3462, 2920, 1693, 1226, 1088, 1043, 731 cm$^{-1}$; $^1$H NMR (400 MHz, CDCl$_3$) δ 7.93-7.67 (m, 8H), 7.57-7.41 (m, 6H), 7.39-7.06 (m, 15H), 5.19 (s, 2H), 4.99 (d, J=11.8 Hz, 2H), 4.91 (d, J=11.7 Hz, 1H), 4.84 (bd, J=11.4 Hz, 2H), 4.59 (d, J=12.0 Hz, 1H), 4.55 (d, J=12.0 Hz, 1H), 4.49 (bd, J=12.7 Hz, 2H), 4.15 (s, 1H), 3.96 (d, J=12.3 Hz, 2H), 3.75 (dd, J=10.0, 5.4 Hz, 1H), 3.68 (dd, J=9.9, 6.3 Hz, 1H), 3.63 (d, J=8.3 Hz, 1H), 3.39 (bs, 1H), 3.23 (bm, 2H), 2.69 (s, 1H), 1.75-1.44 (bm, 4H), 1.32 (bm, 2H); $^{13}$C NMR (100 MHz, CDCl$_3$) δ 138.2, 136.1, 135.9, 133.4 (2C), 133.2, 128.7, 128.6, 128.5, 128.4, 128.3, 128.1, 128.0 (2C), 127.8 (3C), 127.4, 126.8, 126.6, 126.3, 126.2, 126.1 (2C), 125.9, 97.5, 77.8, 76.2, 73.7, 73.5, 73.0, 69.8, 68.6, 68.3, 68.2, 67.3, 29.3, 23.6; HRMS (ESI): Calcd for C$_{55}$H$_{57}$NO$_8$ [M+Na]$^+$ 882.3982, found: 882.3918.

Example 5A: Synthesis of (2S,3R,4S,5S,6S)-5-azido-2-methyl-6-(phenylselanyl)tetrahydro-2H-pyran-3,4-diyl diacetate (5*)

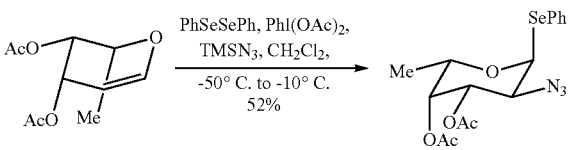

To a solution of (2S,3R,4S)-2-methyl-3,4-dihydro-2H-pyran-3,4-diyl diacetate (14.5 g, 67.7 mmol) and diphenyl diselenide (21.1 g, 67.7 mmol) in CH$_2$Cl$_2$ (220 mL) at −50° C. was added bisacetate iodobenzene (21.8 g, 67.7 mmol) followed by trimethylsilyl azide (17.9 mL, 135 mmol). The reaction mixture was warmed to −10° C. over a period of 1.5 h by which time no starting material was observed by TLC. The solvent was removed under vacuum to obtain the crude as reddish brown oil. Purification by flash column chromatography using cyclohexane and ethyl acetate as eluent (0 to 30%) afforded the compound 5* as oil (14.5 g, 52%). [Obtain also other compounds accounting for about 7.6 g whose identity could not be verified using mass and NMR spectroscopy]. IR $v_{max}$ (film) 2939, 2109, 1742, 1368, 1219, 1083, 1018, 740 cm$^{-1}$; $^1$H NMR (400 MHz, CDCl$_3$) δ 7.63-7.53 (m, 2H), 7.35-7.23 (m, 3H), 5.96 (d, J=5.4 Hz, 1H), 5.33 (dd, J=3.3, 1.3 Hz, 1H), 5.14 (dd, J=10.9, 3.2 Hz, 1H), 4.51 (q, J=6.5, 0.7 Hz, 1H), 4.24 (dd, J=10.9, 5.4 Hz, 1H), 2.18 (s, 3H), 2.07 (s, 3H), 1.10 (d, J=6.5 Hz, 3H); $^{13}$C NMR (100 MHz, CDCl$_3$) δ 170.4, 169.8, 134.8, 129.3, 129.1, 128.3, 128.2, 128.1, 84.5, 71.7, 70.2, 67.6, 58.9, 20.8, 20.7, 15.9; HRMS (ESI): Calcd for C$_{16}$H$_{19}$N$_3$O$_5$Se [M+Na]$^+$436.0388, found: 436.0400.

Example 6A: Synthesis of (2S,3R,4S,5S)-5-azido-2-methyl-6-(2,2,2-trichloro-1-iminoethoxy)tetrahydro-2H-pyran-3,4-diyl diacetate (6*)

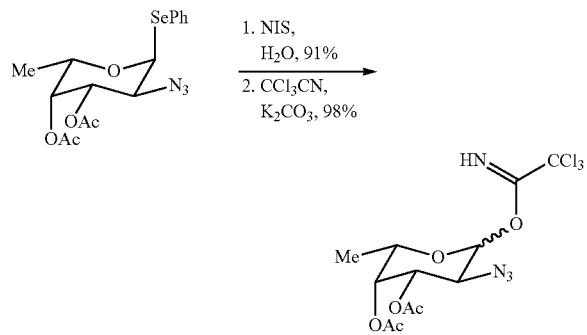

A solution of azidoselenide 5* (5.0 g, 12.1 mmol) in a mixture of THF, water and acetone (1:1:0.5; 28 mL:28 mL:14 mL) was cooled to 0° C. N-iodosuccinimide (5.4 g, 24.2 mmol) was added and the reaction mixture stirred at room temperature for 30 min. The reaction was diluted with ethyl acetate and the organic layer washed with sat. aq. $Na_2S_2O_3$ and brine respectively. Dried the organic layer over $Na_2SO_4$, filtered and concentrated to obtain the oil. Purification by flash column chromatography using hexanes and ethyl acetate as eluent (0 to 60%) afforded the compound as a 1:1 mixture of anomers (3.0 g, 91%). Dissolved the lactol (0.75 g, 2.7 mmol) in dichloroethane, and added trichloroacetonitrile (1.37 mL, 13.7 mmol) at room temperature followed by $K_2CO_3$ (1.02 g, 7.2 mmol) and stirred for 4 h. Filtered the reaction over celite and washed the celite with dichloromethane and removed the solvents under vacuum to obtain the compound 6* as a mixture of anomers (1.12 g, 98%, α:β=1:5.5). The NMR was clean and hence taken to the next step without further purification. $[\alpha]_D^{20}=-19.2°$ (c=1.64, $CHCl_3$); IR $v_{max}$ (film) 2993, 2114, 1751, 1729, 1679, 1235, 1216, 1070, 1031, 840, 793 $cm^{-1}$; $^1H$ NMR (400 MHz, $CDCl_3$) reported only β-anomer: δ 8.77 (s, 1H), 5.68 (d, J=8.5 Hz, 1H), 5.25 (dd, J=3.4, 0.9 Hz, 1H), 4.91 (dd, J=10.8, 3.4 Hz, 1H), 3.97-3.83 (m, 2H), 2.21 (s, 3H), 2.08 (s, 3H), 1.24 (d, J=6.4 Hz, 3H); $^{13}C$ NMR (100 MHz, $CDCl_3$) δ 170.6, 169.9, 161.1, 97.0, 71.8, 70.5, 69.4, 60.5, 20.8 (2C), 16.2; HRMS (ESI): Calcd for $C_{12}H_{15}Cl_3N_4O_6$ [M+Na]$^+$ 438.9955, found: 438.9940.

Example 7A: Synthesis of (2S,4aR,6R,7R,8R,8aR)-7-azido-6-(((2R,3S,4S,5R,6S)-6-((5-(benzyl((benzyloxy)carbonyl)amino)pentyl)oxy)-2-((benzyloxy)methyl)-4,5-bis(naphthalen-2-ylmethoxy)tetrahydro-2H-pyran-3-yl)oxy)-2-phenylhexahydropyrano[3,2-d][1,3]dioxin-8-yl acetate (7*)

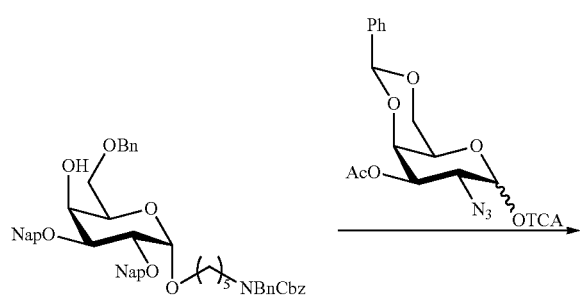

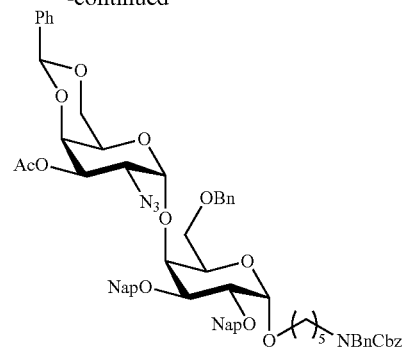

To a solution of (2S,4aR,7R,8R,8aR)-7-azido-2-phenyl-6-(2,2,2-trichloro-1-iminoethoxy)hexahydropyrano[3,2-d][1,3]dioxin-8-yl acetate (1.75 g, 2.03 mmol) and acceptor 4* (1.26 g, 2.65 mmol) in a mixture of ether and $CH_2Cl_2$ (1:1; 11.6 mL: 11.6 mL) at 0° C. was added TMSOTf (0.037 mL, 0.20 mmol) and the reaction mixture stirred at 0° C. for 15 min. Quenched the reaction by adding a drop of $Et_3N$ and removed the solvents under vacuum. Purification by flash column chromatography using hexanes and ethyl acetate as eluent (0 to 20%) afforded α-anomer 7* (1.89 g, 79%) as oil and β-anomer, (0.26 g, 11%) as oil. The selectivity for the glycosylation ranged from 10:1 to 7:1 (α:β)

NMR analysis: $^1H$ NMR analysis of α-anomer showed only one anomeric proton that was distinct with J=3.5 Hz. The other anomeric proton was embedded within the napthyl methylene protons. For the β-anomer the coupling constant was J=8.1 Hz. $^{13}C$ indicated a value of 99.5 and 97.1 ppm for α-anomer and 101.8 and 97.7 ppm for β-anomer. The $J_{C1H1}$ coupling for fraction-1 was 170.4 Hz and 166.2 Hz indicating two α-anomeric linkages and was 168.6 Hz and 164.3 Hz for β-anomer indicating one α- and one β-anomeric linkages. α-anomer: $[\alpha]_D^{20}=+129.0°$ (c=1.25, $CHCl_3$); IR $v_{max}$ (film) 2925, 2109, 1744, 1694, 1225, 1089, 1042, 748 $cm^{-1}$; $^1H$ NMR (400 MHz, $CDCl_3$) δ 7.90 (s, 1H), 7.87-7.70 (m, 7H), 7.58 (d, J=8.6 Hz, 1H), 7.53-7.04 (m, 25H), 5.24 (dd, J=11.1, 3.3 Hz, 1H), 5.19 (s, 1H), 5.17 (s, 2H), 5.08 (d, J=3.5 Hz, 1H), 4.97 (d, J=11.9 Hz, 1H), 4.94-4.81 (m, 4H), 4.54 (s, 2H), 4.47 (d, J=10.0 Hz, 2H), 4.30 (d, J=2.7 Hz, 1H), 4.14 (d, J=2.9 Hz, 1H), 4.07 (s, 1H), 4.02 (dd, J=10.3, 3.6 Hz, 1H), 3.98-3.86 (m, 4H), 3.64-3.46 (m, 3H), 3.35 (bs, 1H), 3.20 (bm, 2H), 3.02 (d, J=11.7 Hz, 1H), 2.16 (s, 3H), 1.56 (bm, 4H), 1.38-1.06 (bm, 2H); $^{13}C$ NMR (100 MHz, $CDCl_3$) δ 170.5, 138.1, 137.8, 137.7, 136.1, 133.4 (2C), 133.2, 133.0, 129.1, 128.7, 128.6 (2C), 128.3 (2C), 128.2 (2C), 128.1, 128.0, 127.9, 127.8, 127.4, 127.2, 126.6, 126.3 (2C), 126.2, 126.0 (2C), 125.9, 125.5, 100.5, 99.0, 97.3, 77.2, 76.5, 74.6, 73.7, 73.4, 73.3, 73.1, 70.4, 69.0, 68.8, 68.3, 67.2, 62.3, 58.0, 29.3, 23.6, 21.2; HRMS (ESI): Calcd for $C_{70}H_{72}N_4O_{13}$ [M+Na]$^+$ 1199.4994, found: 1199.4902.

Example 8A: Synthesis of benzyl (5-(((2S,3R,4S,5S,6R)-5-(((2S,4aR,6R,7R,8R,8aR)-7-azido-8-hydroxy-2-phenylhexahydropyrano[3,2-d][1,3]dioxin-6-yl)oxy)-6-((benzyloxy)methyl)-3,4-bis(naphthalen-2-ylmethoxy)tetrahydro-2H-pyran-2-yl)oxy)pentyl)(benzyl)carbamate (8*)

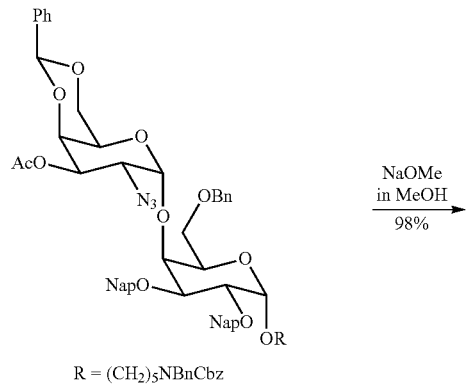

R = (CH$_2$)$_5$NBnCbz

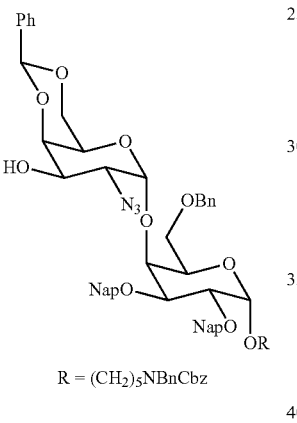

R = (CH$_2$)$_5$NBnCbz

To a solution of the compound 7* (1.85 g, 1.57 mmol) in a mixture of methanol and THF (2:1; 16 mL: 8 mL) was added a 0.5 M solution of NaOMe in MeOH (0.31 mL, 0.15 mmol) and stirred for 12 h at room temperature. The reaction was neutralized using Amberlite 120 H$^+$ resin, filtered, and concentrated. Purification by flash column chromatography using hexanes and ethyl acetate as eluent (0 to 20%) afforded the compound 8* (1.74 g, 98%) as white foam. [α]$_D^{20}$=+88.9° (c=1.15, CHCl$_3$); IR ν$_{max}$ (film) 3474, 2925, 2111, 1740, 1694, 1234, 1088, 1041, 748 cm$^{-1}$; $^1$H NMR (400 MHz, CDCl$_3$) δ 7.92-7.68 (m, 8H), 7.58 (d, J=8.2 Hz, 1H), 7.55-7.43 (m, 5H), 7.42-7.07 (m, 20H), 5.18 (bs, 3H), 5.01 (d, J=3.4 Hz, 1H), 4.98 (s, 1H), 4.94 (s, 1H), 4.92-4.78 (m, 3H), 4.54 (s, 2H), 4.48 (bd, J=9.2 Hz, 2H), 4.28 (s, 1H), 4.03-3.83 (m, 6H), 3.66-3.52 (m, 4H), 3.50 (dd, J=10.5, 3.4 Hz, 1H), 3.47-3.32 (bm, 1H), 3.30-3.13 (m, 2H), 3.07 (d, J=11.6 Hz, 1H), 1.79-1.43 (bm, 4H), 1.41-1.10 (bm, 2H); $^{13}$C NMR (100 MHz, CDCl$_3$) δ 138.1, 137.7, 137.6, 136.1, 135.9, 133.4, 133.3, 133.2, 133.0, 129.4, 128.7, 128.6 (2C), 128.4, 128.3, 128.2 (2C), 128.1 (2C), 128.0, 127.9 (2C), 127.3, 126.7, 126.4 (2C), 126.3, 126.2, 126.1, 125.9, 125.6, 101.0, 99.2, 97.0, 77.2, 75.5, 74.4, 74.5, 73.7, 73.0, 72.8, 69.1, 69.0, 68.3, 67.7, 67.3, 62.6, 61.4, 29.3, 23.6; HRMS (ESI): Calcd for C$_{68}$H$_{70}$N$_4$O$_{12}$ [M+Na]$^+$ 1157.4888, found: 1157.4923.

Example 9A: Synthesis of benzyl (5-(((2S,3R,4S,5S,6R)-5-(((2S,4aR,6R,7R,8R,8aR)-7-azido-8-(((2S,3S,4S,5S,6S)-3-azido-4,5-dihydroxy-6-methyltetrahydro-2H-pyran-2-yl)oxy)-2-phenylhexahydropyrano[3,2-d][1,3]dioxin-6-yl)oxy)-6-((benzyloxy)methyl)-3,4-bis(naphthalen-2-ylmethoxy)tetrahydro-2H-pyran-2-yl)oxy)pentyl)(benzyl)carbamate (9*)

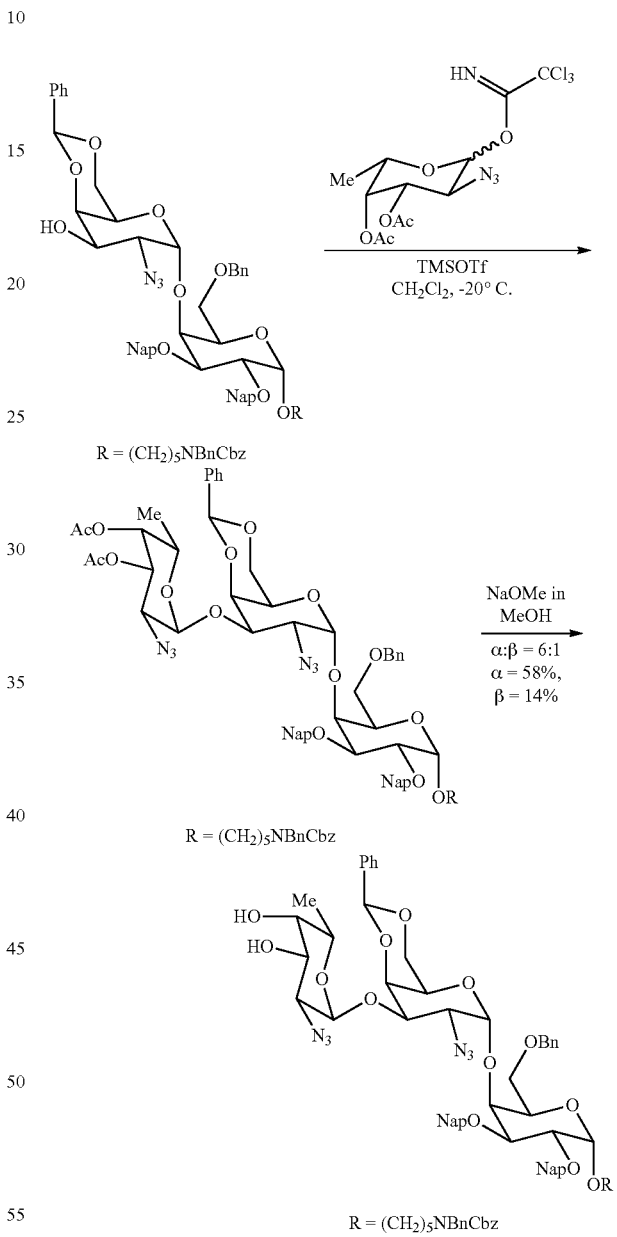

R = (CH$_2$)$_5$NBnCbz

R = (CH$_2$)$_5$NBnCbz

R = (CH$_2$)$_5$NBnCbz

To a solution of donor compound (2S,3R,4S,5S)-5-azido-2-methyl-6-(2,2,2-trichloro-1-iminoethoxy)tetrahydro-2H-pyran-3,4-diyl diacetate 6* (0.5 g, 1.2 mmol) and acceptor 8* (1.05 g, 0.92 mmol) in DCM (10 mL) at −20° C. was added TMSOTf (0.017 mL, 0.092 mmol) and the reaction mixture warmed to 0° C. over 30 min. Quenched the reaction by addition of two drops of Et$_3$N, and evaporated. Purification by flash column chromatography using toluene and acetone as eluent (0 to 25%) afforded the intermediate trisaccharide as a mixture of anomers that could not be separated easily at this step. To a solution of intermediate trisaccharide in a mixture of methanol and THF (2:1; 7 mL:3.5 mL) was added 0.5 M solution of NaOMe in MeOH (0.185 mL, 0.092 mmol) and stirred at room temperature for 12 h. The reaction was neutralized with Amberlite 120 H+ resin, filtered, and concentrated. Purification by flash column chromatography using hexanes and ethyl acetate as eluent (0 to 25%) afforded α-anomer 9* (0.70 g, 58%) and β-anomer (0.12 g, 14%) as white foams.

NMR analysis: $^1$H NMR of α-anomer contained three α-anomeric protons with chemical shift and coupling constant of 5.09 ppm (J=3.5 Hz), 4.99 ppm, and 4.83 ppm (J=3.6 Hz). $^{13}$C had values of 100.5, 99.2, and 97.0 ppm. The $J_{C1H1}$ coupling was 174.5, 168.4, and 167.0 Hz indicating three α-anomeric linkages. $^1$H nmr of (β-anomer contained two α-anomeric protons based on chemical shift and coupling constant of 5.00 ppm (J=3.5 Hz), and 4.91 ppm and the β-anomeric proton at 4.06 ppm (J=7.1 Hz). $^{13}$C had a value of 99.1 (2C) and 97.0 ppm. The $J_{C1H1}$ coupling was 168.6, and 167.1 Hz indicating two α-anomeric linkages, the β linkage overlapped with one of the α and hence could not be calculated. $[α]_D^{20}$=+71.6° (c=1.06, CHCl$_3$); IR $v_{max}$ (film) 3488, 2923, 2111, 1740, 1694, 1234, 1088, 1040, 747 cm$^{-1}$; $^1$H NMR (400 MHz, CDCl$_3$) δ 7.89 (s, 1H), 7.87-7.78 (m, 5H), 7.78-7.71 (m, 2H), 7.57 (d, J=8.2 Hz, 1H), 7.52-7.42 (m, 5H), 7.41-7.08 (m, 20H), 5.21 (s, 1H), 5.18 (bs, 2H), 5.09 (d, J=3.5 Hz, 1H), 5.00 (bs, 1H), 4.95 (bs, 2H), 4.91 (bs, 2H), 4.83 (d, J=3.7 Hz, 1H), 4.60-4.50 (m, 2H), 4.47 (bs, 2H), 4.34 (s, 1H), 4.17 (q, J=7.4 Hz, 1H), 4.22-4.11 (m, 1H), 4.10-3.85 (m, 6H), 3.83 (dd, J=10.8, 3.2 Hz, 1H), 3.72 (dd, J=10.8, 3.5 Hz, 1H), 3.70-3.50 (m, 5H), 3.41 (bs, 1H), 3.21 (bm, 2H), 3.09 (d, J=11.7 Hz, 1H), 2.47 (s, 1H, OH), 2.23 (s, 1H, OH), 1.59 (bm, 4H), 1.28 (bm, 2H), 1.14 (d, J=6.6 Hz, 3H); $^{13}$C NMR (100 MHz, CDCl$_3$) δ 138.1, 137.8, 137.7, 136.1, 136.0, 133.4 (2C), 133.2, 133.1, 129.2, 128.7 (2C), 128.7, 128.6, 128.4, 128.2, 128.1, 128.0 (2C), 127.9, 127.1, 126.4 (2C), 126.3, 126.1 (2C), 125.9, 125.6, 100.9, 100.5, 99.3, 97.0, 77.5, 77.4 (2C), 77.2, 77.0, 76.9, 75.7, 75.5, 74.1, 73.7, 73.1, 72.6, 71.7, 69.2, 69.0, 68.8, 68.3, 67.4, 67.3, 66.7, 62.4, 61.1, 59.0, 29.3, 23.6, 16.5; HRMS (ESI): Calcd for C$_{74}$H$_{79}$N$_7$O$_{15}$ [M+Na]$^+$1328.5532, found: 1328.5551.

Example 10A: Synthesis of (2S,3S,4S,5S,6S)-5-azido-6-(((2S,4aR,6R,7R,8R,8aR)-7-azido-6-(((2R,3S,4S,5R,6S)-6-((5-(benzyl((benzyloxy)carbonyl)amino)pentyl)oxy)-2-((benzyloxy)methyl)-4,5-bis(naphthalen-2-ylmethoxy)tetrahydro-2H-pyran-3-yl)oxy)-2-phenylhexahydropyrano[3,2-d][1,3]dioxin-8-yl)oxy)-4-hydroxy-2-methyltetrahydro-2H-pyran-3-yl acetate (10*)

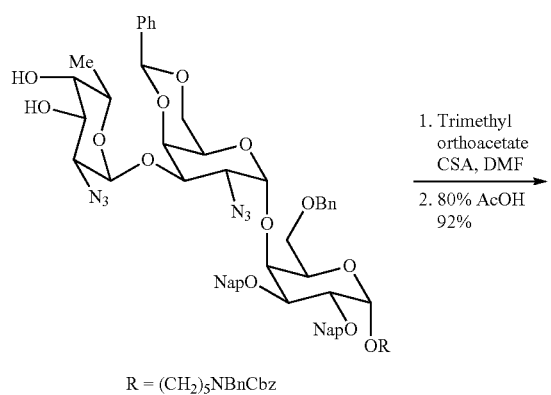

R = (CH$_2$)$_5$NBnCbz

1. Trimethyl orthoacetate CSA, DMF
2. 80% AcOH
92%

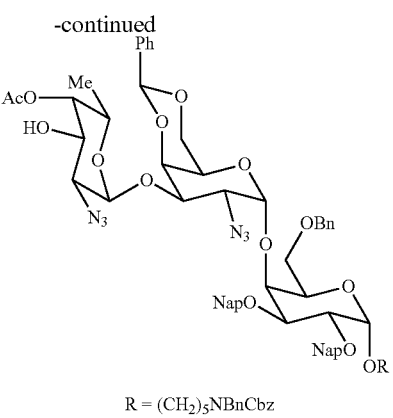

R = (CH$_2$)$_5$NBnCbz

To a solution of the trisaccharide compound 9* (0.65 g, 0.40 mmol) in DMF (2.4 mL) at room temperature was added trimethyl orthoacetate (0.38 mL, 2.99 mmol) and p-TSA (0.014 g, 0.075 mmol) and the reaction mixture stirred for 30 min. Triethylamine (4 drops) was added and the solvent removed under vacuum using toluene as an azeotrop. To the crude was added 80% acetic acid (4.66 mL) and the reaction mixture stirred for 1 h at room temperature. The solvent was removed under vacuum, azeotroped with toluene to obtain oil. Purification by flash column chromatography using hexanes and ethyl acetate as eluent (10 to 50%) afforded the compound 10* as white foam (0.62 g, 92%). $[α]_D^{20}$=+66.5° (c=1.10, CHCl$_3$); IR $v_{max}$ (film) 2925, 2112, 1746, 1697, 1233, 1089, 1042, 746 cm$^{-1}$; $^1$H NMR (400 MHz, CDCl$_3$) δ 7.90 (s, 1H), 7.89-7.79 (m, 5H), 7.76 (dd, J=6.7, 2.6 Hz, 2H), 7.58 (d, J=8.2 Hz, 1H), 7.54-7.43 (m, 5H), 7.42-7.21 (m, 19H), 7.17 (s, 1H), 5.20 (bs, 3H), 5.10 (d, J=3.5 Hz, 1H), 5.08 (dd, J=3.4, 1.2 Hz, 1H), 5.01 (bs, 1H), 4.98-4.89 (m, 4H), 4.83 (d, J=3.7 Hz, 1H), 4.61-4.51 (m, 2H), 4.48 (d, J=6.7 Hz, 2H), 4.35 (s, 1H), 4.26 (q, J=6.4 Hz, 1H), 4.19 (dd, J=10.7, 3.5 Hz, 1H), 4.05 (d, J=3.0 Hz, 1H), 4.04-3.93 (m, 4H), 3.89 (t, J=8.8 Hz, 1H), 3.83 (dd, J=10.8, 3.2 Hz, 1H), 3.72 (dd, J=10.8, 3.4 Hz, 1H), 3.67 (d, J=11.7 Hz, 1H), 3.64-3.50 (m, 3H), 3.42 (bs, 1H), 3.22 (bm, 2H), 3.10 (d, J=11.7 Hz, 1H), 2.22 (s, 3H), 1.57 (bm, 4H), 1.40-1.16 (bm, 2H), 1.00 (d, J=6.6 Hz, 3H); $^{13}$C NMR (100 MHz, CDCl$_3$) δ 171.5, 138.1, 137.7, 136.0 (2C), 133.4 (2C), 133.2, 133.1, 129.3, 128.7, 128.6 (2C), 128.4 (2C), 128.2, 128.1, 128.0 (3C), 127.9, 127.4, 127.1, 126.4, 126.3, 126.1 (2C), 125.9, 125.6, 101.0, 100.5, 99.2, 97.0, 77.4, 77.1, 75.7, 75.5, 74.0, 73.7, 73.1, 72.5, 69.2, 68.9, 68.3, 67.6, 67.3 (2C), 65.8, 62.3, 61.0, 59.0, 29.3, 23.6, 21.0, 16.5; HRMS (ESI): Calcd for C$_{76}$H$_{81}$N$_7$O$_{16}$ [M+Na]$^+$1370.5637, found: 1370.5479.

Example 11A: Synthesis of (2R,4aR,6R,7R,8S, 8aR)-6-(((2S,3R,4S,5S,6S)-3-acetoxy-5-azido-6-(((2S,4aR,6R,7R,8R,8aR)-7-azido-6-(((2R,3S,4S,5R, 6S)-6-((5-(benzyl((benzyloxy)carbonyl)amino) pentyl)oxy)-2-((benzyloxy)methyl)-4,5-bis (naphthalen-2-ylmethoxy)tetrahydro-2H-pyran-3-yl) oxy)-2-phenylhexahydropyrano[3,2-d][1,3]dioxin-8-yl)oxy)-2-methyltetrahydro-2H-pyran-4-yl)oxy)-8-(benzyloxy)-2-phenylhexahydropyrano[3,2-d][1,3] dioxin-7-yl 4-oxopentanoate (11*)

Example 12A: Synthesis of (2S,3R,4S,5S,6S)-5-azido-6-(((2S,4aR,6R,7R,8R,8aR)-7-azido-6-(((2R, 3S,4S,5R,6S)-6-((5-(benzyl((benzyloxy)carbonyl) amino)pentyl)oxy)-2-((benzyloxy)methyl)-4,5-bis (naphthalen-2-ylmethoxy)tetrahydro-2H-pyran-3-yl) oxy)-2-phenylhexahydropyrano[3,2-d][1,3]dioxin-8-yl)oxy)-4-(((2R,4aR,6R,7R,8R,8aR)-8-(benzyloxy)-7-hydroxy-2-phenylhexahydropyrano[3,2-d][1,3] dioxin-6-yl)oxy)-2-methyltetrahydro-2H-pyran-3-yl acetate (12*)

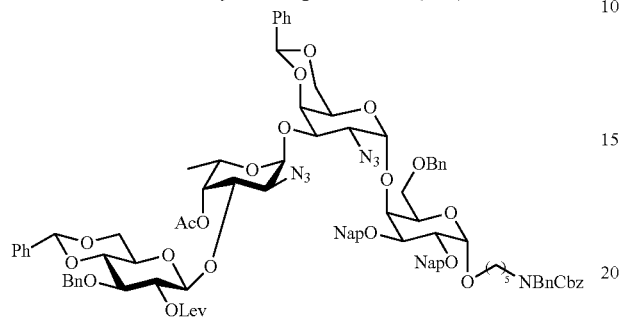

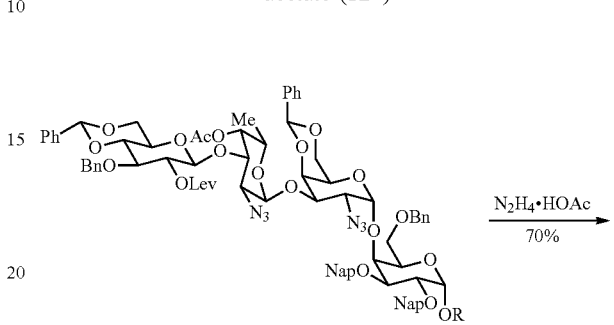

R = (CH$_2$)$_5$NBnCbz

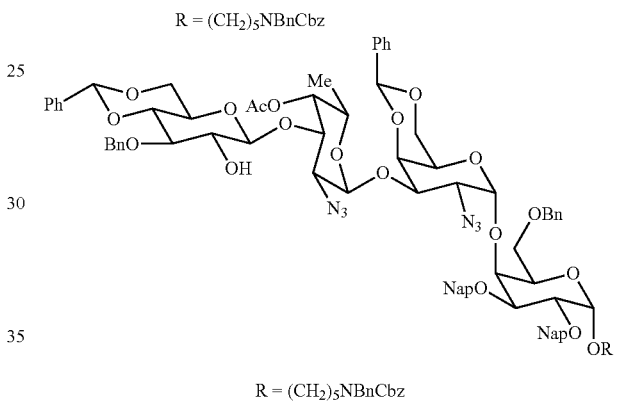

R = (CH$_2$)$_5$NBnCbz

Stirred a solution of acceptor 10* (0.25 g, 0.18 mmol), (2R,4aR,6S,7R,8S,8aR)-8-(benzyloxy)-6-(ethylthio)-2-phenylhexahydropyrano[3,2-d][1,3]dioxin-7-yl 4-oxopentanoate (0.14 g, 0.27 mmol) (dried under vacuum overnight) and activated 4 Å MS (0.39 g) in DCM (2 mL) for 1 h at room temperature. After cooling to −30° C. added NIS (0.063 g, 0.27 mmol) followed by TfOH (8.2 µL, 0.093 mmol) and stirred the reaction mixture for 1 h. Quenched the reaction using 0.05 mL of Et$_3$N. Diluted the RM with DCM and washed the organic layer with sat. aq. Na$_2$S$_2$O$_3$, water, brine, dried over Na$_2$SO$_4$, filtered and concentrated to obtain yellow oil. Purified the crude by flash chromatography using hexanes and ethyl acetate as eluent (10% to 50%) to obtain the compound 11* as white foam (0.22, 66%).

NMR analysis: $^1$H NMR indicated three α- and one β-anomeric protons based on chemical shift and coupling constant at 5.02 ppm (J=3.5 Hz), 4.98 ppm, and 4.70 ppm (J=3.6 Hz) for α and 4.57 ppm (J=7.6 Hz) for β. $^{13}$C indicated a value of 100.8, 99.1 and 97.0 ppm for α and 100.0 for β. The $J_{C1H1}$ coupling was 173.9, 172.0, and 170.6 Hz for three α-anomeric and 164.9 Hz for the β-anomeric linkages. $[α]_D^{20}$=+36.6° (c=0.90, CHCl$_3$); IR $v_{max}$ (film) 2925, 2111, 1746, 1696, 1233, 1089, 1042, 748 cm$^{-1}$; $^1$H NMR (400 MHz, Acetone-d$_6$) δ 8.02-7.73 (m, 8H), 7.64 (d, J=8.1 Hz, 1H), 7.60 (dd, J=8.5, 1.6 Hz, 1H), 7.55-7.20 (m, 34H), 5.71 (s, 1H), 5.36 (s, 1H), 5.25 (d, J=2.6 Hz, 1H), 5.15 (m, 3H), 5.06 (s, 1H), 5.02-4.86 (m, 6H), 4.83 (d, J=6.7 Hz, 1H), 4.80 (d, J=2.6 Hz, 1H), 4.72 (d, J=11.9 Hz, 1H), 4.60 (s, 2H), 4.51 (s, 2H), 4.39 (s, 1H), 4.34 (dd, J=10.9, 3.3 Hz, 1H), 4.30-4.20 (m, 3H), 4.17 (s, 1H), 4.09-3.91 (m, 5H), 3.86-3.70 (m, 4H), 3.71-3.59 (m, 3H), 3.57 (dd, J=10.9, 3.7 Hz, 1H), 3.54-3.38 (m, 2H), 3.33 (dd, J=12.4, 1.4 Hz, 1H), 3.24 (bs, 2H), 2.78-2.64 (m, 2H), 2.64-2.48 (m, 2H), 2.13 (s, 3H), 2.12 (s, 3H), 1.57 (bs, 4H), 1.37 (bs, 2H), 0.98 (d, J=6.5 Hz, 3H); $^{13}$C NMR (100 MHz, Acetone-d$_6$) δ 172.0, 170.9, 139.7 (2C), 139.6, 139.4, 139.0, 137.7, 134.4, 134.3, 134.0, 133.9, 129.8, 129.7, 129.6, 129.3 (2C), 129.2, 129.1, 129.0, 128.9 (2C), 128.8 (2C), 128.7 (2C), 128.6 (2C), 128.5, 128.3, 128.0, 127.5, 127.3, 127.2 (2C), 127.1, 127.0, 126.8, 126.7, 126.5, 126.2, 101.8, 101.6, 101.4, 100.1, 98.0, 82.1, 80.2, 78.3, 78.3, 76.4, 76.3, 75.2, 74.6, 74.2, 74.1, 73.9, 73.1, 72.6, 71.1, 70.0, 69.6, 69.3, 68.6, 67.5, 66.8, 66.7, 63.4, 60.3, 59.7, 38.2, 30.0, 29.9, 28.7, 24.2, 20.8, 16.8; HRMS (ESI): Calcd for C$_{101}$H$_{107}$N$_7$O$_{23}$ [M+Na]$^+$1808.7316, found: 1808.7196.

Compound 11* (0.18 g, 0.10 mmol) was dissolved in a mixture of toluene, ethanol and DCM (2:1:0.5; 3.6 mL:1.8 mL:0.9 mL). Hydrazine acetate (0.046 g, 0.50 mmol) was then added. After 30 min at room temperature diluted the reaction with water and extracted the aqueous with ether. Washed the organic layer with brine, dried over Na$_2$SO$_4$, filtered, and concentrated to obtain oil. Purified the crude by flash chromatography using hexanes and ethyl acetate as eluent, (0 to 30%) to obtain the compound 12* as oil (0.12 g, 70%). $[α]_D^{20}$=+42.0° (c=1.00, CHCl$_3$); IR $v_{max}$ (film) 3494, 2869, 2111, 1730, 1695, 1234, 1088, 1041, 746 cm$^{-1}$; $^1$H NMR (400 MHz, Acetone-d$_6$) δ 8.04-7.73 (m, 8H), 7.64 (d, J=8.0 Hz, 1H), 7.60 (dd, J=8.5, 1.6 Hz, 1H), 7.56-7.07 (m, 34H), 5.66 (s, 1H), 5.38 (s, 1H), 5.34 (d, J=2.5 Hz, 1H), 5.16 (d, J=3.1 Hz, 3H), 5.06 (s, 1H), 5.02-4.88 (m, 5H), 4.86 (q, J=12.0 Hz, 2H), 4.62 (s, 1H), 4.61 (s, 2H), 4.51 (s, 2H), 4.41 (s, 1H), 4.38 (dd, J=10.9, 3.3 Hz, 1H), 4.33 (q, J=6.1 Hz, 1H), 4.28 (d, J=2.7 Hz, 1H), 4.24-4.17 (m, 2H), 4.14 (d, J=4.0 Hz, 1H), 4.10-3.93 (m, 5H), 3.83-3.71 (m, 2H), 3.70-3.55 (m, 6H), 3.49-3.38 (m, 3H), 3.34 (dd, J=12.4, 1.5 Hz, 1H), 3.24 (bs, 2H), 2.17 (s, 3H), 1.57 (bs, 4H), 1.42-1.24 (bs, 2H), 1.03 (d, J=6.5 Hz, 3H); $^{13}$C NMR (100 MHz, Acetone-d$_6$) δ 171.0, 139.5, 138.8, 138.7, 138.5, 138.3, 136.8 (2C), 133.5, 133.4, 133.1, 133.0, 128.7, 128.6, 128.4 (2C), 128.3, 128.0 (2C), 127.9 (3C), 127.8, 127.7 (2C), 127.6, 127.5, 127.1, 126.6, 126.4, 126.3, 126.2 (2C), 126.1, 125.9, 125.8, 125.6, 101.5, 101.0, 100.7, 100.5, 99.2, 97.1, 81.3, 81.1, 77.4, 77.2, 75.6, 75.4, 74.7, 74.6, 74.2, 74.0, 73.5, 73.0, 72.3, 71.7, 70.2, 69.1, 68.7, 68.5, 67.7, 66.6, 66.2, 65.7, 62.6, 59.2, 59.02, 29.1, 23.3, 20.1, 15.9; HRMS (ESI): Calcd for C$_{96}$H$_{101}$N$_7$O$_{21}$ [M+Na]$^+$1710.6948, found: 1710.6809.

Example 13A: Synthesis of (2S,3R,4S,5S,6S)-5-azido-6-(((2S,4aR,6R,7R,8R,8aR)-7-azido-6-(((2R,3S,4S,5R,6S)-6-((5-(benzyl((benzyloxy)carbonyl)amino)pentyl)oxy)-2-((benzyloxy)methyl)-4,5-bis(naphthalen-2-ylmethoxy)tetrahydro-2H-pyran-3-yl)oxy)-2-phenylhexahydropyrano[3,2-d][1,3]dioxin-8-yl)oxy)-4-(((2R,4aR,6R,7S,8R,8aS)-7-azido-8-(benzyloxy)-2-phenylhexahydropyrano[3,2-d][1,3]dioxin-6-yl)oxy)-2-methyltetrahydro-2H-pyran-3-yl acetate (13*)

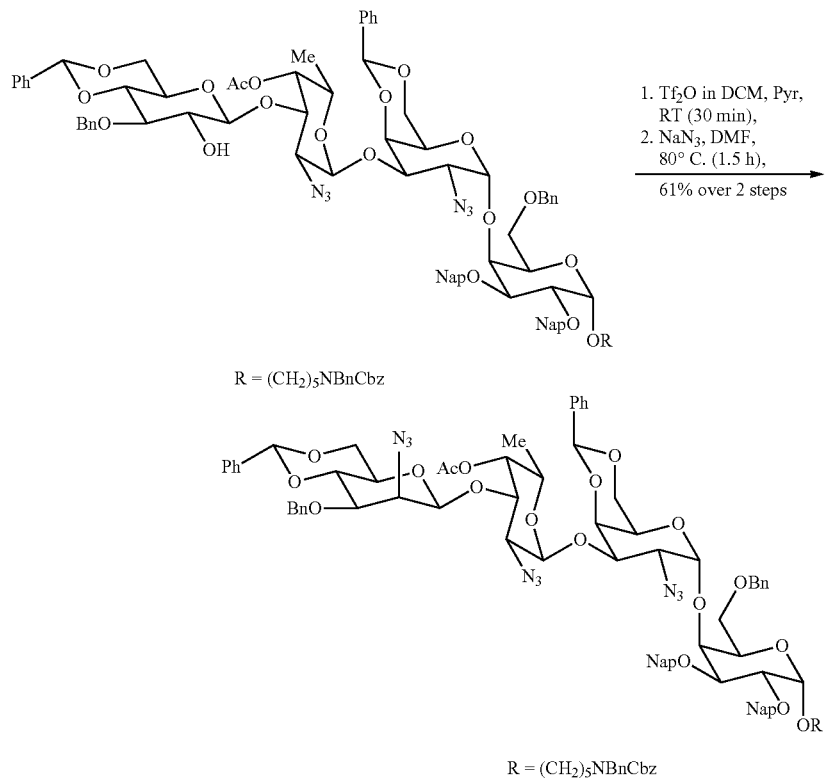

To a solution of compound 12* (0.05 g, 0.03 mmol) in DCM (0.6 mL) was added pyridine (0.06 mL, 0.74 mmol) followed by a 1.0 M solution of triflic anhydride in DCM (0.089 mL, 0.089 mmol) and stirred the reaction mixture at room temperature for 30 min. Quenched the reaction with sat. aq. NaHCO$_3$ and extracted the aqueous with DCM, washed with brine, dried over Na$_2$SO$_4$, filtered, and concentrated to obtain oil which was dried on high vacuum for 2 h. The crude was then taken in DMF (0.6 mL), added NaN$_3$ (0.0057 g, 0.089 mmol) and heated the reaction to 80° C. for 1.5 h. After cooling to room temperature, diluted the reaction with sat. aq. NH$_4$Cl and extracted the aqueous layer with ethyl acetate. Washed the organic layer with brine, dried over Na$_2$SO$_4$, filtered, and concentrated to obtain oil. Purified the crude by flash chromatography using hexanes and ethyl acetate as eluent (0 to 40%) to obtain the compound 13* as white foam (0.031 g, 61%).

NMR analysis: $^1$H NMR showed a coupling constant of J=1.1 Hz for the β-mannoside linkage which before inversion was 7.2 Hz.

[α]$_D^{20}$=+21.0° (c=1.50, CHCl$_3$); IR ν$_{max}$ (film) 2916, 2860, 2112, 1737, 1697, 1234, 1088, 1045, 746 cm$^{-1}$; $^1$H NMR (400 MHz, Acetone-d$_6$) δ 8.01-7.76 (m, 8H), 7.64 (d, J=8.6 Hz, 1H), 7.60 (dd, J=8.5, 1.5 Hz, 1H), 7.55-7.17 (m, 34H), 5.68 (s, 1H), 5.36 (s, 1H), 5.30 (d, J=3.3 Hz, 1H), 5.15 (d, J=3.4 Hz, 3H), 5.07 (s, 1H), 5.02 (d, J=1.3 Hz, 1H), 5.01-4.90 (m, 5H), 4.82 (d, J=12.2 Hz, 1H), 4.74 (d, J=12.2 Hz, 1H), 4.60 (s, 2H), 4.51 (s, 2H), 4.40 (s, 1H), 4.37 (dd, J=10.9, 3.3 Hz, 1H), 4.35-4.23 (m, 2H), 4.17 (s, 1H), 4.14 (dd, J=10.4, 4.9 Hz, 1H), 4.09-3.94 (m, 6H), 3.93-3.83 (m, 2H), 3.79 (t, J=10.3 Hz, 1H), 3.74 (dd, J=10.9, 3.4 Hz, 1H), 3.63 (m, 3H), 3.55 (dd, J=10.9, 3.7 Hz, 1H), 3.51-3.36 (m, 2H), 3.33 (d, J=11.0 Hz, 1H), 3.24 (bs, 2H), 2.16 (s, 3H), 1.57 (bs, 4H), 1.36 (bs, 2H), 1.04 (d, J=6.5 Hz, 3H); $^{13}$C NMR (100 MHz, Acetone-d$_6$) δ 171.5, 139.7, 139.6 (2C), 139.4, 139.1, 137.7 (2C), 134.4, 134.3, 134.0, 133.9, 129.7, 129.6, 129.3 (2C), 129.2, 129.1, 128.9 (3C), 128.8, 128.7, 128.6 (2C), 128.5, 128.4, 128.0, 127.5, 127.3, 127.2, 127.1, 127.0, 126.8, 126.7, 126.5, 102.2, 101.5 (2C), 100.2, 98.7, 98.0, 79.2, 78.3, 78.2, 77.7, 76.5, 76.3, 75.1, 74.3, 73.9, 73.2, 73.1, 72.6, 70.8, 69.9, 69.6, 69.1, 68.6, 68.0, 67.5, 66.2, 64.7, 63.4, 60.1, 59.7, 30.0, 24.2, 20.9, 16.7; HRMS (ESI): Calcd for C$_{96}$H$_{100}$N$_{10}$O$_{20}$ [M+Na]$^+$1735.7013, found: 1735.6995.

Example 14A: Synthesis of (2S,3R,4S,5S,6S)-5-acetamido-6-(((2S,4aR,6R,7R,8R,8aR)-7-acetamido-6-(((2R,3S,4S,5R,6S)-6-((5-(benzyl((benzyloxy)carbonyl)amino)pentyl)oxy)-2-((benzyloxy)methyl)-4,5-bis(naphthalen-2-ylmethoxy)tetrahydro-2H-pyran-3-yl)oxy)-2-phenylhexahydropyrano[3,2-d][1,3]dioxin-8-yl)oxy)-4-(((2R,4aR,6R,7S,8R,8aS)-7-acetamido-8-(benzyloxy)-2-phenylhexahydropyrano[3,2-d][1,3]dioxin-6-yl)oxy)-2-methyltetrahydro-2H-pyran-3-yl acetate (14*)

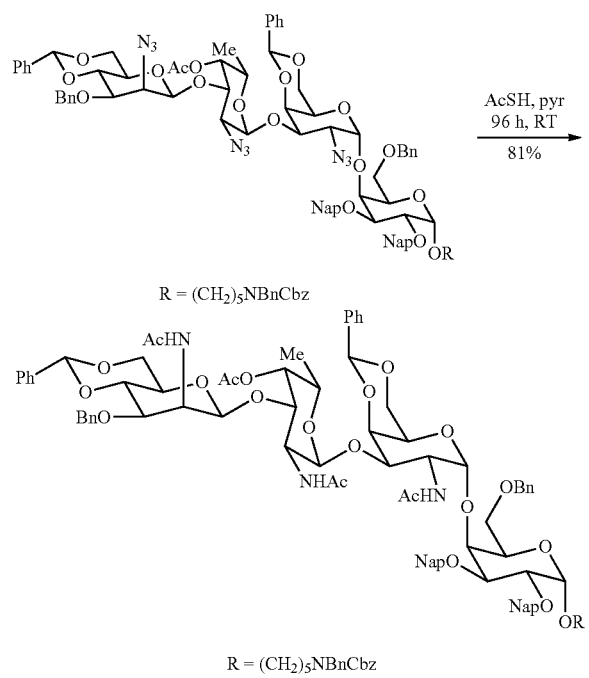

To a solution of compound 13* (0.03 g, 0.018 mmol) in pyridine (0.5 mL) was added thioacetic acid (0.15 mL, 2.18 mmol) and the reaction stirred at room temperature for 96 h. (Since the reaction was not able to be monitored by TLC, LC-MS was taken after 48 h and it showed the presence of diacetamide. Added further 0.07 mL of thioacetic acid and continued stirring for additional 48 h (LC-MS showed no starting material or mono- or diacetamide). The solvent were removed under vacuo and the crude azeotroped twice with toluene. Purified the crude by flash chromatography using DCM, acetone and MeOH as eluent (5% each of MeOH and acetone up to 50%) to obtain the compound 14* as foam (0.025 g, 81%). $[\alpha]_D^{20}$=+28.0° (c=1.38, CHCl$_3$); IR v$_{max}$ (film) 3434, 2934, 2860, 1738, 1674, 1234, 1093, 1045, 749 cm$^{-1}$; $^1$H NMR (400 MHz, Acetone-d$_6$) δ 7.89 (m, 8H), 7.74 (d, J=7.9 Hz, 1H), 7.65-7.54 (m, 2H), 7.55-7.14 (m, 34H), 6.47 (d, J=9.8 Hz, 1H), 6.24 (d, J=9.1 Hz, 1H), 5.55 (s, 1H), 5.44 (s, 1H), 5.24 (d, J=2.5 Hz, 1H), 5.14 (s, 2H), 5.10 (d, J=3.6 Hz, 1H), 5.06-4.94 (m, 5H), 4.90 (d, J=12.7 Hz, 1H), 4.81 (d, J=1.7 Hz, 1H), 4.77 (d, J=11.9 Hz, 1H), 4.74-4.66 (m, 1H), 4.57 (d, J=11.7 Hz, 1H), 4.53-4.45 (m, 5H), 4.41 (s, 1H), 4.39-4.28 (m, 3H), 4.28-4.22 (m, 1H), 4.20 (dd, J=10.0, 4.7 Hz, 1H), 4.11 (dd, J=10.3, 3.4 Hz, 1H), 4.08-3.97 (m, 4H), 3.84 (t, J=9.6 Hz, 1H), 3.79-3.52 (m, 6H), 3.40 (m, 3H), 3.22 (s, 2H), 2.13 (s, 3H), 1.96 (s, 3H), 1.94 (s, 3H), 1.94 (s, 3H), 1.56 (bs, 4H), 1.41-1.30 (m, 2H), 1.14 (d, J=6.5 Hz, 3H); $^{13}$C NMR (100 MHz, Acetone-d$_6$) δ 171.6, 171.0, 170.4 (2C), 139.8 (2C), 139.5, 139.3, 139.2, 137.8, 137.6, 134.3 (2C), 134.0, 133.9, 129.5, 129.3, 129.2, 129.2, 128.9, 128.8 (4C), 128.7, 128.6 (4C), 128.5 (2C), 128.0 (2C), 127.2, 127.1, 127.0, 126.9, 126.8, 126.6, 126.4 (2C), 102.2, 101.9, 101.4, 100.0, 98.4, 98.2, 79.1, 78.6, 77.3, 76.9, 76.7 (2C), 73.8, 73.7, 73.0 (2C), 71.3, 70.5, 70.2, 69.8, 69.2, 68.7 (2C), 68.0, 67.4, 65.8, 63.3, 50.8, 49.6, 49.4, 30.0, 24.2, 23.8, 23.7, 23.2, 20.8, 16.9; HRMS (ESI): Calcd for C$_{102}$H$_{112}$N$_4$O$_{23}$ [M+Na]$^+$1783.7615, found: 1783.7609.

Example 15A: Synthesis of benzyl (5-(((2S,3R,4S,5S,6R)-5-(((2S,4aR,6R,7R,8R,8aR)-7-acetamido-8-(((2S,3S,4S,5R,6S)-3-acetamido-4-(((2R,4aR,6R,7S,8R,8aS)-7-acetamido-8-(benzyloxy)-2-phenylhexahydropyrano[3,2-d][1,3]dioxin-6-yl)oxy)-5-hydroxy-6-methyltetrahydro-2H-pyran-2-yl)oxy)-2-phenylhexahydropyrano[3,2-d][1,3]dioxin-6-yl)oxy)-6-((benzyloxy)methyl)-3,4-bis(naphthalen-2-ylmethoxy)tetrahydro-2H-pyran-2-yl)oxy)pentyl)(benzyl)carbamate (15*)

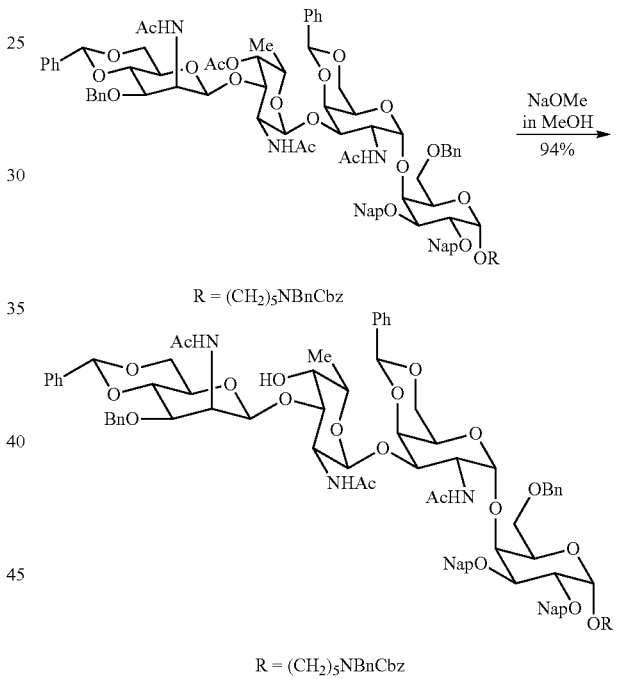

To a solution of compound 14*(0.021 g, 0.012 mmol) in MeOH (0.45 mL) was added a solution of 0.5 M NaOMe in MeOH (5.96 µL, 2.98 µmol) and the reaction stirred for 2.5 h at room temperature. Diluted the reaction with MeOH, neutralized with Amberlite 120 H$^+$ resin, filtered, and concentrated to obtain the compound 15* as foam (0.0193 g, 94%). $[\alpha]_D^{20}$=+49.1° (c=1.90, CHCl$_3$); IR v$_{max}$ (film) 3354, 2929, 2860, 1667, 1372, 1096, 1045, 751 cm$^{-1}$; $^1$H NMR (400 MHz, Acetone-d$_6$) δ 8.02-7.78 (m, 8H), 7.73 (d, J=7.9 Hz, 1H), 7.63-7.53 (m, 2H), 7.53-7.17 (m, 34H), 7.10 (d, J=9.5 Hz, 1H), 6.46 (d, J=9.1 Hz, 1H), 5.56 (s, 1H), 5.42 (s, 1H), 5.14 (s, 2H), 5.10 (d, J=3.6 Hz, 1H), 5.05-4.81 (m, 9H), 4.78-4.68 (m, 1H), 4.61-4.45 (m, 6H), 4.45-4.25 (m, 4H), 4.20 (d, J=10.1, 4.8 Hz, 1H), 4.17 (d, J=6.5 Hz, 1H), 4.13 (dd, J=10.3, 3.6 Hz, 1H), 4.09-3.97 (m, 3H), 3.94 (d, J=9.9 Hz, 1H), 3.91-3.82 (m, 2H), 3.75 (d, J=10.1 Hz, 1H), 3.73-3.52 (m, 5H), 3.50-3.29 (m, 4H), 3.21 (s, 3H), 1.98 (s, 3H), 1.96 (s, 3H), 1.94 (s, 3H), 1.55 (bs, 4H), 1.39-1.30 (m, 2H), 1.26 (d, J=6.6 Hz, 3H); $^{13}$C NMR (100 MHz, Acetone-d$_6$) δ 172.4, 170.5, 170.4, 139.9, 139.8, 139.5, 139.3, 139.1, 137.8, 137.6, 134.3 (2C), 134.0, 133.8, 130.3, 130.0, 129.6, 129.5, 129.3, 129.2 (3C), 129.0, 128.9, 128.8 (2C), 128.7 (2C), 128.6 (3C), 128.5, 128.4 (2C), 128.1, 128.0, 127.1 (3C), 127.0, 126.9, 126.8, 126.6, 126.4, 102.2, 102.0, 101.3, 100.0, 99.4 (2C), 79.0, 78.6, 78.1, 77.0, 76.8, 76.7, 74.6, 73.7, 73.1, 73.0, 71.4, 70.2, 69.9, 69.6, 69.2, 68.7, 68.6, 68.0, 67.4, 67.3, 63.3, 51.8, 49.5, 48.7, 24.2, 23.6 (2C), 23.2, 17.2; HRMS (ESI): Calcd for $C_{100}H_{110}N_4O_{22}$ [M+Na]$^+$ 1741.7509, found: 1741.7503.

Example 16A: Synthesis of N-((2R,3S,4R,5S,6R)-2-(((2S,3S,4S,5R,6S)-3-acetamido-2-(((2R,3R,4R,5R,6R)-3-acetamido-2-(((2R,3R,4R,5R,6S)-6-((5-aminopentyl)oxy)-4,5-dihydroxy-2-(hydroxymethyl)tetrahydro-2H-pyran-3-yl)oxy)-5-hydroxy-6-(hydroxymethyl)tetrahydro-2H-pyran-4-yl)oxy)-5-hydroxy-6-methyltetrahydro-2H-pyran-4-yl)oxy)-4,5-dihydroxy-6-(hydroxymethyl)tetrahydro-2H-pyran-3-yl)acetamide (16*)

LCMS showed only compound. Washed the crude with hexanes and decanted followed by acetone and decantation to obtain the compound 16* as foam (0.0075 g, 79%). [α]$_D^{20}$=+33.3° (c=0.56, H$_2$O); IR v$_{max}$ (film) 3354, 2929, 2860, 1667, 1372, 1096, 1045, 751 cm$^{-1}$; $^1$H NMR (400 MHz, d$_2$o) δ 5.10 (d, J=2.3 Hz, 1H), 5.05 (d, J=2.5 Hz, 1H), 4.94 (s, 1H), 4.90 (d, J=3.8 Hz, 1H), 4.53-4.48 (m, 2H), 4.45 (dd, J=11.2, 3.7 Hz, 1H), 4.24 (s, 2H), 4.18-4.07 (m, 4H), 4.07-3.92 (m, 5H), 3.93-3.82 (m, 2H), 3.82-3.68 (m, 5H), 3.67-3.52 (m, 2H), 3.46-3.39 (m, 1H), 3.06 (t, J=8.0 Hz, 2H) 2.10 (s, 3H), 2.09 (s, 3H), 2.08 (s, 3H), 1.79-1.66 (m, 4H), 1.56-1.46 (m, 2H), 1.30 (d, J=6.5 Hz, 3H); $^{13}$C NMR (100 MHz, d$_2$o) δ 175.4, 173.6 (2C), 98.7, 98.3, 98.2, 95.2, 77.2, 76.3, 73.2, 72.6, 71.7, 71.5, 70.3, 69.0, 68.1 (2C), 67.9, 67.6, 66.8 (2C), 60.4, 60.3, 60.2, 53.3, 49.0, 47.6, 39.3, 27.9, 26.4, 22.3, 22.1, 21.9, 21.8, 15.4; HRMS (ESI): Calcd for $C_{35}H_{62}N_4O_{20}$ [M+Na]$^+$ 881.3855, found: 881.3790.

General Procedures for the Preparation of Deletion Sequences:

Procedure A. Deacylation:

To a solution of compound in MeOH (0.06 mL) was added a solution of 0.5 M NaOMe in MeOH (0.013 mL, 6.37

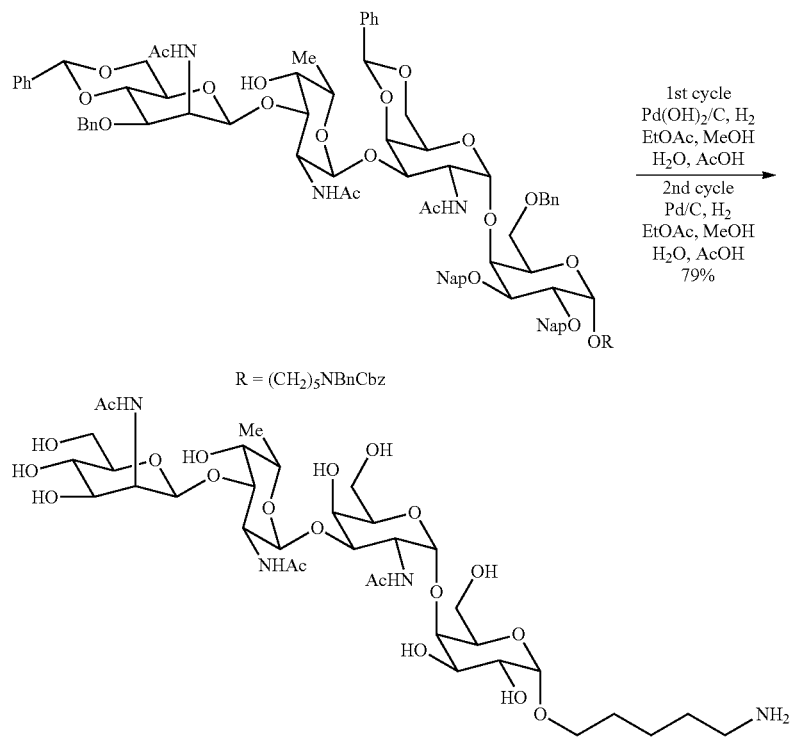

To compound 15* (0.019 g, 0.011 mmol) was added MeOH, water, ethyl acetate and acetic acid (3:1:1:0.1-0.3 mL:0.1 mL:10 µL). Purged the reaction mixture before and after addition of Pd(OH)$_2$ (20%) (0.036 g, 0.052 mmol) with argon for 2-3 min. The reaction mixture was purged with hydrogen and stirred for 24 h under an atmosphere of hydrogen. Filtered off palladium over celite, washed with methanol and 1:1 mixture of MeOH and water, concentrated the filtrate to obtain oil. (LCMS at this point showed no starting material, but only partially debenzylated compounds). Resubjected the crude for a second cycle with the same solvent combination, Pd/C (0.036 g, 10% Pd; 50% water) stirred for 20 h. Filtration as above, followed by µmol) and the reaction mixture stirred for 2 h at room temperature. Diluted the reaction mixture with MeOH, neutralized with Amberlite 120 H$^+$ resin, filtered and concentrated.

Procedure B. Conversion azide to N-acetamide:

To a solution of compound in pyridine (0.6 mL) was added thioacetic acid (0.091 mL, 1.27 mmol) and the reaction mixture stirred at room temperature for 18 h. Removed the solvents under vacuo and azeotroped the reaction mixture twice with toluene to obtain the crude as yellow oil. Purified the crude by flash chromatography using DCM and EtOAc as eluent (0 to 20%).

Procedure C. Global Deprotection:

Dissolved the compound in a mixture of MeOH, water, ethyl acetate and acetic acid (3:1:1:0.1-0.3 mL: 0.1 mL:0.1 mL:10 μL). Purged the reaction mixture before and after addition of Pd(OH)$_2$ (20%) with argon for 2-3 min. The reaction mixture was then purged with hydrogen and stirred for 24 h under an atmosphere of hydrogen. Filtered off palladium over celite, washed with methanol and 1:1 mixture of MeOH and water, and concentrated the filtrate Resubjected the crude for a second cycle with the same solvent combination, Pd/C (10% Pd; 50% water) stirred for 20 h. Filtration as above and washed the crude with hexanes and decanted. Washed the crude with acetone and decantation to obtain the compound as foam after drying.

Example 17A: Synthesis of N-((2S,3R,4R,5R,6R)-2-(((2R,3R,4R,5R,6S)-6-((5-aminopentyl)oxy)-4,5-dihydroxy-2-(hydroxymethyl)tetrahydro-2H-pyran-3-yl)oxy)-4,5-dihydroxy-6-(hydroxymethyl)tetrahydro-2H-pyran-3-yl)acetamide (17*)

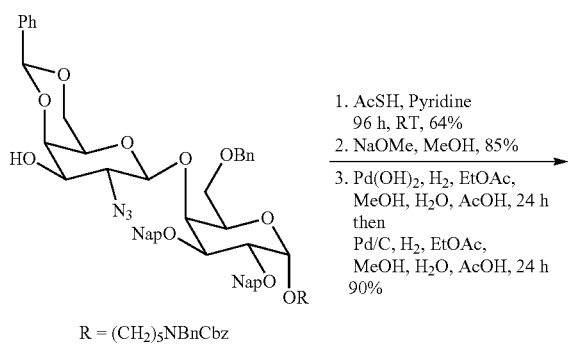

R = (CH$_2$)$_5$NBnCbz

1. AcSH, Pyridine
   96 h, RT, 64%
2. NaOMe, MeOH, 85%
3. Pd(OH)$_2$, H$_2$, EtOAc, MeOH, H$_2$O, AcOH, 24 h then Pd/C, H$_2$, EtOAc, MeOH, H$_2$O, AcOH, 24 h 90%

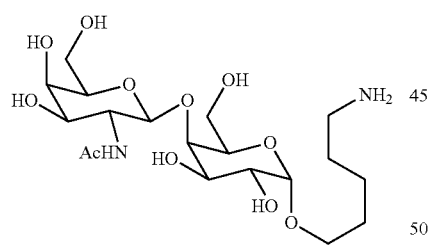

Following general procedures B, A and C the n-disaccharide deletion sequence 17* was obtained. $^1$H NMR (400 MHz, d$_2$o) δ 4.94 (d, J=3.8 Hz, 1H), 4.64 (d, J=8.3 Hz, 1H), 4.15 (s, 1H), 3.98-3.89 (m, 4H), 3.87-3.65 (m, 8H), 3.62-3.47 (m, 1H), 3.03 (t, J=7.4 Hz, 2H), 2.08 (s, 3H), 1.78-1.63 (m, 4H), 1.53-1.42 (m, 2H); $^{13}$C NMR (100 MHz, d$_2$o) δ 174.9, 102.6, 98.2, 76.9, 74.7, 70.8, 70.1, 69.3, 68.4, 67.8, 67.7, 61.0, 60.6, 52.5, 39.2, 27.9, 26.3 (2C), 22.2; HRMS (ESI): Calcd for C$_{19}$H$_{36}$N$_2$O$_{11}$ [M+H]$^+$469.2397, found: 469.2383.

Example 18A: Synthesis of N-((2R,3R,4R,5R,6R)-2-(((2R,3R,4R,5R,6S)-6-((5-aminopentyl)oxy)-4,5-dihydroxy-2-(hydroxymethyl)tetrahydro-2H-pyran-3-yl)oxy)-4,5-dihydroxy-6-(hydroxymethyl)tetrahydro-2H-pyran-3-yl)acetamide (18*)

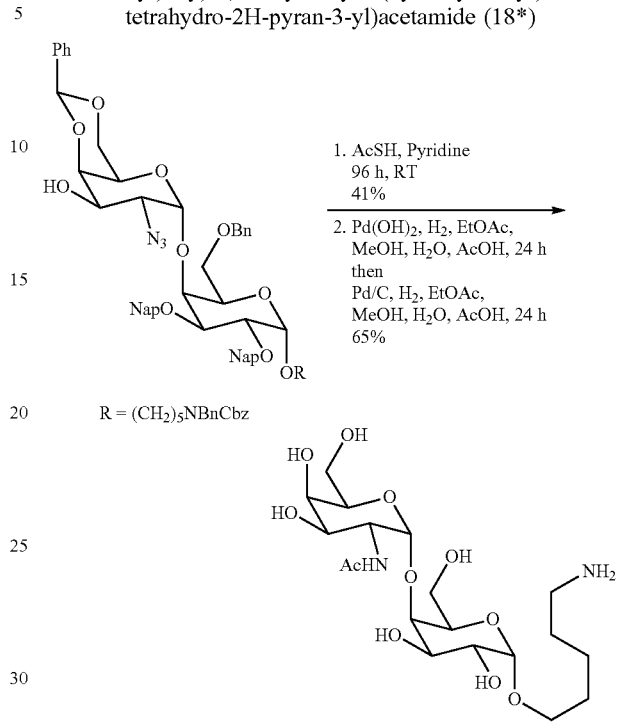

R = (CH$_2$)$_5$NBnCbz

1. AcSH, Pyridine
   96 h, RT
   41%
2. Pd(OH)$_2$, H$_2$, EtOAc, MeOH, H$_2$O, AcOH, 24 h then Pd/C, H$_2$, EtOAc, MeOH, H$_2$O, AcOH, 24 h 65%

Following general procedures B, and C the n-disaccharide deletion sequence 18* was obtained $^1$H NMR (400 MHz, d$_2$o) δ 4.83 (d, J=2.9 Hz, 1H), 4.76 (d, J=3.3 Hz, 1H), 4.22 (t, J=6.3 Hz, 1H), 4.03 (dd, J=11.2, 3.7 Hz, 1H), 3.94-3.66 (m, 5H), 3.66-3.48 (m, 5H), 3.51-3.32 (m, 2H), 2.85 (t, J=7.5 Hz, 2H), 1.92 (s, 3H), 1.63-1.46 (m, 4H), 1.38-1.20 (m, 2H); $^{13}$C NMR (100 MHz, d$_2$o) δ 174.3, 98.2, 98.1, 77.8, 71.6, 70.7, 69.0, 68.2, 68.1, 67.8, 67.0, 60.5, 60.4, 50.1, 39.3, 27.9, 26.4, 22.3, 21.8; HRMS (ESI): Calcd for C$_{19}$H$_{36}$N$_2$O$_{11}$ [M+H]$^+$469.2397, found: 469.2383.

Example 19A: Synthesis of N-((2R,3S,4S,5S,6S)-2-(((2R,3R,4R,5R,6R)-3-acetamido-2-(((2R,3R,4R,5R,6S)-6-((5-aminopentyl)oxy)-4,5-dihydroxy-2-(hydroxymethyl)tetrahydro-2H-pyran-3-yl)oxy)-5-hydroxy-6-(hydroxymethyl)tetrahydro-2H-pyran-4-yl)oxy)-4,5-dihydroxy-6-methyltetrahydro-2H-pyran-3-yl)acetamide (19*)

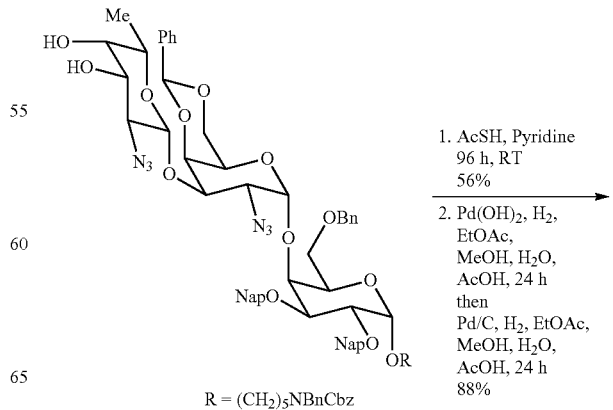

R = (CH$_2$)$_5$NBnCbz

1. AcSH, Pyridine
   96 h, RT
   56%
2. Pd(OH)$_2$, H$_2$, EtOAc, MeOH, H$_2$O, AcOH, 24 h then Pd/C, H$_2$, EtOAc, MeOH, H$_2$O, AcOH, 24 h 88%

95

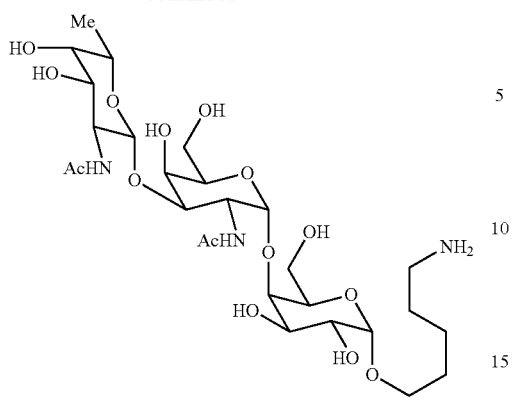

Following general procedures B, and C the β-trisaccharide deletion sequence 19* was obtained $^1$H NMR (400 MHz, d$_2$o) δ 4.90 (d, J=3.8 Hz, 1H), 4.88 (d, J=4.0 Hz, 1H), 4.48 (d, J=7.4 Hz, 1H), 4.23 (t, J=6.4 Hz, 1H), 4.13 (dd, J=11.2, 3.7 Hz, 1H), 4.06-3.87 (m, 4H), 3.80 (ddd, J=14.2, 10.6, 3.1 Hz, 2H), 3.73-3.55 (m, 9H), 3.53-3.38 (m, 1H), 2.93-2.89 (m, 2H), 1.98 (s, 3H), 1.95 (s, 3H), 1.68-1.49 (m, 4H), 1.48-1.28 (m, 2H), 1.21 (d, J=6.4 Hz, 3H); $^{13}$C NMR (100 MHz, d$_2$o) δ 174.9, 174.3, 100.6, 98.4, 98.2, 78.2, 75.7, 71.6, 71.0, 70.8, 70.6, 70.4, 69.0, 68.3, 67.9, 66.3, 60.5, 60.2, 52.5, 48.9, 39.3, 28.0, 26.4, 22.3, 22.2, 22.1, 15.6; HRMS (ESI): Calcd for C$_{27}$H$_{49}$N$_3$O$_{15}$ [M+Na]$^+$ 678.3061, found: 678.3003.

Example 20A: Synthesis of N-((2S,3S,4S,5S,6S)-2-(((2R,3R,4R,5R,6R)-3-acetamido-2-(((2R,3R,4R,5R,6S)-6-((5-aminopentyl)oxy)-4,5-dihydroxy-2-(hydroxymethyl)tetrahydro-2H-pyran-3-yl)oxy)-5-hydroxy-6-(hydroxymethyl)tetrahydro-2H-pyran-4-yl)oxy)-4,5-dihydroxy-6-methyltetrahydro-2H-pyran-3-yl)acetamide (20*)

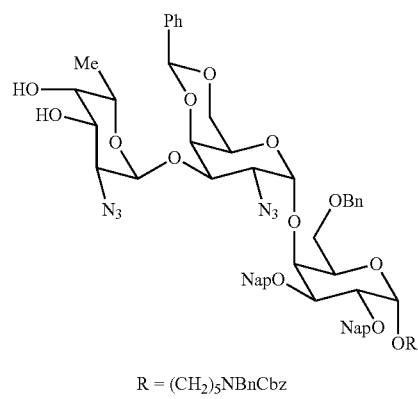

R = (CH$_2$)$_5$NBnCbz

1. AcSH, Pyridine 96 h, RT, 72%
2. Pd(OH)$_2$, H$_2$, EtOAc, MeOH, H$_2$O, AcOH, 24 h then Pd/C, H$_2$, EtOAc, MeOH, H$_2$O, AcOH, 24 h 88%

96

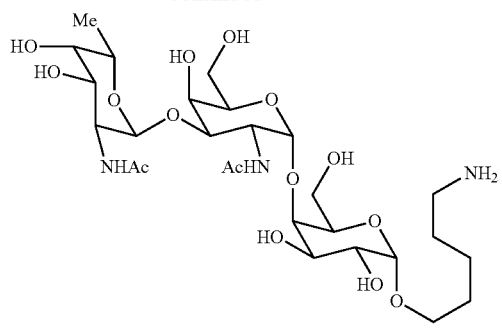

Following general procedures B, and C the α-disaccharide deletion sequence 20* was obtained $^1$H NMR (400 MHz, d$_2$o) δ 4.94 (d, J=3.8 Hz, 1H), 4.90 (d, J=2.2 Hz, 1H), 4.75 (d, J=3.8 Hz, 1H), 4.36 (t, J=5.9 Hz, 1H), 4.30 (dd, J=11.1, 3.7 Hz, 1H), 4.06-4.00 (m, 2H), 3.96 (d, J=8.2 Hz, 2H), 3.93-3.78 (m, 5H), 3.74 (d, J=2.5 Hz, 1H), 3.71-3.52 (m, 5H), 3.51-3.38 (m, 1H), 2.91 (t, J=7.5 Hz, 2H), 1.94 (s, 6H), 1.69-1.49 (m, 4H), 1.46-1.25 (m, 2H), 1.14 (d, J=6.5 Hz, 3H); $^{13}$C NMR (100 MHz, d$_2$o) δ 174.1, 173.6, 98.5, 98.2 (2C), 77.2, 72.9, 71.5, 70.9, 70.4, 69.0, 68.2, 68.1, 67.9, 67.5, 67.1, 60.4, 60.2, 49.4, 49.1, 39.3, 27.9, 26.4, 22.3, 22.1, 21.9, 15.3; HRMS (ESI): Calcd for C$_{27}$H$_{49}$N$_3$O$_{15}$ [M+Na]$^+$ 678.3061, found: 678.3068.

Example 21A: Synthesis of N-((2S,3S,4S,5S,6S)-2-((5-aminopentyl)oxy)-4,5-dihydroxy-6-methyltetrahydro-2H-pyran-3-yl)acetamide (21*)

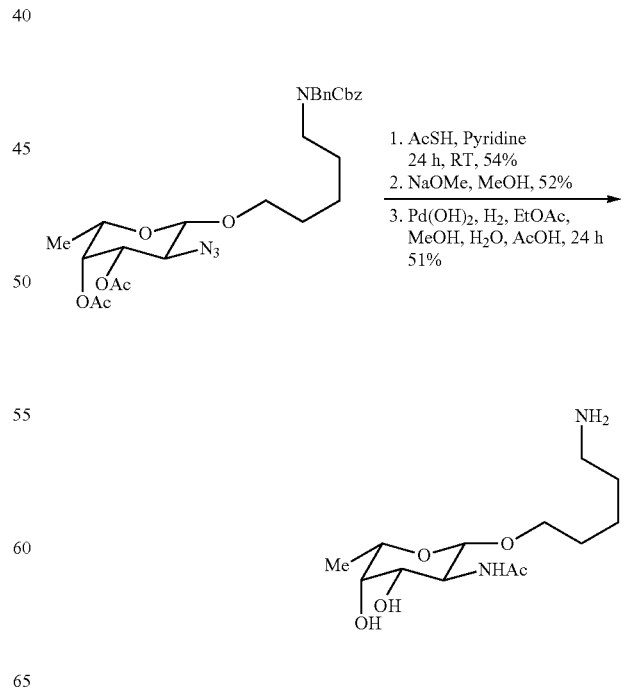

1. AcSH, Pyridine 24 h, RT, 54%
2. NaOMe, MeOH, 52%
3. Pd(OH)$_2$, H$_2$, EtOAc, MeOH, H$_2$O, AcOH, 24 h 51%

Following general procedures B, A, and C the FucNAc deletion sequence 21* was obtained ¹H NMR (400 MHz, CD₃OD) δ 4.20 (d, J=8.4 Hz, 1H), 3.85-3.67 (m, 2H), 3.56-3.42 (m, 3H), 3.43-3.31 (m, 1H), 3.21 (dt, J=3.1, 1.4 Hz, 1H), 2.80 (t, J=7.5 Hz, 2H), 1.88 (s, 3H), 1.65-1.44 (m, 4H), 1.44-1.26 (m, 2H), 1.17 (d, J=6.4 Hz, 3H); ¹³C NMR (100 MHz, CD₃OD) δ 174.2, 103.2, 73.4 (2C), 72.0, 70.2, 54.0, 50.0, 40.7, 29.9, 28.3, 23.2, 17.0; HRMS (ESI): Calcd for $C_{13}H_{26}N_2O_5$ [M+Na]⁺313.1739, found: 313.1728.

Example 22A: Synthesis of (2S,3R,4S,5S,6S)-5-acetamido-6-(((2S,4aR,6R,7R,8R,8aR)-7-acetamido-6-(((2R,3R,4R,5R,6S)-6-((5-(benzyl((benzyloxy)carbonyl)amino)pentyl)oxy)-2-((benzyloxy)methyl)-4,5-dihydroxytetrahydro-2H-pyran-3-yl)oxy)-2-phenylhexahydropyrano[3,2-d][1,3]dioxin-8-yl)oxy)-4-(((2R,4aR,6R,7S,8R,8aS)-7-acetamido-8-(benzyloxy)-2-phenylhexahydropyrano[3,2-d][1,3]dioxin-6-yl)oxy)-2-methyltetrahydro-2H-pyran-3-yl acetate (22*)

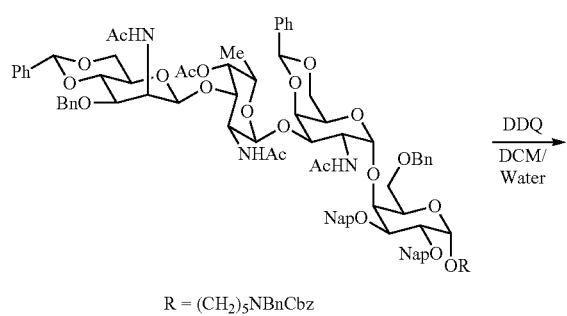

R = (CH₂)₅NBnCbz

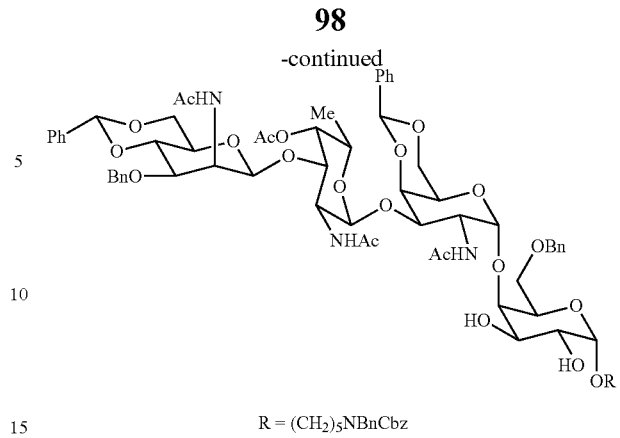

R = (CH₂)₅NBnCbz

To a solution of compound 15* (0.035 g, 0.02 mmol) in a mixture of DCM (1.08 mL) and water (0.06 mL) was added DDQ (0.014 g, 0.06 mmol). The reaction mixture was stirred at room temperature for 3 h. The reaction mixture was diluted with water and DCM. The organic layer was washed with sat aq. Na₂S₂O₃, and sat. aq. NaHCO₃ solution, dried over Na₂SO₄, filtered and concentrated to obtain the crude as oil that was further purified by flash chromatography [(silica gel 60, hexanes and ethyl acetate as eluent (0 to 50%)] to obtain the compound 22* as foam (0.021 g, 71%). HRMS (ESI): Calcd for $C_{80}H_{96}N_4O_{23}$ [M+Na]⁺1503.6363, found: 1503.6434.

Example 23A: Synthesis of (2R,3aR,4S,6R,7S,7aS)-methyl 7-(((2S,4aR,6R,7R,8R,8aR)-7-acetamido-8-(((2S,3S,4S,5R,6S)-3-acetamido-4-(((2R,4aR,6R,7S,8R,8aS)-7-acetamido-8-(benzyloxy)-2-phenylhexahydropyrano[3,2-d] [1,3]dioxin-6-yl)oxy)-5-acetoxy-6-methyltetrahydro-2H-pyran-2-yl)oxy)-2-phenylhexahydropyrano[3,2-d][1,3]dioxin-6-yl)oxy)-4-((5-(benzyl((benzyloxy)carbonyl)amino)pentyl)oxy)-6-((benzyloxy)methyl)-2-methyltetrahydro-3aH-[1,3]dioxolo[4,5-c]pyran-2-carboxylate (23*)

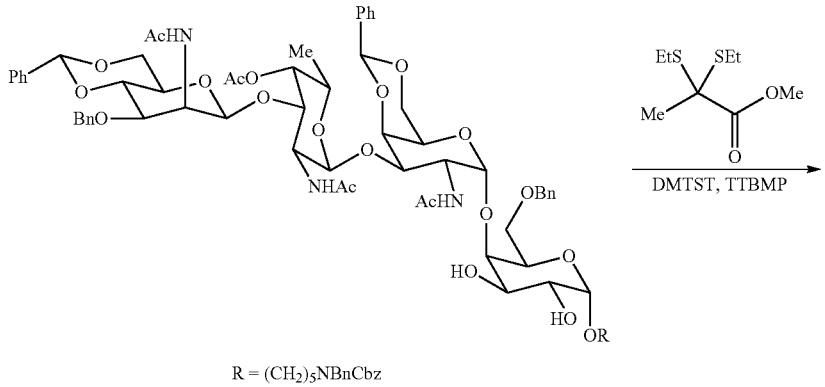

R = (CH₂)₅NBnCbz

-continued

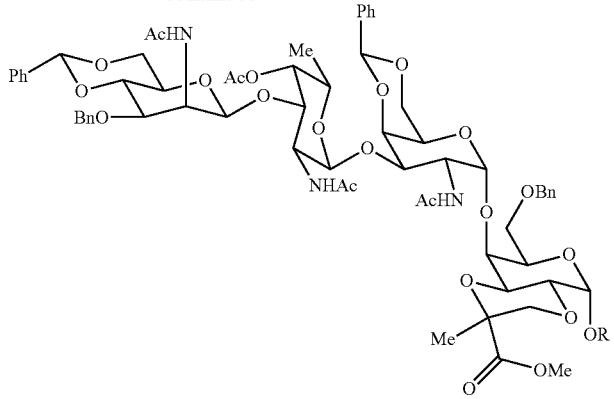

R = (CH$_2$)$_5$NBnCbz

To a solution of compound 22* (0.010 g, 6.75 µmol) in DCM (0.5 mL) was added methyl 2,2-bis(ethylthio)propanoate (0.0084 g, 0.04 mmol), and 2,4,6-tri-tert-butylpyridine (0.023 g, 0.094 mmol), followed by 4 A MS and the reaction mixture stirred at room temperature for 10 min, then cooled to 0° C. and treated with a solution of DMTST (0.0092 g, 0.04 mmol) in DCM (0.2 mL) over a period of 2 h at 0° C. Quenched the reaction mixture with 0.1 mL of Et$_3$N, filtered and removed the solvents under vacuo. Purified the crude by flash chromatography (DCM, Acetone and MeOH as eluent, 50%) to obtain 5 mg of compound 23* as mixture (R and S) (0.005 g, 47%). HRMS (ESI): Calcd for C$_{84}$H$_{101}$N$_4$O$_{25}$ [M+H]$^+$1565.6755, found: 1565.6733.

Example 24A: Synthesis of (2S,3aR,4S,6R,7S,7aS)-7-(((2R,3R,4R,5R,6R)-3-acetamido-4-(((2S,3S,4S,5R,6S)-3-acetamido-4-(((2R,3S,4R,5S,6R)-3-acetamido-4,5-dihydroxy-6-(hydroxymethyl)tetrahydro-2H-pyran-2-yl)oxy)-5-hydroxy-6-methyltetrahydro-2H-pyran-2-yl)oxy)-5-hydroxy-6-(hydroxymethyl)tetrahydro-2H-pyran-2-yl)oxy)-4-((5-aminopentyl)oxy)-6-(hydroxymethyl)-2-methyltetrahydro-3aH-[1,3]dioxolo[4,5-c]pyran-2-carboxylic acid (24*)

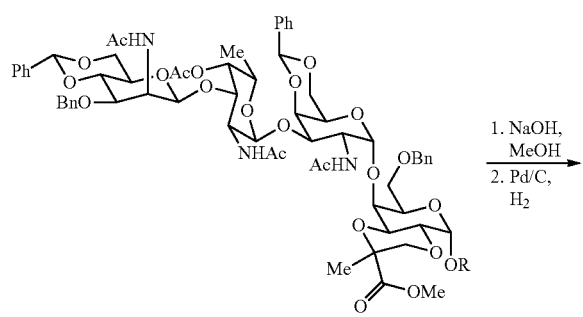

R = (CH$_2$)$_5$NBnCbz

1. NaOH, MeOH
2. Pd/C, H$_2$

-continued

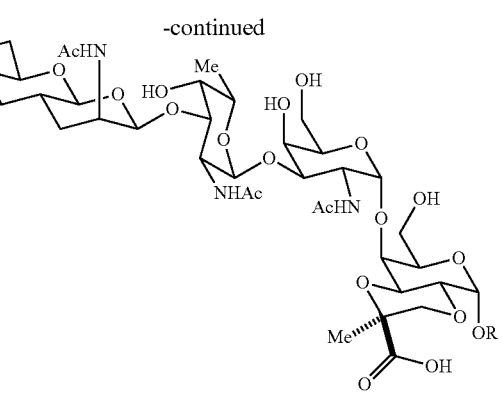

R = (CH$_2$)$_5$NBnCbz

To compound 23* (0.005 g, 3.19 µmol) in MeOH (0.5 mL) was added aq. NaOH (0.085 µL 3.75 M) and the reaction mixture was stirred overnight. The solvent was removed under vacuo, diluted with water and cooled to 0° C. The reaction mixture was neutralized with three drops of acetic acid at 0° C. The aqueous was extracted with EtOAc, dried the organic over Na$_2$SO$_4$, filtered and concentrated to obtain the crude compound, which by $^1$H NMR showed no more the acetate and methyl ester peaks. The crude was taken to the next step without further purification.

A solution of the crude compound in a mixture of MeOH, EtOAc and water (3:2:1; 0.3 mL: 0.2 mL: 0.1 mL) was purged with argon for 3 min followed by the addition of Pd(OH)$_2$/C (10%). The reaction mixture was further purged with H$_2$ and stirred for 48 h under H$_2$ atmosphere. The reaction mixture was filtered through a PTFE filter and the filtrate was washed with a mixture of 1:1 MeOH:water. The solvents were removed under vacuo to obtain the crude compound that was purified by HPLC to obtain target compound 24* (1 mg, 33%) and its R diastereoisomer as byproduct.

HRMS (ESI): Calcd for C$_{38}$H$_{64}$N$_4$O$_{22}$ [M+Na]$^+$951.3910, found: 951.3928.

Compounds 24*a-24*f constitute further examples according to the present invention that can be obtained following the procedure described for compound 24*:

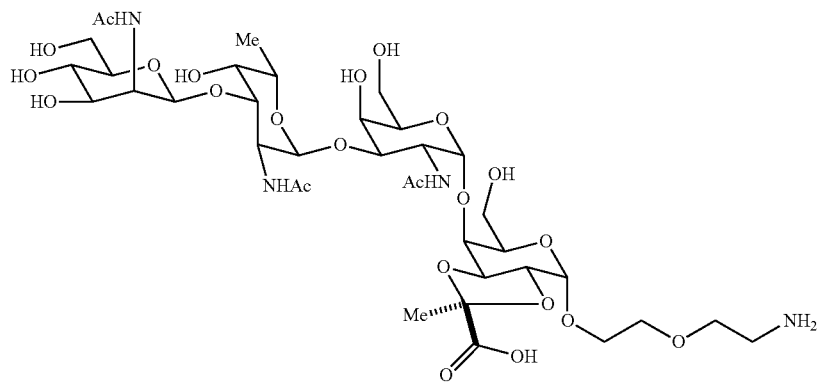
24*a
25
Chemical formula: $C_{37}H_{62}N_4O_{23}$;
Molecular weight: 930.3805;
2-(2-Aminoethoxy)ethyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside
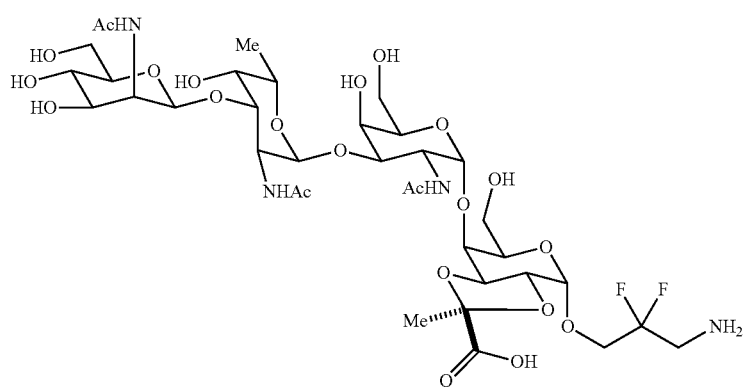
24*b
Chemical formula: $C_{36}H_{58}F_2N_4O_{22}$;
Molecular weight: 936.3511;

3-Amino-2,2-difluoropropyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside 24*c

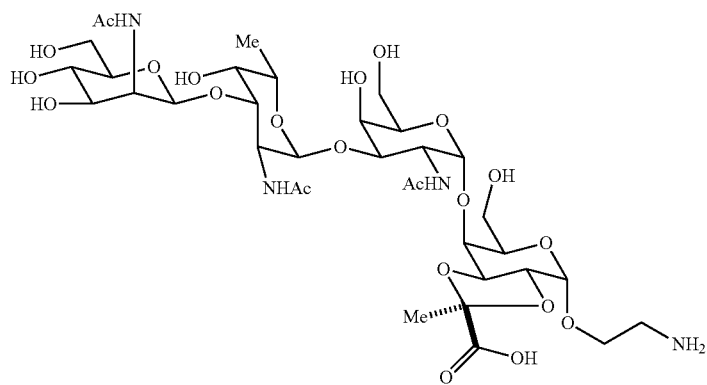

Chemical formula: $C_{35}H_{58}N_4O_{22}$;
Molecular weight: 886.3543;

35

2-Aminoethyl 2-N-acetyl-2-deoxy-β-D-mannopyranosyl-(1→3)-2-N-acetyl-2-deoxy-α-L-fucopyranosyl-(1→3)-2-N-acetyl-2-deoxy-α-D-galactopyranosyl-(1→4)-2,3-O-[1-(S)-(carboxy)-ethylidene]-α-D-galactopyranoside 24*d

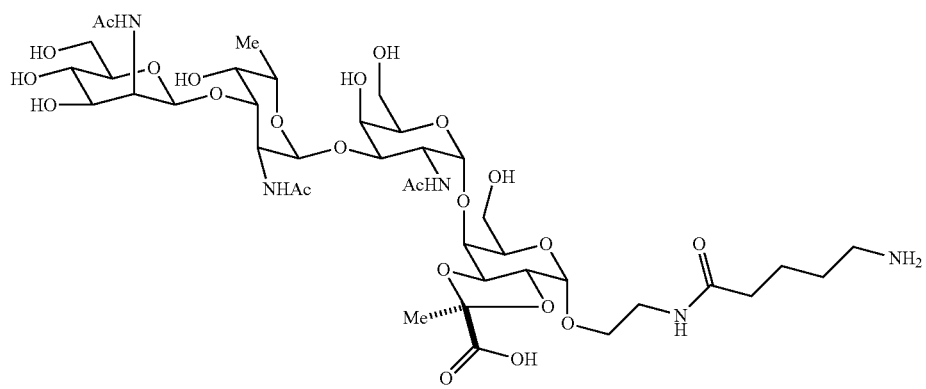

Chemical formula: $C_{40}H_{57}N_5O_{23}$;
Molecular weight: 985.9880;

2-(5-Aminopentanoyl)-aminoethyl 2-N-acetyl-2-
deoxy-β-D-mannopyranosyl-(1→3)-2-N-acetyl-2-
deoxy-α-L-fucopyranosyl-(1→3)-2-N-acetyl-2-de-
oxy-α-D-galactopyranosyl-(1→4)-2,3-O-[1-(S)-
(carboxy)-ethylidene]-α-D-galactopyranoside

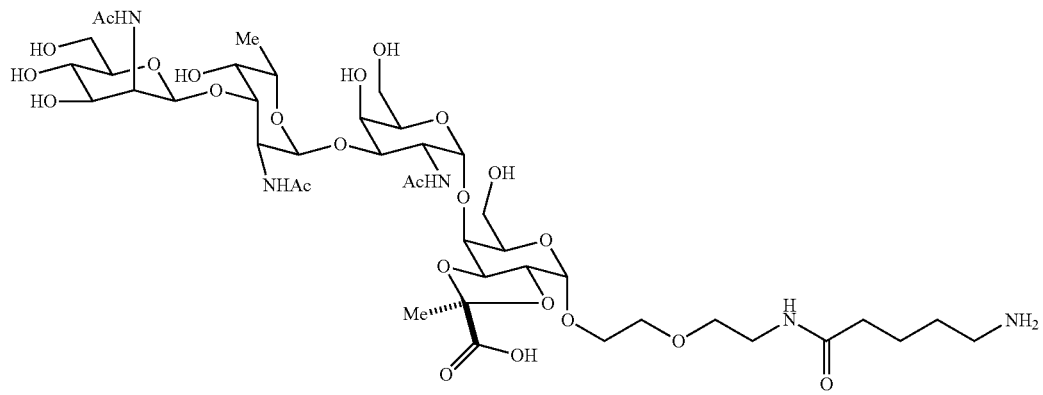

24*e

Chemical formula: $C_{42}H_{71}N_5O_{24}$;
Molecular weight: 1030.0410;

2-(2-(5-Aminopentanoyl)aminoethoxy)ethyl 2-N-
acetyl-2-deoxy-β-D-mannopyranosyl-(1→3)-2-N-
acetyl-2-deoxy-α-L-fucopyranosyl-(1→3)-2-N-
acetyl-2-deoxy-α-D-galactopyranosyl-(14)-2,3-O-[1-
(S)-(carboxy)-ethylidene]-α-D-galactopyranoside

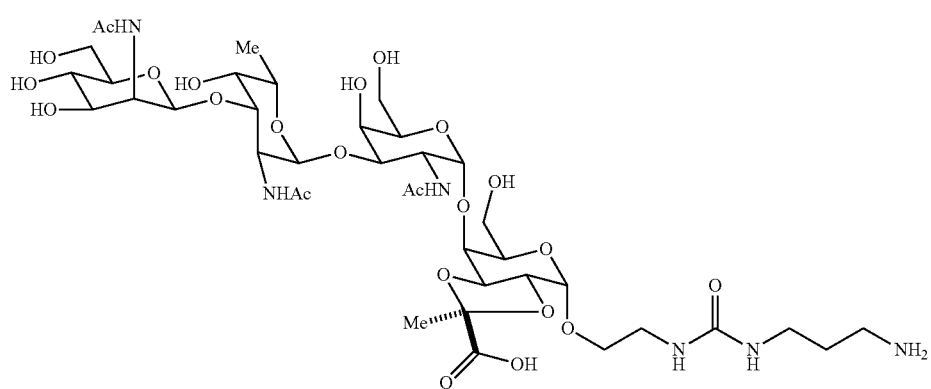

24*f

Chemical formula: $C_{39}H_{66}N_6O_{23}$;
Molecular weight: 986.9760;

2-(3-Amino-1-aminocarbonyl)aminoethyl 2-N-
acetyl-2-deoxy-β-D-mannopyranosyl-(1→3)-2-N-
acetyl-2-deoxy-α-L-fucopyranosyl-(1→3)-2-N-
acetyl-2-deoxy-α-D-galactopyranosyl-(1→4)-2,3-O-
[1-(S)-(carboxy)-ethylidene]-α-D-galactopyranoside B. Biological Evaluation Example 1.B: Glycan Arrays for Determination of
Antibody Binding from Rabbit SP-4 Typing Serum
and Human Reference Serum 007sp Microarray Printing:

Pyruvated SP4 tetrasaccharide 24* was dissolved at 10 mM in water and diluted to 100 μM and 50 μM in coupling buffer (50 mM sodium phosphate, pH 8.5). Each concentration was spotted in duplicates to CodeLink activated glass slides (Surmodics) alongside a number of related structures and native polysaccharides (see FIG. 4 for printing pattern) using a Scienion S3 microarray printer at 65% relative humidity. The slides were incubated in a humidity saturated chamber overnight. They were washed twice with water and quenched by incubation with 100 mM ethanolamine, 50 mM sodium phosphate pH 9 for one hour at room temperature. They were washed again twice, dried by centrifugation and stored at 4° C. until use.

Microarray Incubation:

Slides were blocked by incubation with 1% BSA-PBS at room temperature, washed twice with PBS and dried by centrifugation. A 64 well incubation gasket was attached to the glass slides.

Sera (rabbit SP4 typing serum (SSI Diagnostica, Denmark) or human reference serum 007sp (*Clin. Vaccine*

Immunol. 2011 18 (10), 1728)) were diluted in 1% BSA-PBS containing no competitors or native SP4 CPS (capsular polysaccharide) or CWPS (S. pneumoniae cell wall polysaccharide) as competitors. The dilutions were incubated for 45 min at room temperature and then applied to the microarray according to the attached incubation pattern. After incubation for 1 h at room temperature, wells were washed three times for 5 min with PBS containing 0.05% Tween-20 (PBS-T). Incubation with secondary antibodies dilutions in 1% BSA-PBS (for 007sp wells:goat anti-human IgG Fc AlexaFluor 488 (Dianova) 1:400 and goat anti-human IgM AlexaFluor 594 (Invitrogen) 1:400; for rabbit wells:goat anti-rabbit IgG FITC (Abcam) 1:200) was performed for 30 min at room temperature in the dark. Wells were washed twice with PBS-T, the gasket was removed and the slides was first rinsed with PBS and then with water. It was dried by centrifugation and the fluorescence was read out using s GenePix 4300a fluorescence reader.

Results:
Of all synthetic structures printed to the array, a specific IgG signal in the rabbit typing serum was only observed for the pyruvated SP4 tetrasaccharide 24* (see FIG. 5). This signal could no longer be seen when using native SP4 CPS as competitor, but remained when performing CWPS competition. Compared to the unpyruvated tetrasaccharide 16*, the signal for the pyruvated tetrasaccharide 24* can be inhibited far more efficiently by the native SP4 CPS suggesting a high number of cross-reactive antibodies. CWPS competition has no effect on signal strength.

The invention claimed is:
1. A saccharide of general formula (I)

$$V^*-[U_{x+3}-U_{x+2}-U_{x+1}-U_x]_n\text{-}V\text{-}O\text{-}L\text{-}NH_2 \quad (I)$$

wherein
x is an integer selected from 1, 2, 3 and 4;
n is an integer selected from 1, 2 and 3;

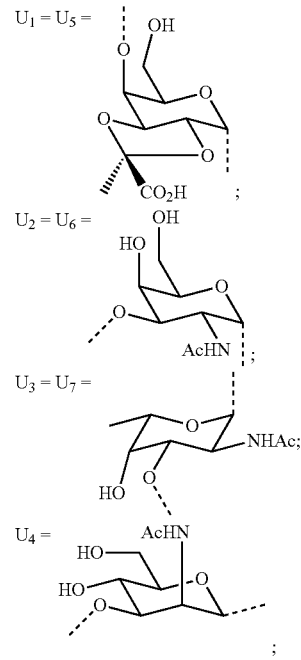

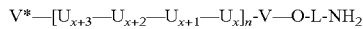

—V— represents a bond, —$U_{x+3}$—, —$U_{x+3}$—$U_{x+2}$— or —$U_{x+3}$—$U_{x+2}$—$U_{x+1}$—;

V*— represents H—, H—$U_x$, H—$U_{x+1}$—$U_x$—, H—$U_{x+2}$—$U_{x+1}$—$U_x$; and
L represents a linker;
or a diastereoisomer or a pharmaceutically acceptable salt thereof.

2. The saccharide according to claim 1 of general formula (II)

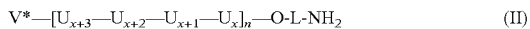

wherein x, n, L, $U_x$, $U_{x+1}$, $U_{x+2}$, $U_{x+3}$ and V* have the meanings as defined in claim 1.

3. The saccharide according to claim 1 of general formula (III)

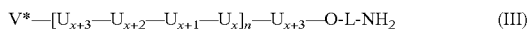

wherein x, n, L, $U_x$, $U_{x+1}$, $U_{x+2}$, $U_{x+3}$ and V* have the meanings as defined in claim 1.

4. The saccharide according to claim 1 of general formula (IV)

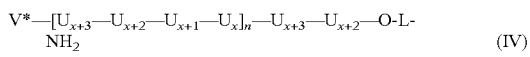

wherein x, n, L, $U_x$, $U_{x+1}$, $U_{x+2}$, $U_{x+3}$ and V* have the meanings as defined in claim 1.

5. The saccharide according to claim 1 of general formula (V)

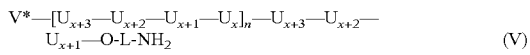

wherein x, n, L, $U_x$, $U_{x+1}$, $U_{x+2}$, $U_{x+3}$ and V* have the meanings as defined in claim 1.

6. The saccharide according to claim 1, wherein x represents 1; and V*— represents H—.

7. A conjugate of general formula (VII)

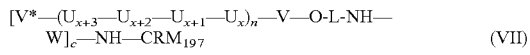

wherein
x is an integer selected from 1, 2, 3 and 4;
n is an integer selected from 1, 2 and 3;

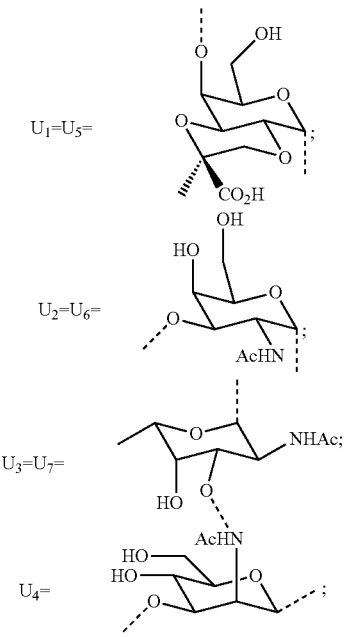

—V— represents a bond, —$U_{x+3}$—, —$U_{x+3}$—$U_{x+2}$— or —$U_{x+3}$—$U_{x+2}$—$U_{x+1}$—;

V*— represents H—, H—$U_x$, H—$U_{x+1}$—$U_x$, H—$U_{x+2}$—$U_{x+1}$—$U_x$—; and L represents a linker;

c is comprised between 2 and 18;

—W— is selected from:

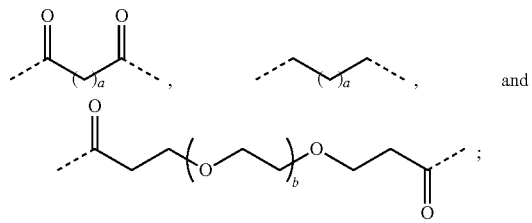

a is an integer selected from 1, 2, 3, 4, 5, 6, 7, 8, 9 and 10,
b is an integer selected from 1, 2, 3 and 4, and
or a diastereoisomer or a pharmaceutically acceptable salt thereof.

8. A method for raising a protective immune response in a human or an animal host against *Streptococcus pneumoniae* serotype 4 comprising administering a therapeutically effective amount of the saccharide according to claim 1 to the human or the animal host.

9. A method for preventing or treating in a human or an animal host a disease comprising administering a therapeutically effective amount of the saccharide according to claim 1 to the human or animal host, wherein the disease is associated with bacteria that contain in their capsular polysaccharide one of the following saccharide fragments:

-3)-β-D-ManNAc-(1, 3)-α-L-FucNAc-(1, 3)-α-D-GalNAc-(1, 4)-α-D-Gal-2,3(S)Pyr-(1-;

-4)-α-D-Gal-2,3(S)Pyr-(1, 3)-β-D-ManNAc-(1, 3)-α-L-FucNAc-(1, 3)-α-D-GalNAc-(1-;

-3)-α-D-GalNAc-(1, 4)-α-D-Gal-2,3(S)Pyr-(1, 3)-β-D-ManNAc-(1, 3)-α-L-FucNAc-(1-; or

-3)-α-L-FucNAc-(1, 3)-α-D-GalNAc-(1, 4)-α-D-Gal-2,3(S)Pyr-(1, 3)-β-D-ManNAc-(1-.

10. The method according to claim 9, wherein the bacteria is *Streptococcus pneumoniae* serotype 4.

11. The method according to claim 9, wherein the diseases associated with bacteria are selected from pneumonia, meningitis, otitis media, bacteremia and acute exacerbation of chronic bronchitis, sinusitis, arthritis and conjunctivitis.

12. A pharmaceutical composition comprising the conjugate according to claim 7, together with at least one pharmaceutically acceptable adjuvant and/or excipient.

13. A method for detecting antibodies against bacteria comprising contacting a sample with the saccharide according to claim 1, wherein the bacteria contain in their capsular polysaccharide one of the following saccharide fragments:

-3)-β-D-ManNAc-(1, 3)-α-L-FucNAc-(1, 3)-α-D-GalNAc-(1, 4)-α-D-Gal-2,3(S)Pyr-(1-;

-4)-α-D-Gal-2,3(S)Pyr-(1, 3)-β-D-ManNAc-(1, 3)-α-L-FucNAc-(1, 3)-α-D-GalNAc-(1-;

-3)-α-D-GalNAc-(1, 4)-α-D-Gal-2,3(S)Pyr-(1, 3)-β-D-ManNAc-(1, 3)-α-L-FucNAc-(1-; or

-3)-α-L-FucNAc-(1, 3)-α-D-GalNAc-(1, 4)-α-D-Gal-2,3(S)Pyr-(1, 3)-β-D-ManNAc-(1-;

and wherein the saccharide is a marker in an immunological assay.

14. The saccharide according to claim 2, wherein x represents 1; and V*— represents H—.

15. The saccharide according to claim 3, wherein x represents 1; and V*— represents H—.

16. The saccharide according to claim 4, wherein x represents 1; and V*— represents H—.

17. The saccharide according to claim 5, wherein x represents 1; and V*— represents H—.

18. The conjugate according to claim 7, wherein x represents 1; and V*— represents H—.

19. The conjugate according to claim 18, wherein —W— represents

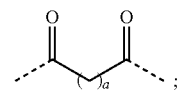

and a is an integer selected from 2, 3, 4, 5 and 6.

20. The conjugate of claim 19, wherein -L- represents —$(CH_2)_o$—; and o is an integer selected from 2, 3, 4, 5 and 6.

21. The conjugate of claim 20, wherein c is comprised between 8 and 12; and n represents 1.

22. A method for raising a protective immune response in a human or an animal host against *Streptococcus pneumoniae* serotype 4 comprising administering a therapeutically effective amount of the conjugate according to claim 7 to the human or the animal host.

23. A method for preventing or treating in a human or an animal host a disease comprising administering a therapeutically effective amount of the conjugate according to claim 7 to the human or the animal host, wherein the disease is associated with bacteria that contain in their capsular polysaccharide one of the following saccharide fragments:

-3)-β-D-ManNAc-(1, 3)-α-L-FucNAc-(1, 3)-α-D-GalNAc-(1, 4)-α-D-Gal-2,3(S)Pyr-(1-;

-4)-α-D-Gal-2,3(S)Pyr-(1, 3)-β-D-ManNAc-(1, 3)-α-L-FucNAc-(1, 3)-α-D-GalNAc-(1-;

-3)-α-D-GalNAc-(1, 4)-α-D-Gal-2,3(S)Pyr-(1, 3)-β-D-ManNAc-(1, 3)-α-L-FucNAc-(1-; or

-3)-α-L-FucNAc-(1, 3)-α-D-GalNAc-(1, 4)-α-D-Gal-2,3(S)Pyr-(1, 3)-β-D-ManNAc-(1-.

24. The method according to claim 23, wherein the diseases associated with bacteria are selected from pneumonia, meningitis, otitis media, bacteremia and acute exacerbation of chronic bronchitis, sinusitis, arthritis and conjunctivitis.

25. A pharmaceutical composition comprising the saccharide according to claim 1, together with at least one pharmaceutically acceptable adjuvant and/or excipient.

* * * * *